US011357849B2

(12) United States Patent
Fernandes et al.

(10) Patent No.: US 11,357,849 B2
(45) Date of Patent: Jun. 14, 2022

(54) ANTI-NUCLEOLIN ANTIBODIES

(71) Applicants: CharlestonPharma, LLC, Charleston, SC (US); MUSC Foundation for Research Development, Charleston, SC (US)

(72) Inventors: Daniel Fernandes, Awendaw, SC (US); Laura Schwartz, Charleston, SC (US); Natalie Sutkowski, Charleston, SC (US); Brian Hoel, Charleston, SC (US); Semyon Rubinchik, Buffalo Grove, IL (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 344 days.

(21) Appl. No.: 16/080,720

(22) PCT Filed: Mar. 7, 2017

(86) PCT No.: PCT/US2017/021203
§ 371 (c)(1),
(2) Date: Aug. 29, 2018

(87) PCT Pub. No.: WO2017/156032
PCT Pub. Date: Sep. 14, 2017

(65) Prior Publication Data
US 2019/0194334 A1    Jun. 27, 2019

Related U.S. Application Data

(60) Provisional application No. 62/414,316, filed on Oct. 28, 2016, provisional application No. 62/323,159, filed on Apr. 15, 2016, provisional application No. 62/304,742, filed on Mar. 7, 2016.

(51) Int. Cl.
*A61K 39/395* (2006.01)
*C07K 16/18* (2006.01)
*A61P 35/00* (2006.01)
*C07K 16/30* (2006.01)
*C07K 16/28* (2006.01)
*A61K 39/00* (2006.01)
*A61K 38/00* (2006.01)

(52) U.S. Cl.
CPC ........ *A61K 39/395* (2013.01); *A61K 39/3955* (2013.01); *A61P 35/00* (2018.01); *C07K 16/18* (2013.01); *A61K 38/00* (2013.01); *A61K 2039/505* (2013.01); *C07K 16/28* (2013.01); *C07K 16/2857* (2013.01); *C07K 16/3015* (2013.01); *C07K 16/3061* (2013.01); *C07K 2317/21* (2013.01); *C07K 2317/56* (2013.01); *C07K 2317/565* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,485,045 A | 11/1984 | Regen | |
| 4,496,689 A | 1/1985 | Mitra | |
| 4,544,545 A | 10/1985 | Ryan et al. | |
| 4,640,835 A | 2/1987 | Shimizu et al. | |
| 4,657,760 A | 4/1987 | Kung et al. | |
| 4,670,417 A | 6/1987 | Iwasaki et al. | |
| 4,791,192 A | 12/1988 | Nakagawa et al. | |
| 4,816,567 A | 3/1989 | Cabilly et al. | |
| 4,975,278 A | 12/1990 | Senter et al. | |
| 5,013,556 A | 5/1991 | Woodle et al. | |
| 5,206,344 A | 4/1993 | Katre et al. | |
| 5,225,212 A | 7/1993 | Martin et al. | |
| 5,534,615 A | 7/1996 | Baker et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,595,756 A * | 1/1997 | Bally ................. A61K 9/1272 264/4.1 |
| 5,625,126 A | 4/1997 | Lonberg et al. | |
| 5,633,425 A | 5/1997 | Lonberg et al. | |
| 5,648,237 A | 7/1997 | Carter | |
| 5,661,016 A | 8/1997 | Lonberg et al. | |
| 5,789,199 A | 8/1998 | Joly et al. | |
| 5,840,523 A | 11/1998 | Simmons et al. | |

(Continued)

FOREIGN PATENT DOCUMENTS

EP          0404097 A2    12/1990
JP          H7-242566      9/1995

(Continued)

OTHER PUBLICATIONS

Vajdos et al. (J Mol Biol. Jul. 5, 2002;320(2):415-28 (Year: 2002).*
Brown et al. (J Immunol. May 1996;156(9):3285-91 (Year: 1996).*
McGuinness et al. (Mol. Microbiol., 7:505-514, 1993) (Year: 1993).*
Moudallal et al. (EMBO Journal, 1:1005-1010, 1982) (Year: 1982).*
Abaza et al. (J. Prot. Chem., 11:433-444, 1992) (Year: 1992).*
Christiansen et al (Mol Cancer Ther, 2004, 3:1493-1501) (Year: 2004).*
Topp et al (Journal of Controlled Release, 1998, 53:15-23) (Year: 1998).*
The FDA Guideline for Industry Dose-response Information to Support Drug Registration (ICH-E4, Nov. 1994) (Year: 1994).*

(Continued)

*Primary Examiner* — Brian Gangle
*Assistant Examiner* — Andrea K McCollum
(74) *Attorney, Agent, or Firm* — Parker Highlander PLLC

(57) ABSTRACT

The present disclosure provides anti-nucleolin antibodies, methods of producing anti-nucleolin antibodies, and cells producing anti-nucleolin antibodies. Also provided are methods of using anti-nucleolin antibodies in treating malignant and non-malignant diseases.

12 Claims, 16 Drawing Sheets
Specification includes a Sequence Listing.

(56) References Cited

U.S. PATENT DOCUMENTS

| | | | |
|---|---|---|---|
| 5,959,177 | A | 9/1999 | Hein et al. |
| 5,981,214 | A | 11/1999 | Skoultchi |
| 6,040,498 | A | 3/2000 | Stomp et al. |
| 6,075,181 | A | 6/2000 | Kucherlapati et al. |
| 6,150,584 | A | 11/2000 | Kucherlapati et al. |
| 6,417,429 | B1 | 7/2002 | Hein et al. |
| 6,420,548 | B1 | 7/2002 | Vezina et al. |
| 7,125,978 | B1 | 10/2006 | Vezina et al. |
| 8,715,743 | B2 | 5/2014 | Sutkowski et al. |
| 2013/0115674 | A1 | 5/2013 | Sutkowski et al. |

FOREIGN PATENT DOCUMENTS

| | | |
|---|---|---|
| WO | WO-8101145 A1 | 4/1981 |
| WO | WO-9110741 A1 | 7/1991 |
| WO | WO-9301161 A1 | 1/1993 |
| WO | WO-9323572 A1 | 11/1993 |
| WO | WO-9632478 A1 | 10/1996 |
| WO | WO-9633735 A1 | 10/1996 |
| WO | WO-9634096 A1 | 10/1996 |
| WO | WO-9824893 A2 | 6/1998 |
| WO | WO-2005035579 A1 | 4/2005 |
| WO | WO-2009020923 A1 | 2/2009 |
| WO | WO-2011062997 A2 | 5/2011 |
| WO | WO-2012167173 A1 | 12/2012 |

OTHER PUBLICATIONS

Sporn et al, "Chemoprevention of Cancer," Carcinogenesis, vol. 21 (2000), 525-530 (Year: 2000).*

Auerbach et al (Cancer and Metastasis Reviews, 2000, 19: 167-172) (Year: 2000).*

Gura T (Science, 1997, 278(5340): 1041-1042 (Year: 1997).*

Jain RK (Scientific American, Jul. 1994,58-65) (Year: 1994).*

HogenEsch et al (J Control Release. Dec. 10, 2012; 164(2): 183-186.) (Year: 2012).*

Abdelmohsen et al. (RNA Biology 9:6, 799-808; Jun. 2012) (Year: 2012).*

Boerner, et al. Production of antigen-specific human monoclonal antibodies from in vitro-primed human splenocytes. J Immunol. Jul. 1, 1991;147(1):86-95.

Bruggemann, et al. Designer mice: the production of human antibody repertoires in transgenic animals. Year Immunol. 1993;7:33-40.

Charlton, Keith A., "Expression and Isolation of Recombinant Antibody Fragments in E. coli"Methods in Molecular Biology, vol. 248, pp. 245-254, 2003.

Chothia, Cyru et al., "Conformations of immunoglobulin hypervariable regions", Nature, 1989, 342:887.

Chowdhury, Partha S., "Engineering Hot Spots for Affinity Enhancement of Antibodies", Methods Mol. Biol 207:179-196, 2008.

Clackson, et al. Making antibody fragments using phage display libraries. Nature. Aug. 15, 1991;352(6336):624-8.

Cole et al., "The EBV-hybridoma technique and its application to human lung cancer," In: Monoclonal Antibodies and Cancer Therapy, vol. 27, UCLA Symposia on Molecular and Cellular Biology, New Series, Eds. R.A. Reisfeld and S.Sell, pp. 77-96, Alan R. Liss, Inc. N.Y., 1985.

Cunningham, et al. High-resolution epitope mapping of hGH-receptor interactions by alanine-scanning mutagenesis. Science. Jun. 2, 1989;244(4908):1081-5.

Fellouse, et al. Synthetic antibodies from a four-amino-acid code: a dominant role for tyrosine in antigen recognition. Proc Natl Acad Sci USA. Aug. 24, 2004;101(34):12467-72. Epub Aug. 11, 2004.

Fernandes, Daniel et al., "Development of anti-nucleolin antibodies with broad spectrum anticancer activity and negligible toxicity to normal cells", Cancer Research, 2016, XP55613025.

Fishwild, et al. High-avidity human IgG kappa monoclonal antibodies from a novel strain of minilocus transgenic mice. Nat Biotechnol. Jul. 1996;14(7):845-51. Nat Biotechnol. Jul. 1996;14(7):845-51.

Gerngross, Tillman U., " Advances in the production of human therapeutic proteins in yeasts and filamentous fungi", Nature Biotechnology, 22:1409-1414, 2004.

Graham, F.L. et al., "Characteristics of a Human Cell Line Transformed by DNA from Human Adenovirus Type 5", Journal of General Virology, 1977, vol. 36, issue 1, pp. 59-72.

Hammerling et al., in: Monoclonal Antibodies and T -Cell Hybridomas, pp. 563-681, Elsevier, N.Y., 1981.

Harlow et al., Antibodies: A Laboratory Manual, Cold Spring Harbor Laboratory Press, 2nd ed. 1988.

Harris. Production of humanized monoclonal antibodies for in vivo imaging and therapy. Biochem Soc Trans. Nov. 1995;23(4):1035-8.

Holliger, P et al. ""Diabodies": small bivalent and bispecific antibody fragments." Proceedings of the National Academy of Sciences of the United States of America vol. 90,14 (1993): 6444-8. doi:10.1073/pnas.90.14.6444.

Hongo, et al. Development and characterization of murine monoclonal antibodies to the latency-associated peptide of transforming growth factor beta 1. Hybridoma. Jun. 1995;14(3):253-60.

Hoogenboom, et al. By-passing immunisation. Human antibodies from synthetic repertoires of germline VH gene segments rearranged in vitro. J Mol Biol. Sep. 20, 1992;227(2):381-8.

Hudson et al., "Engineered antibodies", Nature Medicine, 2003, vol. 9, No. 1, pp. 129-134.

Hurle, et al. Protein engineering techniques for antibody humanization. Curr Opin Biotechnol. Aug. 1994;5(4):428-33.

Jakobovits et al. Analysis of homozygous mutant chimeric mice: deletion of the immunoglobulin heavy-chain joining region blocks B-cell development and antibody production. Proc Natl Acad Sci U S A., 90.6 (1993) :2551-2555.

Jakobovits, et al. Germ-line transmission and expression of a human-derived yeast artificial chromosome. Nature. Mar. 18, 1993;362(6417):255-8.

Jones et al. Replacing the complementarity-determining regions in a human antibody with those from a mouse. Nature, 321.6069 (1986): 522-5.

Kabat, Elvin A. Sequences of Proteins of Immunological Interest. Bethesda, MD: U.S. Dept. of Health and Human Services, Public Health Service, National Institutes of Health, 1991, vol. 1, fifth edition.

Kam, Nadine Wong Shi et al. "Carbon nanotubes as multifunctional biological transporters and near-infrared agents for selective cancer cell destruction." Proceedings of the National Academy of Sciences of the United States of America vol. 102,33 (2005): 11600-5. doi:10.1073/pnas.0502680102.

Kunik, Vered et al. "Paratome: an online tool for systematic identification of antigen-binding regions in antibodies based on sequence or structure." Nucleic acids research vol. 40,Web Server issue (2012): W521-4. doi:10.1093/nar/gks480.

Lee, et al. High-affinity human antibodies from phage-displayed synthetic Fab libraries with a single framework scaffold. J Mol Biol. Jul. 23, 2004;340(5):1073-93.

Lefranc, Marie-Paule, "The IMGT Unique Numbering for Immunoglobulins, T-Cell Receptors, and Ig-Like Domains", The Immunologist, 7, 132-136, 1999.

Li, et al. Human antibodies for immunotherapy development generated via a human B cell hybridoma technology. Proc Natl Acad Sci U S A. Mar. 7, 2006;103(10):3557-62. Epub Feb. 27, 2006.

Lonberg, et al. Antigen-specific human antibodies from mice comprising four distinct genetic modifications. Nature. Apr. 28, 1994;368(6474):856-9.

Lonberg, et al. Human antibodies from transgenic mice. Int Rev Immunol. 1995;13(1):65-93.

Lyskov, Sergey et al. "Serverification of molecular modeling applications: the Rosetta Online Server that Includes Everyone (ROSIE)." PloS one vol. 8,5 e63906. May 22, 2013, doi:10.1371/journal.pone.0063906.

Marcatili Paolo et al., "PIGS: Automatic prediction of antibody structures", Bionformatics, 2008, vol. 24, No. 17, pp. 1953-1954.

Maris, Christophe, et al., "The RNA recognition motif, a plastic RNA-binding platform to regulate post-transcriptional gene expression" FEBS Journal, 2005, vol. 272, pp. 2118-2131.

(56) References Cited

OTHER PUBLICATIONS

Marks, et al. By-passing immunization. Human antibodies from V-gene libraries displayed on phage. J Mol Biol. Dec. 5, 1991;222(3):581-97.

Marks, et al. By-passing immunization: building high affinity human antibodies by chain shuffling. Biotechnology (N Y). Jul. 1992;10(7):779-83.

Morrison. Immunology. Success in specification. Nature. Apr. 28, 1994;368(6474):812-3.

Neuberger. Generating high-avidity human Mabs in mice. Nat Biotechnol. Jul. 1996;14(7):826.

Palmieri, D et al., "Human anti-nucleolien recombinant immunoagent for cancer therapy", PNAS, Jul. 28, 2015, vol. 112, No. 30, pp. 9418-9423.

Presta. Antibody Engineering. Curr. Op. Struct. Bioi. 1992; 2:593-596.

Riechmann et al. Reshaping human antibodies for therapy. Nature, 332.6162 (1988): 323-7.

Rosenburg and Moore, "The Pharmacology of Monoclonal Antibodies", Springer-Verlag, 1994, vol. 113, pp. 269-315.

Sidhu, et al. Phage-displayed antibody libraries of synthetic heavy chain complementarity determining regions. J Mol Biol. Apr. 23, 2004;338(2):299-310.

Srivastava, M. et al., "Cloning and sequencing of the human nucleolin cDNA", Febs Letters, 1989, vol. 250, No. 1, pp. 99-105.

Supplementary European Search Report and Written Opinion dated Aug. 23, 2019 for Application No. EP 17 76 3929, (9 pages).

Van Dijk, et al. Human antibodies as next generation therapeutics. Curr Opin Chem Biol. Aug. 2001;5(4):368-74.

Vaswani, et al. Humanized antibodies as potential therapeutic drugs. Ann Allergy Asthma Immunol. Aug. 1998;81(2):105-15; quiz 115-6, 119.

Yazaki and Wu, "Expression of Recombinant Antibodies in Mammalian Cell Lines", Methods in Molecular Biology, vol. 248, pp. 255-268, 2003.

English translation of Office Communication issued in Japanese Patent Application No. 2018-547926, dated Apr. 21, 2021.

Hanakahi et al., "Nucleolin is one component of the B cell-specific transcription factor and switch region binding protein, LR1," *Proc. Natl. Acad. Sci. USA*, 94:365-3610, 1997.

\* cited by examiner

1. MW markers
2. CHO3E7 negative control CCS
3. CP1 gamma heavy chain / kappa light chain CHO3E7 CCS
4. CP1 gamma heavy chain / kappa light chain (second transfection) CHO3E7 CCS 1. MW markers
2. CHO3E7 negative control CCS
3. CP1 gamma heavy chain / lambda light chain CHO3E7 CCS
4. CP1 gamma heavy chain / lambda light chain (second transfection) CHO3E7 CCS Group 1

Mouse # 10

Mice # 1, # 3

Group 2

US 11,357,849 B2

ANTI-NUCLEOLIN ANTIBODIES

CROSS-REFERENCE

This application claims the benefit of U.S. Provisional Application No. 62/304,742, filed on Mar. 7, 2016, U.S. Provisional Application No. 62/323,159, filed on Apr. 15, 2016, U.S. Provisional Application No. 62/414,316, filed on Oct. 28, 2016, all of which are incorporated herein by reference in their entirety.

STATEMENT AS TO FEDERALLY SPONSORED RESEARCH

The invention was made with government support under grant number NCI CA109254-04S1 awarded by the National Cancer Institute, National Institutes of Health of the United States, and grants #W81XWH-12-1-0241 and #W81XWH-12-1-0242 awarded by the U.S. Army Medical Research and Materiel Command. The government has certain rights in the invention.

SEQUENCE LISTING

The instant application contains a Sequence Listing which has been submitted electronically in ASCII format and is hereby incorporated by reference in its entirety. Said ASCII copy, created on Mar. 7, 2017, is named 39723-709_601_SL.txt and is 60,062 bytes in size.

INCORPORATION BY REFERENCE

All publications, patents, and patent applications disclosed herein are incorporated by reference to the same extent as if each individual publication, patent, or patent application was specifically and individually indicated to be incorporated by reference. In the event of a conflict between a term disclosed herein and a term in an incorporated reference, the term herein controls.

BACKGROUND

Antibodies are a class of agents known as "biologicals." The source of antibodies can be a polyclonal supply, such as human or horse serum, or derived from a monoclonal source (single cell clone). With the technologic capability to control and select for specific antigen binding, monoclonal antibodies have yielded dramatic therapeutic benefits. However, the difficulty of generating specific antibodies for certain targets has limited the successes, and the potential for therapeutic agents remains largely untapped.

One impediment to the development of monoclonal antibodies for human therapy is the need to "humanize" such antibodies, which are generally made in mice, rats and rabbits. If human patients are administered such antibodies without humanized constant regions, they can suffer from "serum sickness," meaning that an endogenous immune response is mounted by the recipient against the non-human antibody sequences. Humanizing monoclonal antibodies produced in research animals can avoid this problem. However, the cost in time and expense for humanization of antibodies can be considerable.

Nucleolin is expressed on the cell surface of chronic lymphocytic leukemia (CLL) cells, acute myeloid leukemia (AML) cells, some forms of breast carcinoma, as well as other tumors. As such, nucleolin constitutes a promising tumor antigen for targeting of therapeutics, including antibodies.

BRIEF SUMMARY

In some of many aspects, the present disclosure is directed to specific antibodies that immunologically recognize, bind to, and/or inactivate nucleolin. Also provided herein are light and heavy chain sequences of anti-nucleolin antibodies that may either be used directly to prepare anti-nucleolin antibodies (e.g., human and/or monoclonal), or can be used to provide specific sequence elements (e.g., CDR sequences) that may be incorporated into different, desired antibody backgrounds. Antibodies that comprise the sequences disclosed herein can be used in a wide range of therapies directed to disabling nucleolin.

In some cases, provided herein is an isolated antibody or fragment thereof, wherein the isolated antibody or fragment thereof binds to human nucleolin and comprises: a heavy chain CDR1 having at least 60% sequence identity to amino acid sequence SEQ ID NO:42; a heavy chain CDR2 having at least 60% sequence identity to amino acid sequence YIS; a heavy chain CDR3 having at least 60% sequence identity to amino acid sequence DM; a light chain CDR1 having at least 60% sequence identity to amino acid sequence SEQ ID NO:65; a light chain CDR2 having at least 60% sequence identity to amino acid sequence SEQ ID NO:54; and a light chain CDR3 having at least 60% sequence identity to amino acid sequence SEQ ID NO:66. In some embodiments, the at least 60% sequence identity is at least 65%, 70%, 75%, 80%, 85%, 90%, 95%, or 98%, or 100% sequence identity.

In some cases, provided herein is an isolated antibody or fragment thereof, wherein the isolated antibody or fragment thereof binds to human nucleolin and comprises: a heavy chain CDR1 has an amino acid sequence that comprises SEQ ID NO:42; a heavy chain CDR2 has an amino acid sequence that comprises YIS; a heavy chain CDR3 has an amino acid sequence that comprises DM; a light chain CDR1 has an amino acid sequence that comprises SEQ ID NO:65; a light chain CDR2 has an amino acid sequence that comprises SEQ ID NO:54; and a light chain CDR3 has an amino acid sequence that comprises SEQ ID NO:66.

In some cases, provided herein is an isolated antibody or fragment thereof, wherein the isolated antibody or fragment thereof binds to human nucleolin and comprises: a heavy chain CDR1 having at least 60% sequence identity to an amino acid sequence selected from the group consisting of SEQ ID NOS. 24 to 26; a heavy chain CDR2 having at least 60% sequence identity to an amino acid sequence selected from the group consisting of YIS and SEQ ID NOS. 30 to 32; a heavy chain CDR3 having at least 60% sequence identity to an amino acid sequence selected from the group consisting of SEQ ID NOS. 37 to 39; a light chain CDR1 having at least 60% sequence identity to an amino acid sequence selected from the group consisting of SEQ ID NOS. 46 to 48; a light chain CDR2 having at least 60% sequence identity to an amino acid sequence selected from the group consisting of SEQ ID NOS. 52 to 54; and a light chain CDR3 having at least 60% sequence identity to an amino acid sequence selected from the group consisting of SEQ ID NOS. 58 to 61. In some embodiments, the at least 60% sequence identity is at least 65%, 70%, 75%, 80%, 85%, 90%, 95%, or 98%, or 100% sequence identity.

In some cases, provided herein is an isolated antibody or fragment thereof, wherein the isolated antibody or fragment thereof binds to human nucleolin and comprises: the heavy chain CDR1 has the amino acid sequence of SEQ ID NO:24; the heavy chain CDR2 has the amino acid sequence of SEQ ID NO:30; the heavy chain CDR3 has the amino acid sequence of SEQ ID NO:37; the light chain CDR1 has the amino acid sequence of SEQ ID NO:46; the light chain CDR2 has the amino acid sequence of SEQ ID NO:52; and the light chain CDR3 has the amino acid sequence of SEQ ID NO:58.

In some cases, provided herein is an isolated antibody or fragment thereof, wherein the isolated antibody or fragment thereof binds to human nucleolin and comprises: the heavy chain CDR1 has the amino acid sequence of SEQ ID NO:25; the heavy chain CDR2 has the amino acid sequence of SEQ ID NO:31; the heavy chain CDR3 has the amino acid sequence of SEQ ID NO:38; the light chain CDR1 has the amino acid sequence of SEQ ID NO:47; the light chain CDR2 has the amino acid sequence of SEQ ID NO:53; and the light chain CDR3 has the amino acid sequence of SEQ ID NO:59.

In some cases, provided herein is an isolated antibody or fragment thereof, wherein the isolated antibody or fragment thereof binds to human nucleolin and comprises: the heavy chain CDR1 has the amino acid sequence of SEQ ID NO:26; the heavy chain CDR2 has the amino acid sequence of YIS; the heavy chain CDR3 has the amino acid sequence of SEQ ID NO:39; the light chain CDR1 has the amino acid sequence of SEQ ID NO:48; the light chain CDR2 has the amino acid sequence of SEQ ID NO:54; and the light chain CDR3 has the amino acid sequence of SEQ ID NO:60.

In some cases, provided herein is an isolated antibody or fragment thereof, wherein the isolated antibody or fragment thereof binds to human nucleolin and comprises: the heavy chain CDR1 has the amino acid sequence of SEQ ID NO:24; the heavy chain CDR2 has the amino acid sequence of SEQ ID NO:32; the heavy chain CDR3 has the amino acid sequence of SEQ ID NO:37; the light chain CDR1 has the amino acid sequence of SEQ ID NO:46; the light chain CDR2 has the amino acid sequence of SEQ ID NO:52; and the light chain CDR3 has the amino acid sequence of SEQ ID NO:61.

In some cases, provided herein is an isolated antibody or fragment thereof, wherein the isolated antibody or fragment thereof binds to human nucleolin and comprises: a heavy chain variable region (VH) that has at least 60% sequence identity to the amino acid sequence of SEQ ID NO:3; and a light chain variable region (VL) that has at least 60% sequence identity to the amino acid sequence of SEQ ID NO:12. In some embodiments, the at least 60% sequence identity is at least: 65%, 70%, 75%, 80%, 85%, 90%, 95%, or 98%, or 100% sequence identity.

In some cases, provided herein is an isolated antibody or fragment thereof, wherein the isolated antibody or fragment thereof binds to human nucleolin and comprises: a VH that has an amino acid sequence of SEQ ID NO:3; and a VL has the amino acid sequence of SEQ ID NO:12.

In some cases, provided herein is an isolated antibody or fragment thereof, wherein the isolated antibody or fragment thereof binds to human nucleolin and comprises: a heavy chain that has at least 60% sequence identity to the amino acid sequence of SEQ ID NO:2; and a light chain that has at least 60% identity to the amino acid sequence of SEQ ID NO:11. In some embodiments, the amino acid sequence of SEQ ID NO:2 is encoded by the nucleotide sequence of SEQ ID NO:1. In some embodiments, the amino acid sequence of SEQ ID NO:11 is encoded by the nucleotide sequence of SEQ ID NO:10. In some embodiments, the at least 60% sequence identity is at least: 65%, 70%, 75%, 80%, 85%, 90%, 95%, or 98%, or 100% sequence identity.

In some cases, provided herein is an isolated antibody or fragment thereof, wherein the isolated antibody or fragment thereof binds to human nucleolin and comprises: a heavy chain that has at least 60% sequence identity to the amino acid sequence of SEQ ID NO:14; and a light chain that has at least 60% identity to the amino acid sequence of SEQ ID NO:11. In some embodiments, the at least 60% sequence identity is at least: 65%, 70%, 75%, 80%, 85%, 90%, 95%, or 98%, or 100% sequence identity.

In some cases, provided herein is an isolated antibody or fragment thereof that comprises a heavy chain with the amino acid sequence of SEQ ID NO:2; and a light chain with the amino acid sequence of SEQ ID NO:11. In some cases, provided herein is an isolated antibody or fragment thereof that comprises a heavy chain with the amino acid sequence of SEQ ID NO:14; and a light chain with the amino acid sequence of SEQ ID NO:11.

In some cases, provided herein is an isolated antibody or fragment thereof, wherein the isolated antibody or fragment thereof binds to human nucleolin and comprises: a heavy chain CDR1 having at least 60% sequence identity to an amino acid sequence of DYF; a heavy chain CDR2 having at least 60% sequence identity to an amino acid sequence of SEQ ID NO:74; a heavy chain CDR3 having at least 60% sequence identity to an amino acid sequence of AR or SEQ ID NO:77; a light chain CDR1 having at least 60% sequence identity to an amino acid sequence of SEQ ID NO:84; a light chain CDR2 having at least 60% sequence identity to an amino acid sequence of NVS; and a light chain CDR3 having at least 60% sequence identity to an amino acid sequence of SEQ ID NO:91. In some embodiments, the at least 60% sequence identity is at least: 65%, 70%, 75%, 80%, 85%, 90%, 95%, or 98%, or 100% sequence identity.

In some cases, provided herein is an isolated antibody or fragment thereof, wherein the isolated antibody or fragment thereof binds to human nucleolin and comprises: a heavy chain CDR1 has an amino acid sequence that comprises DYF; a heavy chain CDR2 has an amino acid sequence that comprises SEQ ID NO:74; a heavy chain CDR3 has an amino acid sequence that comprises AR or SEQ ID NO:77; a light chain CDR1 has an amino acid sequence that comprises SEQ ID NO:84; a light chain CDR2 has an amino acid sequence that comprises NVS; and a light chain CDR3 has an amino acid sequence that comprises SEQ ID NO:91.

In some cases, provided herein is an isolated antibody or fragment thereof, wherein the isolated antibody or fragment thereof binds to human nucleolin and comprises: a heavy chain CDR1 having at least 60% sequence identity to an amino acid sequence of SEQ ID NO:69 or SEQ ID NO:70; a heavy chain CDR2 having at least 60% sequence identity to an amino acid sequence of SEQ ID NO:73 or SEQ ID NO:74; a heavy chain CDR3 having at least 60% sequence identity to an amino acid sequence of AR, SEQ ID NO:77, or SEQ ID NO:78; a light chain CDR1 having at least 60% sequence identity to an amino acid sequence of SEQ ID NO:83 or SEQ ID NO:84; a light chain CDR2 having at least 60% sequence identity to an amino acid sequence of NVS or SEQ ID NO:87; and a light chain CDR3 having at least 60% sequence identity to an amino acid sequence of SEQ ID NO:90 or SEQ ID NO:91. In some embodiments, the at least 60% sequence identity is at least: 65%, 70%, 75%, 80%, 85%, 90%, 95%, or 98%, or 100% sequence identity.

In some cases, provided herein is an isolated antibody or fragment thereof, wherein the isolated antibody or fragment thereof binds to human nucleolin and comprises: the heavy chain CDR1 has the amino acid sequence of SEQ ID NO:69; the heavy chain CDR2 has the amino acid sequence of SEQ ID NO:73; the heavy chain CDR3 has the amino acid sequence of SEQ ID NO:77; the light chain CDR1 has the amino acid sequence of SEQ ID NO:83; the light chain CDR2 has the amino acid sequence of SEQ ID NO:87; and the light chain CDR3 has the amino acid sequence of SEQ ID NO:90.

In some cases, provided herein is an isolated antibody or fragment thereof, wherein the isolated antibody or fragment thereof binds to human nucleolin and comprises: the heavy chain CDR1 has the amino acid sequence of SEQ ID NO:70; the heavy chain CDR2 has the amino acid sequence of SEQ ID NO:74; the heavy chain CDR3 has the amino acid sequence of SEQ ID NO:78; the light chain CDR1 has the amino acid sequence of SEQ ID NO:84; the light chain CDR2 has the amino acid sequence of NVS; and the light chain CDR3 has the amino acid sequence of SEQ ID NO:90.

In some cases, provided herein is an isolated antibody or fragment thereof, wherein the isolated antibody or fragment thereof binds to human nucleolin and comprises: the heavy chain CDR1 has the amino acid sequence of SEQ ID NO:70; the heavy chain CDR2 has the amino acid sequence of SEQ ID NO:74; the heavy chain CDR3 has the amino acid sequence of AR; the light chain CDR1 has the amino acid sequence of SEQ ID NO:84; the light chain CDR2 has the amino acid sequence of NVS; and the light chain CDR3 has the amino acid sequence of SEQ ID NO:91.

In some cases, provided herein is an isolated antibody or fragment thereof, wherein the isolated antibody or fragment thereof binds to human nucleolin and comprises: a VH that has at least 60% sequence identity to an amino acid sequence of SEQ ID NO:17; and a VL that has at least 60% sequence identity to an amino acid sequence of SEQ ID NO:19. In some embodiments, the amino acid sequence of SEQ ID NO:17 is encoded by the nucleotide sequence of SEQ ID NO:16. In some embodiments, the amino acid sequence of SEQ ID NO:19 is encoded by the nucleotide sequence of SEQ ID NO:18. In some embodiments, the at least 60% sequence identity is at least: 65%, 70%, 75%, 80%, 85%, 90%, 95%, or 98%, or 100% sequence identity.

In some cases, provided herein is an isolated antibody or fragment thereof, wherein the isolated antibody or fragment thereof binds to human nucleolin and comprises: a VH has an amino acid sequence of SEQ ID NO:17; and a VL that has an amino acid sequence of SEQ ID NO:19.

In some cases, provided herein is an isolated antibody or fragment thereof that comprises any combination of a heavy chain CDR, VH, or fragment thereof disclosed herein and a light chain CDR, VL, or fragment thereof disclosed herein.

In some cases, provided herein is an isolated anti-nucleolin antibody or fragment thereof that binds to amino acid sequence SEQ ID NO:21. In some cases, provided herein is an isolated anti-nucleolin antibody or fragment thereof that binds to an epitope within residues G300 to E466 of amino acid sequence SEQ ID NO:20. In some embodiments, the epitope comprises an amino acid selected from the group consisting of E453, R457, D455, K348, K427, G426, K403, Y402, and any combination thereof. In some embodiments, the isolated antibody or fragment thereof comprises a light chain CDR1 that binds to E453, R457, or a combination thereof. In some embodiments, the isolated antibody or fragment thereof comprises a light chain CDR2 that binds to D455. In some embodiments, the isolated antibody or fragment thereof comprises a light chain CDR3 that binds to K348. In some embodiments, the isolated antibody or fragment thereof comprises a heavy chain CDR1 that binds to K427. In some embodiments, the isolated antibody or fragment thereof comprises a heavy chain CDR2 that binds to K427, G426, or a combination thereof. In some embodiments, the isolated antibody or fragment thereof comprises a heavy chain CDR3 that binds to K403, Y402, or a combination thereof. In some embodiments, the nucleolin is cell-surface nucleolin. In some embodiments, the isolated antibody or fragment thereof is human or humanized. In some embodiments, the isolated antibody or fragment thereof is an IgG antibody. In some embodiments, the isolated antibody or fragment thereof is an IgG1, IgG2, IgG3, or IgG4 antibody. In some embodiments, the isolated antibody or fragment thereof is a fragment that is a Fab fragment, a Fab' fragment, a F(ab')$_2$ fragment, a Fv fragment, a diabody, a linear antibody, a single-chain antibody, or a multispecific antibody formed from an antibody fragment. In some embodiments, the isolated antibody or fragment thereof is a fragment that comprises an antigen binding region. In some embodiments, the isolated antibody or fragment thereof is nontotoxic to normal cells or tissues. In some embodiments, the isolated antibody or fragment thereof is cytotoxic, e.g., to a tumor or cancer cell. In some embodiments, the isolated antibody or fragment thereof is cytotoxic in presence of human serum. In some embodiments, the isolated antibody or fragment thereof kills at least 10% of a population of tumor or cancer cells, when incubated with the population of tumor or cancer cells for a period of time. In some embodiments, the isolated antibody or fragment thereof kills at least: 20%, 30%, 40%, 50%, 60%, 70%, 80%, or 90%; or about 100% of the population of tumor or cancer cells. In some embodiments, the incubation is in presence of human serum. In some embodiments, the period of time is about 48-96 hours. In some embodiments, the tumor or cancer cell comprises one, two, or more types of cancer cells selected from the group consisting of human lung cancer, skin cancer, breast cancer, liver cancer, colon cancer, lung cancer, kidney cancer, prostate cancer, leukemia, brain cancer, and pancreas cancer cells. In some embodiments, the tumor or cancer cell comprises one, two, or more types of cancer cells selected from the group consisting of A549, A375, MCF-7, Hep3B, HCT-116, NCI-H358, 786-0, DU-145, MDA-MB-231, MV4-11, U251, CG-EMT, MIA-PaCa2, and PANC-1 cells. In some embodiments, the population of tumor or cancer cells comprises breast cancer cells, e.g., MCF-7 or MDA-MB-231 cells. In some embodiments, the population of tumor or cancer cells comprises acute myeloid leukemia (AML) cells, e.g., MV4-11 cells. In some embodiments, the population of tumor or cancer cells comprises prostate cancer cells, e.g., DU-145 cells, or CG-EMT cells. In some embodiments, the population of tumor or cancer cells comprises lung cancer cells, e.g., A549 or NCI-H358 cells. In some embodiments, the population of tumor or cancer cells comprises skin malignant melanoma cells, e.g., A375 cells. In some embodiments, the population of tumor or cancer cells comprises hepatocellular carcinoma cells, e.g., Hep3B cells. In some embodiments, the population of tumor or cancer cells comprises colon cancer cells, e.g., HCT-116 cells. In some embodiments, the population of tumor or cancer cells comprises renal cancer cells, e.g., 786-0 cells. In some embodiments, the population of tumor or cancer cells comprises brain tumor cells, e.g., U251 cells. In some embodiments, the population of tumor or cancer cells comprises pancreas carcinoma cells, e.g., MIA-Paca2 or PANC-1 cells.

In some cases, provided herein is a recombinant cell that produces an isolated antibody or fragment thereof disclosed herein. In some cases, provided herein is an isolated nucleic acid encoding an isolated antibody or fragment thereof disclosed herein. In some cases, provided herein is a vector that comprises a nucleic acid disclosed herein. In some cases, provided herein is a host cell that comprises a nucleic acid disclosed herein or a vector disclosed herein. In some cases, provided herein is a method of producing an antibody or fragment thereof that comprises culturing a host cell disclosed herein so that the antibody or fragment thereof is produced.

In some cases, provided herein is a pharmaceutical composition that comprises an effective amount of an isolated antibody or fragment thereof disclosed herein and a pharmaceutically acceptable carrier. In some embodiments, the isolated antibody or fragment thereof is a monoclonal antibody. In some embodiments, the isolated antibody or fragment thereof is a polyclonal antibody.

In some cases, provided herein is a method of treating a cancer, comprising administering to a subject in need thereof a pharmaceutical composition that comprises an isolated antibody or fragment thereof disclosed herein. In some embodiments, the administering is injection. In some embodiments, the administering is intravenous or subcutaneous injection. In some embodiments, the administering occurs 1-3 times per week. In some embodiments, the method reduces a size of tumor in the subject by at least: 10%, 15%, 20%, 25%, 30%, 35%, 40%, 45%, 50%, 55%, 60%, 65%, 70%, 75%, 80%, 85%, 90%, 95%, or 98%. In some embodiments, the tumor is a solid tumor. In some embodiments, the pharmaceutical composition is dosed from 0.15 mg to 3 mg per kg of body weight of the subject, e.g., 0.5 mg to 2 mg per kg of body weight of the subject. In some embodiments, the subject is a mammal, e.g., a human. In some embodiments, the cancer comprises one, two, or more types of cancer selected from the group consisting of human lung cancer, skin cancer, breast cancer, liver cancer, colon cancer, lung cancer, kidney cancer, prostate cancer, leukemia, brain cancer, and pancreas cancer.

In some cases, provided herein is a method of killing cancer cells, comprising contacting with the cancer cells an isolated antibody or fragment thereof disclosed herein. In some cases, provided herein is a use of an isolated antibody or fragment thereof disclosed herein for treating cancer or killing cancer cells.

In some cases, provided herein is a use of an isolated antibody or fragment thereof disclosed herein in the manufacture of a medicament. In some embodiments, the medicament is for treatment of a cancer. In some embodiments, the medicament is for killing cancer cells.

In some cases, provided herein is a recombinant mammalian cell line, wherein the recombinant mammalian cell line comprises one or more cells that comprise a first nucleic acid sequence of SEQ ID NO:1 and a second nucleic acid sequence of SEQ ID NO:10. In some embodiments, the first nucleic acid sequence and the second nucleic acid sequence are in a same construct. In some embodiments, the first nucleic acid sequence and the second nucleic acid sequence are recombinantly or synthetically produced and cloned into an expression vector. In some embodiments, the expression vector is a pTT5 expression vector. In some embodiments, the first nucleic acid sequence and the second nucleic acid sequence are transfected into the one or more cells.

In some cases, provided herein is a method of activating an immune system in a human subject, comprising administering to the subject an isolated antibody or fragment thereof disclosed herein. In some cases, provided herein is a method of treating cancer by inhibiting Transforming growth factor beta (TGFβ) in a human subject, comprising administering to the subject an isolated antibody or fragment thereof disclosed herein, whereby the TGFβ is inhibited and the cancer is treated. In some embodiments, the TGFβ is TGFβ1, TGFβ2, or TGFβ3.

In some cases, provided herein is a method of treating a cancer by preventing stabilization of an oncogenic mRNA in a human subject, comprising administering to the subject an isolated antibody or fragment thereof disclosed herein, whereby the oncogenic mRNA is destabilized and the cancer is treated. In some embodiments, the oncogenic mRNA is tumor protein p53 mRNA, B-cell lymphoma-extra large (Bcl-XL) mRNA, (B-cell lymphoma 2) Bcl-2 mRNA, gastrin mRNA, (growth arrest and DNA damage-inducible alpha) Gadd45α mRNA, matrix metallopeptidase 9 (MMP9) mRNA, *Arabidopsis thaliana* kinesin (Atk1) mRNA, Cyclin 1 mRNA, interleukin-2 (IL-2) mRNA, prostaglandin H synthase-1 (Pghs-1) mRNA, or any combination thereof. In some cases, provided herein is a method of treating a cancer by reducing an expression level of an oncogenic protein in a human subject, comprising administering to the subject an isolated antibody or fragment thereof disclosed herein, whereby the expression level of the oncogenic protein is destabilized and the cancer is treated. In some embodiments, the oncogenic protein is tumor protein p53, Bcl-xL, Bcl-2, gastrin, Gadd45a, MMP9, Atk1, Cyclin 1, IL-2, Pghs-1, or any combination thereof. In some embodiments, the cancer comprises one, two, or more types of cancers selected from the group consisting of human lung cancer, skin cancer, breast cancer, liver cancer, colon cancer, lung cancer, kidney cancer, prostate cancer, leukemia, brain cancer, and pancreas cancer.

In some cases, provided herein is an immunoconjugate, wherein the immunoconjugate comprises an antigen binding agent linked to a therapeutic agent, and wherein the antigen binding agent comprises an isolated antibody or fragment thereof disclosed herein. In some embodiments, the immunoconjugate is a fusion protein, and the therapeutic agent is a polypeptide. In some embodiments, the antigen binding agent is a bispecific antibody. In some embodiments, the antigen binding agent is a probody. In some embodiments, the probody comprises an antigen-binding region that is activated by a tumor cell. In some embodiments, the antigen-binding region comprises a peptide linked to the N-terminus of a light chain through a protease cleavable linker. In some embodiments, the antigen binding agent is linked covalently, noncovalently, or recombinantly to the therapeutic agent. In some embodiments, the therapeutic agent is a cytotoxic agent. In some embodiments, the cytotoxic agent is doxorubicin, calicheamicin, auristatin, maytansinoid, brentuximab vedotin, tubulysins, duocarmycins, camptothecin, SN-38, pyrrolobenzodiazepine, methotrexate, α-amanitin, ansamitocin, or any combination thereof. In some embodiments, the therapeutic agent is an immune stimulating agent. In some embodiments, the therapeutic agent is interleukin-2 (IL-2), an immunostimulatory nucleic acid molecule, granulocyte macrophage colony-stimulating factor, resiquimod, Gardiquimod, phycocyanobilin, romiplostim, eltrombopag, or any combination thereof.

In some cases, provided herein is a pharmaceutical composition that comprises an immunoconjugate disclosed herein and a pharmaceutically acceptable carrier. In some cases, provided herein is a method of treating a cancer, comprising administering to a subject in need thereof a pharmaceutical composition that comprises an immunoconjugate disclosed herein. In some cases, provided herein is a use of an immunoconjugate disclosed herein for treating a cancer. In some cases, provided herein is a use of an immunoconjugate disclosed herein in the manufacture of a medicament for treatment of a cancer.

BRIEF DESCRIPTION OF THE DRAWINGS

The following drawings form part of the present specification and are included to further demonstrate certain aspects of the present disclosure. The present disclosure may be better understood by reference to one or more of these drawings in combination with the detailed description of specific embodiments presented herein.

DETAILED DESCRIPTION

Figure 1:
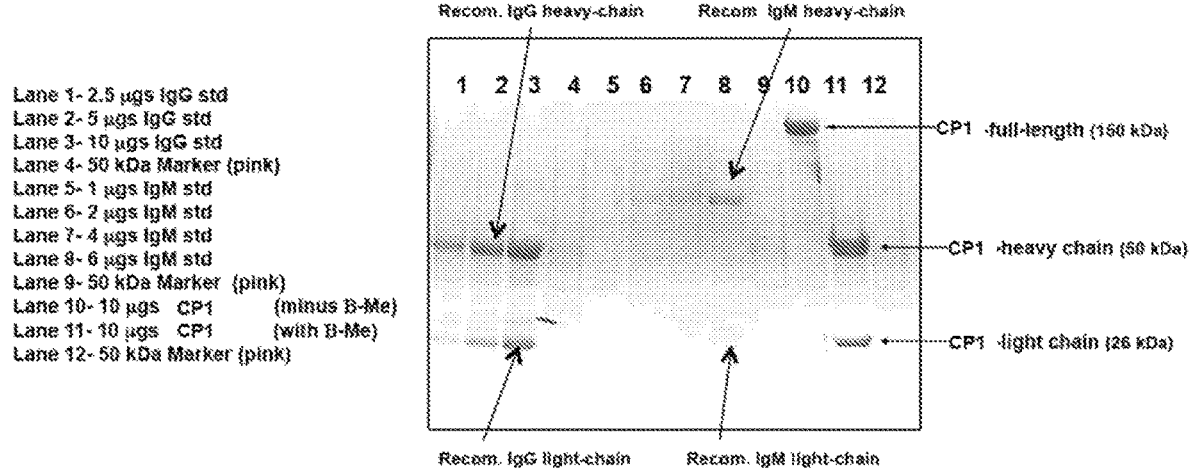
FIG. 1 is an image showing SDS PAGE gel of antibody CP1 and IgG and IgM standards. COOMASSIE blue staining of the SDS PAGE gel shows that in the absence of β-mercaptoethanol (lane 10), full length antibody CP1 has a molecular mass of about 150 KDa. Reduction of CP1 with β-mercaptoethanol (lane 11) reveals that the antibody is of class IgG with heavy- and light-chains of about 50 KDa and 26 KDa, respectively.
Figure 2:
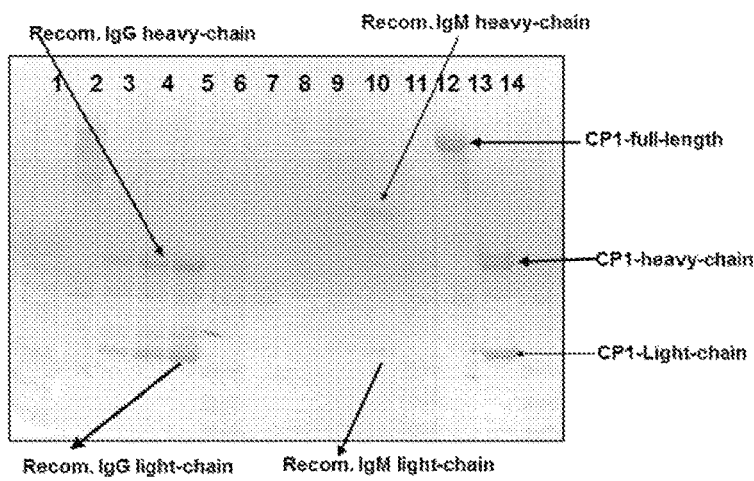
FIG. 2 is an image showing SDS PAGE gel of CP1 purified using MABSELECT 1.0 ml protein A column.
Figure 3:
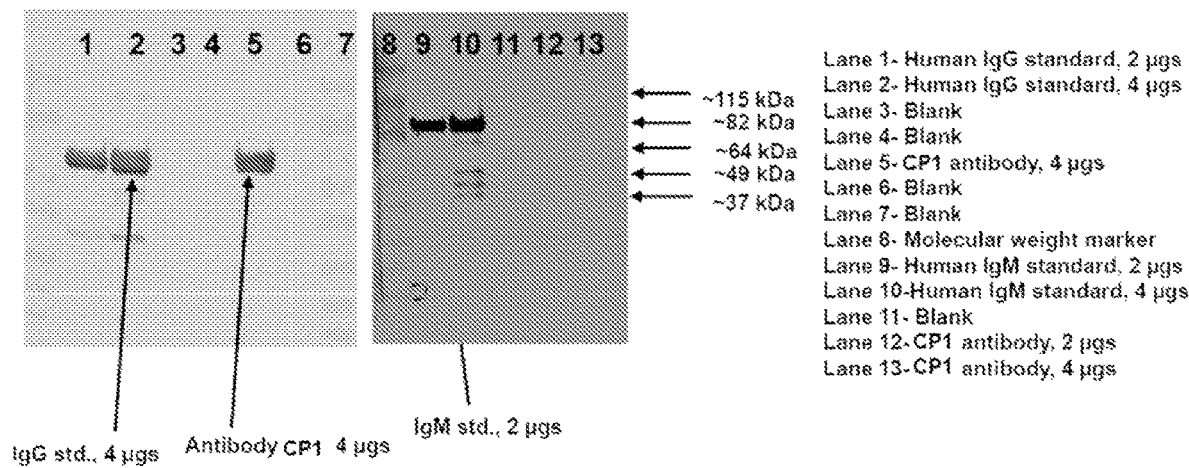
FIG. 3 is an image showing western blot analysis of CP1. SDS PAGE was done under reducing conditions with known amounts of antibody CP1 along with IgG1 and IgM standards. The transfer membrane was cut into two sections and one section was probed with a HRP-conjugated secondary antibody specific for human IgG1 (lanes 1-7) while the second section was probed with a HRP-conjugated secondary antibody specific for human IgM. Not Shown-Sequencing of the cDNAs of the heavy- and light-chains of CP1 revealed that the antibody is of subclass IgG1kappa.

The present disclosure provides anti-nucleolin antibodies and methods of use thereof. These antibodies exhibit cytotoxicity towards cells expressing nucleolin in the plasma membrane, such as cells involved in cancer, autoimmune disorders, and viral disorders. Therefore, the antibodies have therapeutic potential for certain forms of cancer, hyperproliferative and neovascular disorders and autoimmune diseases.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "about" means the referenced numeric indication plus or minus 15% of that referenced numeric indication.

In some aspects, the present disclosure provides immortalized B-cells, e.g., human B-cell s that express IgG antibodies that bind to and inactivate nucleolin. While these immortalized populations were found to express more than one antibody sequence, through the use of antibody sequencing technologies, the identity and amino acid sequence of the underlying antibodies were determined and can now be provided for use in the construction of immunological therapeutic reagents. Cell culturing was also used to isolate individual antibodies. Subsequently each isolated antibody was tested for potency and binding to cell surface nucleolin.

Provided herein is an isolated antibody or fragment thereof that can bind to nucleolin, comprising a heavy chain variable region (VH) that can comprise one or more complementarity determining regions (CDRs) each having at least 60% sequence identity to one or more corresponding VH CDRs in Table 7 or Table 8. A VH can comprise one CDR having at least 60% sequence identity to one or more corresponding VH CDR in Table 7 or Table 8. In some cases, a corresponding VH CDR can be CDR H1. In some cases, a corresponding VH CDR can be CDR H2. In some cases, a corresponding VH CDR can be CDR H3. In some aspects, a VH can comprise two CDRs each having at least 60% sequence identity to one or more corresponding VH CDRs in Table 7 or Table 8. In some aspects, the two corresponding VH CDRs can be CDR H1 and CDR H2. In some cases, the two corresponding VH CDRs can be CDR H1 and CDR H3. In some cases, the two corresponding VH CDRs can be CDR H2 and CDR H3.

Also provided herein is an antibody or fragment thereof, wherein a VH can comprise three CDRs each having at least 60% sequence identity to one or more corresponding CDR H1, CDR H2, or CDR H3 in Table 7. In some cases, an antibody or fragment thereof wherein the VH can comprise three CDRs having at least 60% sequence identity to corresponding CDR H1, CDR H2, and CDR H3 in Table 8. In some cases, an antibody or fragment thereof can comprise an amino acid sequence identity that can be at least: 65%, 70%, 75%, 80%, 85%, 90%, or 95%, or 100%.

Also provided herein is an isolated antibody or fragment thereof that binds to nucleolin, comprising a light chain variable region (VL) that comprises one or more complementarity determining regions (CDRs) having at least 60% sequence identity to one or more corresponding VL CDRs in Table 7 or Table 8. In some cases, aVL can comprise one CDR having at least 60% sequence identity to one or more corresponding VL CDR in Table 7 or Table 8. In some cases, a corresponding VL CDR can be CDR L1. In some cases, a corresponding VL CDR can be CDR L2. In some cases, a corresponding VL CDR can be CDR L3.

In some cases, a VL can comprise two CDRs each having at least 60% sequence identity to one or more corresponding VL CDRs in Table 7 or Table 8. In some cases, two corresponding VL CDRs can be CDR L1 and CDR L2. In some cases, two corresponding VL CDRs can be CDR L1 and CDR L3. In some cases, two corresponding VL CDRs can be CDR L2 and CDR L3. In some aspects, a VL can comprise three CDRs each having at least 60% sequence identity to corresponding CDR L1, CDR L2, or CDR L3 in Table 7. In some cases, a VL can comprise three CDRs each having at least 60% sequence identity to corresponding CDR L1, CDR L2, or CDR L3 in Table 8. In some aspects, an amino acid sequence identity can be at least: 65%, 70%, 75%, 80%, 85%, 90%, or 95%, or 100%.

Also provided herein is an isolated antibody or fragment thereof that binds to nucleolin, comprising a heavy chain variable region (VH) that comprises one or more complementarity determining regions (CDRs) each having at least 60% sequence identity to one or more corresponding VH CDRs in Table 7 or Table 8; and a light chain variable region (VL) that comprises one or more complementarity determining regions (CDRs) having at least 60% sequence identity to one or more corresponding VL CDRs in Table 7 or Table 8. In some cases, an isolated antibody or fragment thereof that binds to nucleolin, can comprise a VH that has at least 60% sequence identity to VH in Table 7. In some cases, an isolated antibody or fragment thereof that binds to nucleolin, can comprise a VL that has at least 60% sequence identity to VL in Table 7. In some cases, an isolated antibody or fragment thereof that binds to nucleolin, can comprise a VH that has at least 60% sequence identity to VH in Table 8. In some regards, an isolated antibody or fragment thereof that binds to nucleolin, can comprise a VL that has at least 60% sequence identity to VL in Table 8. In some cases, an antibody or fragment thereof can comprise any combination of one or more CDRs. In some cases, an antibody or fragment thereof can have an amino acid sequence identity that can be or can be at least: 65%, 70%, 75%, 80%, 85%, 90%, or 95%, or 100%.

In some cases, an antibody or fragment thereof disclosed herein comprises CDR H1 comprising an amino acid sequence in Table 7 or Table 8; CDR H2 comprising the amino acid sequence in Table 7 or Table 8; and/or CDR H3 comprising the amino acid sequence in Table 7 or Table 8. In some cases, an antibody or fragment thereof disclosed herein comprises CDR L1 comprising an amino acid sequence in Table 7 or Table 8; CDR L2 comprising the amino acid sequence in Table 7 or Table 8; and/or CDR L3 comprising the amino acid sequence in Table 7 or Table 8.

In some cases, a nucleolin disclosed herein can be a cell-surface nucleolin. In some cases, a nucleolin disclosed herein can mean a nucleolin fragment. In some cases, a nucleolin disclosed herein is a human nucleolin.

Also provided herein is an antibody or fragment thereof that can be human or humanized. An antibody or fragment thereof can be an IgG antibody. In some cases, an antibody or fragment thereof can be an IgG1, IgG2, IgG3, or an IgG4 antibody. In some cases, an antibody or fragment thereof can be a monoclonal antibody. In some cases, an antibody or fragment thereof is nontoxic. In some cases, an antibody or fragment thereof can be cytotoxic. In some cases, an antibody or fragment thereof can be cytotoxic to a tumor or cancer cell. In some cases, an antibody or fragment thereof can be cytotoxic in presence of human serum. In some cases, an antibody or fragment thereof can exhibit or induce complement-dependent cytotoxicity to a tumor or cancer cell. In some cases, an antibody or fragment thereof can exhibit or induce complement-independent cytotoxicity to a tumor or cancer cell.

In some cases, an antibody or fragment thereof can kill at least 10% of a population of tumor or cancer cells, when incubated with cells for a period of time. In some cases, an antibody or fragment thereof can kill at least: 20%, 30%, 40%, 50%, 60%, 70%, 80%, or 90% of the population of tumor or cancer cells. In some cases, an antibody or fragment thereof can kill about 100% of a population of tumor or cancer cells. In some cases, an antibody or fragment thereof can have a period of time is about 48-96 hours. In some cases, a period of time can be about 96 hours. In some cases, cells can be breast cancer cells. In some cases, cells can be MCF-7. In some cases, cells can be acute myeloid leukemia (AML) cells. In some cases, cells can be HCT-116, NCI-H358, DU-145, MDA-MB-231, MV4-11, MIA-PaCa2, or PANC-1 cells. In some cases, cells can be prostate cancer cells. In some cases, cells can be hormone-refractory prostate cancer cells. In some cases, cells can be CG-EMT cells. In some cases, an isolated monoclonal cytotoxic antibody or fragment thereof can bind to an epitope within residues #300 to #466 of nucleolin SEQ ID NO:20. In some embodiments, the epitope has/spans about: 5, 10, 15, 20, 25, 30, 35, 40, 45, 50, 60, 70, or 80 amino acids. In some cases, an isolated monoclonal cytotoxic antibody or fragment thereof can bind to an epitope comprising one or more amino acids selected from the group consisting of E453, R457, D455, K348, K427, G426, K403, and Y402. In some cases, an antibody or fragment thereof can comprise a VL CDR1 in Table 7 that binds to E453, R457, or a combination thereof. In some cases, an antibody or fragment thereof can comprise a VL CDR2 in Table 7 that can bind to D455. In some cases, an antibody or fragment thereof can comprise a VL CDR3 in Table 7 that can bind to K348. In some cases, an antibody or fragment thereof can comprise a VH CDR1 in Table 7 that can bind to K427. In some cases, an antibody or fragment thereof, can comprise a VH CDR2 in Table 7 that can bind to K427, G426, or a combination thereof. In some cases, an antibody or fragment thereof can comprise a VH CDR3 in Table 7 that binds to K403, Y402, or a combination thereof.

In some cases, an anti-nucleolin agent disclosed herein has a Kd of about: 10 µM, 1 µM, 0.1 µM, 0.05 µM, 10 nM, 5 nM, 2.5 nM, 1 nM, or less, to nucleolin or a fragment thereof, e.g., amino acid #300 to #466 (SEQ ID NO:21) or an epitope therein. In some embodiments, the Kd is about 2.5 nM or less.

In some cases, an antibody or fragment thereof can be an IgG antibody. In some cases, a fragment thereof can be a Fab, Fab', F(ab')$_2$, or Fv fragment; diabody; linear antibody; single-chain antibody; or a multispecific antibody formed from an antibody fragment. In some cases, a fragment thereof can comprise an antigen binding region thereof.

Also provided herein is a recombinant cell that can produce an antibody or fragment thereof. In some cases, a cell can be a B cell. In some cases, a cell can be a human B cell. In some cases, a cell can be a hybridoma.

Also provided herein is an isolated nucleic acid encoding an antibody or fragment thereof disclosed herein. In some cases, a vector can comprise a nucleic acid disclosed herein. In some cases, a host cell can comprise a vector disclosed herein.

Also provided herein is a method of producing an antibody or fragment thereof comprising culturing a host cell so that an antibody or fragment thereof can be produced.

Also provided herein is a pharmaceutical composition that comprises an antibody or fragment thereof and a pharmaceutically acceptable carrier. In some cases, an antibody or fragment thereof can be used as a medicament.

Also provided herein is a method of treating cancer with an antibody or fragment thereof. Also provided herein can be a method of killing cancer cells with an antibody or fragment thereof. Also provided herein can be a use of an antibody or fragment thereof treating cancer. In some cases, a use of an antibody or fragment thereof can be used for killing cancer cells. In some cases, a use of an antibody or fragment thereof can be for the manufacture of a medicament. A medicament can be for treatment of cancer. A medicament can be for killing cancer cells.

Also disclosed herein is a method for making an anti-cancer antibody or a fragment thereof, comprising: culturing a cell in a medium under conditions permitting expression of a polypeptide encoded by a vector and assembling of an antibody or fragment thereof; and purifying an antibody or fragment from cultured cell or medium of a cell.

In some cases, a recombinant mammalian cell line can be transfected with an antibody construct encoded by a first construct gamma heavy chain disclosed herein and a second construct kappa light chain disclosed herein. In some cases, a recombinant mammalian cell line can be transfected with an antibody construct encoded by a first construct gamma heavy chain disclosed herein and a second construct lambda light chain disclosed herein. In some cases, said heavy chain and said light chain are in the same construct. In some cases, antibody constructs can be synthetically produced and cloned into an expression vector pTT5. In some cases, cells can be maintained at a density of (0.25 to 5)×10$^6$ cells/mL.

In some cases, a cancer treated by an antibody or fragment thereof comprises one, two, three, four, five, or more types selected from the group consisting of human lung cancer, skin cancer, breast cancer, liver cancer, colon cancer, lung cancer, kidney cancer, prostate cancer, leukemia, brain cancer, and pancreas cancer.

In some cases, a cancer cell killed by an antibody or fragment thereof comprises one, two, three, four, five, or more types selected from the group consisting of human lung cancer, skin cancer, breast cancer, liver cancer, colon cancer, lung cancer, kidney cancer, prostate cancer, leukemia, brain cancer, and pancreas cancer cells. In some embodiments, the cancer cell comprises one, two, three, four, five, or more types selected from the group consisting of A549, A375, MCF-7, Hep3B, HCT-116, NCI-H358, 786-0, DU-145, MDA-MB-231, MV4-11, U251, CG-EMT, MIA-PaCa2, and PANC-1 cells.

1. NUCLEOLIN

1A. General

Nucleolin is a multi-functional protein that binds to DNA, RNA and the external surface of the plasma membrane. The ability of nucleolin to perform numerous and diverse functions within the cell is related to the multiple structural domains within the protein. Its negatively charged N-terminal domain regulates rDNA transcription by inducing nucleolar chromatin decondensation (Srivastava et al., 1989), while the central globular domain contains four RNA binding domains (RBDs) (Serin et al., 1997). It has been proposed that nucleolin, via binding of its RBD and its RGG-rich C-terminal domains to pre-ribosomal RNA, functions as an assembly factor by bringing together the correctly folded rRNA and other components necessary for rRNA maturation and ribosome assembly (Ginisty et al., 2001). Nucleolin may also be involved in exporting ribosomes to the cytoplasm while shuttling between the cytoplasm and nucleus (Srivastava and Pollard, 1999). The nucleolin gene coding and protein sequences can be accessed at accession number NM_005381, XM_002342275, NP_005372 and XP_002342316. Nucleolin is also known as C23, FLJ45706, FLJ59041, and NCL.

Human NCL gene consists of 14 exons with 13 introns and spans approximately 11 kb. The nucleolin protein contains several functional domains that mediate its functions. The N-terminal part contains multiple phosphorylation sites and is rich in acidic amino acids. The central part of nucleolin includes four RNA binding domains (RBD) and the C-terminal part contains glycine and arginine rich domain (termed RGG or GAR domain). (Farin et al., 2009)

A considerable body of evidence supports a role for nucleolin in mRNA stabilization. Nucleolin binds to the 3'-untranslated region (3'-UTR) of amyloid precursor protein mRNA and stabilizes this mRNA (Westmark and Malter, 2001). It is also required for the stabilization of IL-2 mRNA that occurs during T cell activation (Chen et al., 2000).

Nucleolin is present on the external surface of various types of tumor cells Otake et al., 2007; Soundararaj an et al., 2008; Chen et al., 2008; Hovanessian et al., 2000; Sinclair and O'Brien, 2002), despite its lack of a transmembrane domain or signal sequence (Srivastava et al., 1989; Lapeyre et al., 1987). Results show that nucleolin is not secreted from either MV4-11 cells or K-562 cells into the tissue culture medium (Soundararaj an et al., 2009). This suggests that the presence of nucleolin on the cell surface is not the result of adsorption of secreted nucleolin by macromolecules on the cell surface of tumor cells. However, nucleolin undergoes extensive posttranslational modification (Srivastava et al., 1989; Lapeyre et al., 1987). It has been isolated as a glyco-phospho-protein from the surface of various types of proliferating cells (Hovanessian et al., 2000; Pfeifle and Anderer, 1983). It is also possible that palmitoylation, prenylation, or myristoylation of nucleolin may allow for insertion or anchoring of these hydrophobic regions of the protein into the plasma membrane. It is thought that nucleolin functions as a shuttling protein between the plasma membrane and nucleus (Hovanessian et al., 2000). In proliferating tumor cells, nucleolin is often associated with endocytotic vesicles that invaginate from the plasma membrane (Hovanessian et al., 2000). Nucleolin also acts as a cell surface receptor for various ligands, since ligands bound to nucleolin within these vesicles become internalized in a temperature-dependent process. For example, plasma membrane nucleolin has been reported to function as a receptor for intimin-γ of *E. coli* (Sinclair and O'Brien, 2002), the anti-HIV agent midkine (Said et al., 2002), laminin-1 (Kibbey et al., 1995), DNA nanoparticles (Chen et al., 2008), and the anti-angiogenic pseudopeptide HB-19 (Destouches et al., 2008). Nucleolin is an important protein in the nucleolus involved in ribosome biogenesis and maturation in exponentially growing eukaryotic cells. In this regard, one important function of nucleolin is as a shuttling protein between cytoplasm and nucleus involving RNA processing and other cell biological process. While in normal cellular physiology, nucleolin is localized predominantly in the nucleolus and cytoplasm, under certain conditions, especially in various disease states it has also been shown to be present in a phosphorylated form on the cell surface. In this regard, nucleolin in the cell membrane serves as a binding protein for a variety of ligands that drive cell proliferation, differentiation, adhesion, mitogenesis and angiogenesis.

1B. Nucleolin in Cancer

Several lines of evidence suggest that nucleolin is an excellent tumor antigen for antibody-based immunotherapy. Nucleolin is overexpressed in the plasma membrane and cytoplasm a variety of human tumors including human chronic lymphocytic leukemia (CLL) (Otake et al., 2007), acute myeloid leukemia (AML) (Soundararaj an et al., 2008), and breast cancer cells (Soundararaj an et al., 2008), but not in normal CD19+ B cells (Otake et al., 2007), CD33+ myeloid cells (Gattoni-Celli et al., 2009), nor in normal mammary epithelial cells (Soundararaj an et al., 2008). It is of interest that AML blast cells from patients that engraft in NOD/SCID mice show intense nucleolin staining in the plasma membrane and cytoplasm while the normal mouse bone marrow cells and spleen lymphocytes were negative for nucleolin (Gattoni-Celli et al., 2009). In normal human myeloid cells, nucleolin staining is concentrated in nucleoli, while in patient AML-1 cells extensive nucleolin staining (aberrant expression of nucleolin) was observed in nuclei and in the cytoplasm/cell surface.

The nucleolin targeting aptamer, AS1411, targets nucleolin. Plasma membrane nucleolin was recently reported to be a receptor for AS1411 in human MV4-11 leukemia cells (Soundararaj an et al., 2009).

AS1411 binds to nucleolin that is overexpressed on the external surface of tumor cells and gains intracellular access when nucleolin is shuttled from the plasma membrane to the cytoplasm and nucleus. AS1411 has been shown to exhibit antiproliferative activity in a broad set of cancer cell lines that over-express nucleolin (Table 1).

TABLE 1

Cancer Cell Lines That Over-express Nucleolin and/or are Killed Subsequent to Nucleolin Inhibition

| Cancer Type: | Cell Line: |
|---|---|
| Lung cancer | A549, NCI-H322M, NCI-H460, EKVX, HOP-92, NCI-H299, CaLu1, NCI-H1385, NCI-H82, CaLu6 |
| Breast cancer | MCF7, T-47D, BT-549, MDA-N, MDA-MB-231, ZR7S-1 |
| Prostate cancer | DU145, PC-3, CA-HPV-10 |
| Colon cancer | HCC 2998, HT-29, KM12, HCT-116, SW620, HCT-15, LS174T |
| Pancreatic cancer | PANC-1, MIA-PaCa-2 |
| Renal cell carcinoma | 786-0, CAKI-1, RXF393, TK10, A498, ACHN, SN12C |
| Ovarian cancer | IGROV, OVCAR-3, OVCAR-4, OVCAR-5 |
| Cervical cancer | HeLa |
| Leukemia & Lymphoma | CCRF-CEM, SR, HL60, K-562, RPMI-6226, U937, Meg0, MV4-11 |
| Melanoma | LOX-IMVI, SK-MEL-2, A375, SK-MEL-28, MDA-MB-435 |
| Glioblastoma | SF-268, U87-MG |
| Neuroblastoma | IMR 32, Lan 5 |
| Sarcoma | HT-1080 |
| Gastric cancer | KATOIII, HGC27 |

Anti-nucleolin antibodies can also exploit the shuttling function of plasma membrane nucleolin and become internalized after binding to cell surface nucleolin. This suggests that anti-nucleolin antibodies can elicit anti-tumor effects through intracellular mechanisms, and/or to antibody-dependent cellular cytotoxicity (ADCC) and complement-dependent cellular cytotoxicity (CDCC).

1C. Antibodies or Fragments Thereof

In some embodiments, any of the methods disclosed herein can be practiced with an anti-nucleolin antibody or fragment thereof. In some embodiments an anti-nucleolin antibody or fragment thereof is used to detect a cell expressing nucleolin on its surface. In some embodiments, an anti-nucleolin antibody or fragment thereof is used to inhibit or kill a cell expressing nucleolin on its surface. In some embodiments, an anti-nucleolin antibody or fragment thereof is used to treat or prevent a neoplastic disease (e.g., cancer), an autoimmune disease, an inflammatory disease or condition, a respiratory disease, a viral infection, or macular degeneration.

In some embodiments, an anti-nucleolin antibody or fragment thereof is conjugated, linked or fused to a toxin, chemotherapeutic, an immunostimulatory nucleic acid sequence (e.g., a CpG sequence), a radionuclide or an immunotherapeutic. In some embodiments, an anti-nucleolin antibody or fragment thereof is conjugated, linked or fused to a radionuclide, a fluorophore, a chemiluminescent compound, a fluorescent compound, or an enzyme. In some embodiments, anti-nucleolin antibody or fragment thereof is used to contact a cell expressing nucleolin on its surface. In some embodiments the cell is pre-cancerous cell, a cancer cell or an immune cell.

In some embodiments, the anti-nucleolin antibody fragment thereof is a human anti-nucleolin antibody or fragment. In some embodiments the anti-nucleolin antibody fragment thereof is a non-human anti-nucleolin antibody fragment thereof. In some embodiments the anti-nucleolin antibody fragment thereof is a chimeric anti-nucleolin antibody fragment thereof. In some embodiments the anti-nucleolin antibody fragment thereof is a humanized anti-nucleolin antibody fragment thereof.

In some embodiments, an anti-nucleolin antibody fragment thereof is generated from an anti-nucleolin antibody. In some embodiments the anti-nucleolin antibody fragment has the same binding specificity to nucleolin as the parent antibody. In some embodiments, the anti-nucleolin antibody fragment has improved binding specificity to nucleolin as the parent antibody. In some embodiments the anti-nucleolin antibody fragment has the same binding affinity to nucleolin as the parent antibody. In some embodiments, the anti-nucleolin antibody fragment has improved affinity to nucleolin as the parent antibody. In some embodiments an anti-nucleolin antibody or fragment thereof is an anti-nucleolin antibody (e.g., human and/or monoclonal) fragment.

"Antibody fragments" comprise a portion of an intact antibody, or the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is a minimum antibody fragment which contains a complete antigen-binding site. In some embodiments, a two-chain Fv species consists of a dimer of one heavy- and one light-chain variable region in tight, non-covalent association. In a single-chain Fv (scFv) species, one heavy- and one light-chain variable region can be covalently linked by a flexible peptide linker such that the light and heavy chains can associate in a "dimeric" structure analogous to that in a two-chain Fv species. It is in this configuration that the three HVRs of each variable region interact to define an antigen-binding site on the surface of the VH-VL dimer. Collectively, the six HVRs confer antigen-binding specificity to the antibody. However, even a single variable region (or half of an Fv comprising only three HVRs specific for an antigen) has the ability to recognize and bind antigen, although at a lower affinity than the entire binding site.

The Fab fragment contains the heavy- and light-chain variable regions and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab').sub.2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthun, in The Pharmacology of Monoclonal Antibodies, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable region (VH) connected to a light-chain variable region (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., Nat. Med. 9:129-134 (2003); and Hollinger et al., PNAS USA 90: 6444-6448 (1993). Triabodies and tetrabodies are also described in Hudson et al., Nat. Med. 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of B cell or hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence can also be a monoclonal antibody. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations can be advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma or B cell method (e.g., Kohler and Milstein, Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, PNAS USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., PNAS USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and U.S. Pat. No. 5,661,016; Marks et al, Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The modifier "polyclonal" indicates the character of the antibody as being obtained from a source of a nonhomogeneous population of antibodies. A polyclonal antibody comprises more than one antibody, such as 1, 2, 3, 4, 5, 6, 7, 8, 9, or 10 antibodies.

The monoclonal antibodies herein include human, non-human, humanized and "chimeric" antibodies. "Chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816, 567; and Morrison et al., PNAS USA 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable regions, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., PNAS USA, 103:3557-3562 (2006) regarding human antibodies generated via a human B-cell hybridoma technology.

2. CLONING AND EXPRESSION OF IG LIGHT AND HEAVY CHAINS

Various methods can be employed for the cloning and expression of immunoglobulin light and heavy chain sequences. Weltschof et al. (1995), incorporated herein by reference, describes in detail the methods here. The variable regions, or variable+constant regions, can be cloned.

In some embodiments, these antibodies can be prepared by a technique described in WO 2011/062997 (incorporated herein by reference in its entirety) that permits one to directly identify, isolate and characterize, for example in terms of amino acid sequence, human anti-nucleolin antibodies from immortalized antibody-producing cells prepared using human immune cells such as tonsil cells.

Some techniques, such as those described by Takekoshi et al. (2001), are also useful. In that reference, total cellular RNA was isolated from pelleted cells using a commercial kit (RNeasy mini kit, Qiagen). Using random 9-mers, nucleotides and reverse transcriptase (Takara, RNA-PCR kit, Ohtsu), cDNAs were synthesized and were amplified by the polymerase chain reaction (PCR), with heavy and light chain primers specific for immunoglobulins (Ig). A "touchdown" PCR protocol was employed, i.e., three cycles each of denaturation at 95° C. for 1 min, annealing for 1 min, and elongation at 72° C. for 2 min, for a total of 11 cycles. The annealing temperature was varied from 65-55° C. in steps of 1° C. The touchdown cycles were followed by 25 cycles using an annealing temperature of 55° C. The resultant PCR product was gel-purified in agarose and extracted using QIAQUICK spin-columns (Qiagen). The light chain and heavy chain Fc genes were then cloned into the NheI/AscI and the SfiI/NotI sites of the expression vector pFab1-His2. The ligated pFab1-His2 vectors with the light chain (κ and λ) and Fc heavy chain genes (γ and μ) were introduced into competent *E. coli* JM109 cells (Toyobo, Osaka). After transformation, the *E. coli* cells were plated onto Luria-Bertani (LB)/ampicillin (50 μg/ml) plates. Isolated bacterial colonies were incubated at 30° C. in 2 ml of Super Broth (SB) with ampicillin (50 μg/ml) and $MgCl_2$ (1.5 mM). Isopropyl-β-D-thiogalactopyranoside (IPTG) was used to induce production of the Fab protein. Cells from the bacterial cultures were pelleted, resuspended in 0.3 ml of B-PER (Pierce) with a protease inhibitor cocktail (Complete, Boehringer Mannheim), and shaken for 5 min at room temperature. Cell lysates were centrifuged at 15,000G for 10 min, and the resultant supernatant containing the Fab antibody portion was collected.

In some embodiments, a heavy chain and a light chain can be in the same cloning construct. In some embodiments, a heavy chain and a light chain are found in different cloning constructs. Constructs containing sequences for heavy chain genes, light chain genes, or any combination thereof may be cloned simultaneously. Simultaneous cloning can comprise a vector containing both heavy and light chain genes or two separate vectors introduced simultaneously, each containing either a heavy chain or light chain. In some embodiments, constructs containing sequences for heavy chain genes, light chain genes, or any combination thereof may be cloned sequentially. Sequential cloning may comprise introducing a vector containing a heavy chain gene followed by the introduction of a second vector containing a light chain gene. For example, a cell can be genetically modified with a vector containing gene sequences for both a heavy chain and light chain.

3. ANTIBODY PRODUCTION

Once cloned, the nucleic acids for the light and heavy chains can be inserted into appropriate expression vectors and transferred into host cells (e.g., antibody-producing cells) that support production of antibodies. Exemplary cell lines for production are 293 cells, CHO cells, COS cells or various forms of myeloma cells, some lacking IgG. These cells can be exploited for antibodies (e.g., human and/or monoclonal) production in two basic ways. First, myelomas or immortalized cells can be injected (often into the peritoneal cavity) into a histocompatible animal of the type that was used to provide the somatic and myeloma cells for the original fusion (e.g., a syngeneic mouse), or into an immunodeficient animal for injection of incompatible cells. Optionally, the animals are primed with a hydrocarbon, especially oils such as pristane (tetramethylpentadecane) prior to injection. The injected animal develops tumors secreting the specific monoclonal antibody produced by the transfected myeloma. The body fluids of the animal, such as serum or ascites fluid, can then be tapped to provide antibodies (e.g., human and/or monoclonal) in high concentration. Second, the individual cell lines could be cultured in vitro, where the antibodies (e.g., human and/or monoclonal) are naturally secreted into the culture medium from which they can be readily obtained in high concentrations.

Antibodies (e.g., human and/or monoclonal) produced by either means can be further purified, if desired, using ultra filtration, centrifugation and various chromatographic methods such as HPLC, affinity chromatography, or ion exchange chromatography. Fragments of the monoclonal antibodies of the present disclosure can be obtained from the monoclonal antibodies so produced by methods which include digestion with enzymes, such as pepsin or papain, and/or by cleavage of disulfide bonds by chemical reduction.

In some embodiments, an anti-nucleolin antibody (e.g., human and/or monoclonal) is produced from an immortalized B cell (e.g., human B cell). In some embodiments an anti-nucleolin antibody (e.g., human and/or monoclonal) is produced using a method such as one set forth in PCT/US2008/072124 or U.S. patent application Ser. No. 12/671,936, which are herein incorporated by reference in their entirety.

In some embodiments, the cDNA of an isolated anti-nucleolin antibody (e.g., human and/or monoclonal) may be produced by cloning cDNA or genomic DNA encoding the immunoglobulin light and heavy chains of the anti-nucleolin antibody from a hybridoma cell (by fusing a specific antibody-producing B cell with a myeloma) that produces an antibody homolog. In some embodiments, an isolated anti-nucleolin antibody (e.g., human and/or monoclonal) is produced by a B cell (e.g., human B cell). In some embodiments, a cell is transfected by one or more polynucleotide sequences isolated from a B cell (e.g., human B cell) where the polynucleotide sequence encodes for anti-nucleolin antibody (e.g., human and/or monoclonal). The cDNA or genomic DNA encoding the polypeptides can be inserted into expression vectors so that both genes are operatively linked to their own transcriptional and translational expression control sequences. The expression vector and expression control sequences can then be chosen to be compatible with the expression host cell used. In some embodiments, separate expression vectors are used for the heavy and light antibody chains.

Prokaryotic or eukaryotic cells can be used as expression hosts. Expression in eukaryotic host cells may be suitable because such cells are more likely than prokaryotic cells to assemble and secrete a properly folded and immunologically active antibody. However, any antibody produced that is inactive due to improper folding may be renaturable according to well known methods (Kim and Baldwin, 1982). It is possible that the host cells will produce portions of intact antibodies, such as light chain dimers or heavy chain dimers, which also are antibody homologs according to the present disclosure.

It will be understood that variations on the above procedure are within the scope of the present disclosure. In some embodiments, a host cell is transformed with DNA encoding either the light chain or the heavy chain (but not both) of an antibody homolog. Recombinant DNA technology may also be used to remove some or all of the DNA encoding either or both of the light and heavy chains that is not necessary for nucleolin binding. The molecules expressed from such truncated DNA molecules are antibody homologs. In some embodiments, bifunctional antibodies are produced in which one heavy and one light chain are homologs of an anti-nucleolin antibody (e.g., human and/or monoclonal) and the other heavy and light chain are specific for an antigen other than nucleolin, or another epitope of nucleolin.

In some embodiments, DNA encoding an isolated anti-nucleolin antibody (e.g., human and/or monoclonal) is transferred to a mammalian cell line for expression in "production" or commercial amounts. It has long been recognized that Chinese Hamster Ovary cells (CHO cells) make excellent expression vehicles for recombinant or non-endogenous DNA. See U.S. Pat. No. 4,816,567. There has been developed a series of DHFR deficient CHO cell strains, which permit the amplification of inserted DNA encoding specific proteins or DNA sequences, as set forth in U.S. Pat. No. 5,981,214. Examples of additional mammalian cell lines for expression in "production" or commercial amounts include, but are not limited to 293HEK cells, HeLa cells, COS cells, NIH3T3 cells, Jurkat cells, NSO cells and HUVEC cells. Other mammalian cell lines suitable for the expression of recombinant proteins have been identified in the literature, and can be equally suitable for use in the present disclosure of this application.

4. MODIFICATIONS OF ANTIBODIES

In some embodiments, amino acid sequence variants of the antibodies provided herein are contemplated. A variant typically differs from a polypeptide specifically disclosed herein in one or more substitutions, deletions, additions and/or insertions. Such variants can be naturally occurring or can be synthetically generated, for example, by modifying one or more of the above polypeptide sequences and evaluating one or more biological activities of the polypeptide as described herein and/or using any of a number of techniques well known in the art. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding and/or potency.

In some embodiments, antibody variants having one or more amino acid substitutions are provided. Sites of interest for mutagenesis by substitution include the CDRs and Frameworks (FRs). Amino acid substitutions may be introduced into an antibody of interest and the products screened for a desired activity, e.g., retained/improved antigen binding, decreased immunogenicity, or improved ADCC or CDC. Non-limiting examples of amino acid substitutions are shown in Table 2.

TABLE 2

Examples of Amino Acid Substitutions.

| Original Residue | Exemplary Conserved Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |

TABLE 2-continued

Examples of Amino Acid Substitutions.

| Original Residue | Exemplary Conserved Substitutions |
|---|---|
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Hydrophobic amino acids include: Norleucine, Met, Ala, Val, Leu, and Ile. Neutral hydrophilic amino acids include: Cys, Ser, Thr, Asn, and Gln. Acidic amino acids include: Asp and Glu. Basic amino acids include: His, Lys, and Arg. Amino acids with residues that influence chain orientation include: Gly and Pro. Aromatic amino acids include: Trp, Tyr, and Phe.

In some embodiments, substitutions, insertions, or deletions, e.g., by 1, 2, 3, 4, 5, 6, 7, 8, 9, or 10 amino acids, may occur within constant regions or one or more CDRs, wherein the substitutions, insertions, or deletions do not substantially reduce antibody binding to antigen. For example, conservative substitutions that do not substantially reduce binding affinity may be made in CDRs. Such alterations may be outside of CDR "hotspots" or SDRs. In some embodiments of the variant VH and VL sequences, each CDR either is unaltered, or contains no more than one, two or three amino acid substitutions.

Alterations (e.g., substitutions) may be made in CDRs, e.g., by 1, 2, 3, 4, 5, 6, 7, 8, 9, or 10 amino acids, to improve antibody affinity. Such alterations may be made in CDR encoding codons with a high mutation rate during somatic maturation (See, e.g., Chowdhury, Methods Mol. Biol. 207: 179-196 (2008)), and the resulting variant can be tested for binding affinity. Affinity maturation (e.g., using error-prone PCR, chain shuffling, randomization of CDRs, or oligonucleotide-directed mutagenesis) can be used to improve antibody affinity (See, e.g., Hoogenboom et al. in Methods in Molecular Biology 178:1-37 (2001)). CDR residues involved in antigen binding may be specifically identified, e.g., using alanine scanning mutagenesis or modeling (See, e.g., Cunningham and Wells Science, 244:1081-1085 (1989)). CDR-H3 and CDR-L3 are often targeted. In some embodiments, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions and deletions include amino- and/or carboxyl-terminal fusions ranging in length from one residue to polypeptides containing a hundred or more residues, as well as intrasequence insertions and deletions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody. Examples of intrasequence insertion variants of the antibody molecules include an insertion of 3 amino acids in the light chain. Examples of terminal deletions include an antibody with a deletion of 7 or less amino acids at an end of the light chain.

In some embodiments, an anti-nucleolin antibody may be formulated as immunoliposomes. Liposomes containing the antibody are prepared by methods known in the art, such as described in Epstein et al. (1985); Hwang et al. (1980); and U.S. Pat. Nos. 4,485,045 and 4,544,545. Liposomes with enhanced circulation time are disclosed in U.S. Pat. No. 5,013,556.

Useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al. (1982) via a disulfide interchange reaction. A chemotherapeutic agent (such as Doxorubicin) is optionally contained within the liposome. See Gabizon et al. (1989).

In some embodiments, an anti-nucleolin antibody is used in ADEPT by conjugating the antibody to a prodrug-activating enzyme which converts a prodrug (e.g., a peptidyl chemotherapeutic agent, see WO 81/01145) to an active drug. See, for example, WO 88/07378 and U.S. Pat. No. 4,975,278. The enzyme component of the immunoconjugate useful for ADEPT includes any enzyme capable of acting on a prodrug in such a way so as to convert it into its more active form exhibiting the desired biological properties.

Enzymes that can be useful include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. In some embodiments, antibodies with enzymatic activity, also known in the art as "abzymes," can be used to convert the prodrugs of the present disclosure into free active drugs (see, e.g., Massey, 1987). Antibody-abzyme conjugates can be prepared as described herein for delivery of the abzyme to a desired cell population.

The enzymes can be covalently bound to the anti-nucleolin antibodies by techniques well known in the art such as the use of the heterobifunctional crosslinking reagents discussed above. In some embodiments, fusion proteins comprising at least the antigen binding region of an antibody of the present disclosure linked to at least a functionally active portion of an enzyme of the present disclosure can be constructed using recombinant DNA techniques well known in the art (see, e.g., Neuberger et al., 1984).

In some embodiments, an anti-nucleolin antibody comprises an antibody fragment, rather than an intact antibody. In this case, the antibody fragment may be modified in order to increase its serum half-life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See WO 96/32478 published Oct. 17, 1996.

The salvage receptor binding epitope generally constitutes a region wherein any one or more amino acid residues from one or two loops of an Fc domain are transferred to an analogous position of the antibody fragment. For example, three or more residues from one or two loops of the Fc domain are transferred. For example, the epitope is taken from the CH2 domain of the Fc region (e.g., of an IgG) and transferred to the CH1, CH3, or VH region, or more than one such region, of the antibody. For example, the epitope is taken from the CH2 domain of the Fc region and transferred to the CL region or VL region, or both, of the antibody fragment.

In some embodiments, an anti-nucleolin antibody is modified by covalent linkages. Covalent linkages may include but are not limited to by chemical synthesis or by enzymatic or chemical cleavage of the antibody. Other types of covalent modifications of the antibody are introduced into the molecule by reacting targeted amino acid residues of the antibody with an organic derivatizing agent that is capable of reacting with selected side chains or the N- or C-terminal residues. Exemplary covalent modifications of polypeptides are described in U.S. Pat. No. 5,534,615, specifically incorporated herein by reference. One type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

In some embodiments, an anti-nucleolin antibody (such as a human antibody) is modified by conjugating it to another, heterologous polypeptide or amino acid sequence. In some embodiments, an anti-nucleolin antibody (such as a human antibody) is modified to comprise targeted immunoconjugate moieties which enable the effective generation of innate and adaptive immune responses against tumors or pathogens. In some embodiments, an isolated anti-nucleolin antibody (e.g., human and/or monoclonal) is modified to comprise targeted immunoconjugate moieties which enable the effective generation of innate and adaptive immune responses against tumors or pathogens. In some embodiments, an isolated anti-nucleolin antibody (e.g., human and/or monoclonal) produced by a B cell (e.g., human B cell) is modified to comprise targeted immunoconjugate moieties which enable the effective generation of innate and adaptive immune responses against tumors or pathogens. The immunoconjugates can be capable of simultaneously satisfying multiple key requirements for mounting effective antibody- and/or cell-mediated immune responses against the targeted tumor or pathogen, which include but are not limited to: (i) Inducing or augmenting uptake and cross-presentation of tumor- or pathogen antigen(s) or antigenic determinant(s) by antigen presenting cells (APC)/dendritic cells (DC); (ii) promoting the maturation of dendritic cells (DCs) in the target cell milieu; (iii) providing CD4+ T cell help to generate CD8+ T cell memory and antibodies against the tumor or pathogen; (iv) sensitizing the targeted tumor cell to antibody dependent cell cytotoxicity (ADCC) and T-cell mediated death. Such immunoconjugated antibodies can be used for targeted immunotherapy or immunoprophylaxis of neoplastic diseases, infectious diseases, and other disorders. For example, pattern recognition receptors (PRRs), such as Toll like Receptors, recognize pathogen-associated molecular patterns (PAMPs) expressed by diverse infectious microorganisms (bacteria, fungi, protozoa, viruses) and molecules released by damaged host tissues (damage associated molecular patterns/alarmins). The addition of a PAMP conjugated to an isolated anti-nucleolin antibody (e.g., human and/or monoclonal) provides a moiety comprising a nucleic acid or protein that is recognized by a PRR, ultimately leading to an immune response which eliminates the target cell with the anti-nucleolin antibody bound to it. Examples of PAMPS that can be conjugated to an anti-nucleolin antibody include but are limited to known viral and pathogenic epitopes, such as polyinosine-polycytidylic acid, lipopolysaccharide (LPS), lipid A, flagellin, GU-rich short single-stranded RNA, unmethylated CpG-oligodeoxynucleotides.

In some embodiments, an anti-nucleolin antibody (such as a human antibody) is modified by fusing, or conjugating it to another, heterologous polypeptide or amino acid sequence. In some embodiments an anti-nucleolin antibody (such as a human antibody) is fused or conjugated with a tag polypeptide which provides an epitope to which an anti-tag antibody can selectively bind. The epitope tag can be placed at the amino- or carboxyl-terminus of the anti-nucleolin antibody. The presence of such epitope-tagged forms of an anti-nucleolin antibody can be detected using an antibody against the tag polypeptide. Also, provision of the epitope tag enables the anti-nucleolin antibody to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag and its antibody 12CA5 (Field et al., 1988); the c-myc tag and the 8F9, 3C7, 6E10, G4, B7 and 9E10 antibodies thereto (Evan et al., 1985); and the Herpes Simplex virus glycoprotein D (gD) tag and its antibody (Paborsky et al., 1990). Other tag polypeptides include the Flag-peptide (Hopp et al., 1988); the KT3 epitope peptide (Martin et al., 1992); an a-tubulin epitope peptide (Skinner et al., 1991); and the T7 gene 10 protein peptide tag (Lutz-Freyermuth et al., 1990).

In some embodiments, an anti-nucleolin antibody (e.g., human and/or monoclonal) or fragment is linked to a nanoparticle. In some embodiments, an isolated anti-nucleolin antibody (e.g., human and/or monoclonal) is linked to a nanoparticle. In some embodiments, an anti-nucleolin antibody (e.g., human and/or monoclonal) produced by a B cell (e.g., human B cell) is linked to a nanoparticle. Cell surface nucleolin has been reported to serve as receptor for DNA nanoparticles composed of PEGylated polylysine and DNA (Chen et al., 2008). In some embodiments, the antibody-nanoparticle conjugate can penetrate a cell expressing nucleolin on its surface more rapidly and extensively than the unconjugated antibody. In some embodiments, the cell is a cancer cell, tumor cell, virally infected cell, lymphocyte, or activated lymphocyte.

5. THERAPEUTIC USE

5.1. Anti-Nucleolin Antibodies

In some embodiments, an anti-nucleolin antibody (e.g., human and/or monoclonal) is provided that can be used to inhibit or kill a cancer cell. In some embodiments, an isolated anti-nucleolin antibody (e.g., human and/or monoclonal) is provided that can be used to inhibit or kill a cancer cell. In some embodiments, an isolated anti-nucleolin antibody (e.g., human and/or monoclonal) expressed by a B cell (e.g., human B cell) is provided that can be used to inhibit or kill a cancer cell. In some embodiments the cancer cell expresses nucleolin on its surface or in it cytoplasm. Examples of cancer cells that can be inhibited or killed by an anti-nucleolin antibody (e.g., human and/or monoclonal) are described hereinbelow.

In some embodiments, an anti-nucleolin antibody (e.g., human and/or monoclonal) is used to reduce cell viability of a cancer cell in a subject sample by 30 to 80% as compared to cells not exposed to an anti-nucleolin antibody (e.g., human and/or monoclonal). In some embodiments, an isolated anti-nucleolin antibody (e.g., human and/or monoclonal) is used to reduce cell viability of a cancer cell in a subject sample by 30 to 80% as compared cells not exposed to an anti-nucleolin antibody (e.g., human and/or monoclonal). In some embodiments, an isolated anti-nucleolin antibody (e.g., human and/or monoclonal) produced from a B cell (e.g., human B cell) is provided and used to reduce cell viability of a cancer cell in a subject sample by 30 to 80% as compared cells not exposed to an anti-nucleolin antibody (e.g., human and/or monoclonal).

In some embodiments, an anti-nucleolin antibody (e.g., human and/or monoclonal) is used to reduce cell viability of a cancer cell in a subject by 30 to 80% as compared cells not exposed to an anti-nucleolin antibody (e.g., human and/or monoclonal). In some embodiments, an isolated anti-nucleolin antibody (e.g., human and/or monoclonal) is used to reduce cell viability of a cancer cell in a subject by 30 to 80% as compared cells not exposed to an anti-nucleolin antibody (e.g., human and/or monoclonal). In some embodiments, an isolated anti-nucleolin antibody (e.g., human and/or monoclonal) produced from a B cell (e.g., human B cell) is provided and used to reduce cell viability of a cancer cell in a subject by 30 to 80% as compared cells not exposed to an anti-nucleolin antibody (e.g., human and/or monoclonal).

In some embodiments, an anti-nucleolin antibody (e.g., human and/or monoclonal) is administered to a human subject with one or more forms of cancer. In some embodiments an isolated anti-nucleolin antibody (e.g., human and/or monoclonal) is administered to a human subject with one or more forms of cancer. In some embodiments at least one of the forms of cancer is inhibited or killed by an anti-nucleolin antibody (e.g., human and/or monoclonal). In some embodiments an isolated anti-nucleolin antibody (e.g., human and/or monoclonal) is administered to a human subject where the cancer is resistant to other cancer treatments. In some embodiments an isolated anti-nucleolin antibody (e.g., human and/or monoclonal) produced from a B cell (e.g., human B cell) is provided is administered to a human subject where the cancer is resistant to other cancer treatments. For example, cancers can be resistant to radiation therapy, chemotherapy, or biological therapy. In some embodiments the immune system of the human subject is more tolerant to the isolated anti-nucleolin antibody (e.g., human and/or monoclonal) than to an isolated non anti-nucleolin antibody (e.g., human and/or monoclonal). In some embodiments, the immune system of the human subject is more tolerant to the isolated anti-nucleolin antibody (e.g., human and/or monoclonal) than to an isolated humanized anti-nucleolin antibody. In some embodiments, the immune system of the human subject is more tolerant to the isolated anti-nucleolin antibody (e.g., human and/or monoclonal) than to an isolated chimeric anti-nucleolin antibody.

In some embodiments, an anti-nucleolin antibody (e.g., human and/or monoclonal) is used to inhibit or kill a cell as part of an adjuvant therapy. In some embodiments, an isolated anti-nucleolin antibody (e.g., human and/or monoclonal) is used to inhibit or kill a cell as part of an adjuvant therapy. In some embodiments, an isolated anti-nucleolin antibody (e.g., human and/or monoclonal) expressed by a B cell (e.g., human B cell) is provided and used as part of an adjuvant therapy. Adjuvant therapy can include chemotherapy, radiation therapy, hormone therapy, targeted therapy, or biological therapy. Adjuvant therapy as used herein refers to treatment given after the primary treatment to lower the risk that the cancer will come back.

In some embodiments, an anti-nucleolin antibody (e.g., human and/or monoclonal) is used to inhibit or kill a cell used in combination with an adjuvant therapy. In some embodiments, an isolated anti-nucleolin antibody (e.g., human and/or monoclonal) is used to inhibit or kill a cell used in combination with an adjuvant therapy. In some embodiments, an isolated anti-nucleolin antibody (e.g., human and/or monoclonal) expressed by a B cell (e.g., human B cell) is provided as part of an adjuvant therapy. Adjuvant therapy may include chemotherapy, radiation therapy, hormone therapy, targeted therapy, or biological therapy.

In some embodiments, an anti-nucleolin antibody (e.g., human and/or monoclonal) is used to inhibit or kill a cell of a non-malignant cell proliferative disorder wherein nucleolin is expressed on the cell surface or in the cytoplasm. In some embodiments, an isolated anti-nucleolin antibody (e.g., human and/or monoclonal) is used to inhibit or kill a cell of a non-malignant cell proliferative disorder wherein nucleolin is expressed on the cell surface or in the cytoplasm. In some embodiments, the isolated anti-nucleolin antibody (e.g., human and/or monoclonal) is expressed by a B cell (e.g., human B cell). For example, specific non-limiting examples of non-malignant cell proliferative disorders that can treat or inhibited with an anti-nucleolin antibody include but are not limited to warts, benign prostatic hyperplasia, skin tags, and non-malignant tumors. For example, an isolated anti-nucleolin antibody (e.g., human and/or monoclonal) can be used to determine such cell proliferative disorders as benign prostatic hyperplasia or unwanted genital warts by targeting the undesirable cells that characterize such conditions for removal. Expression of nucleolin on the cell surface of endothelial cells in tumors has been shown to be a unique marker of tumor angiogenesis (Christian et al., 2003). In some embodiments, an anti-nucleolin antibody (e.g., human and/or monoclonal) is used to inhibit or kill in a subject a cell comprising an angiogenic tumor. In some embodiments, an isolated anti-nucleolin antibody (e.g., human and/or monoclonal) is used to inhibit or kill in a subject a cell comprising an angiogenic tumor. In some embodiments, an isolated anti-nucleolin antibody (e.g., human and/or monoclonal) expressed by a B cell (e.g., human B cell) is provided that can inhibit or kill in a subject a cell comprising an angiogenic tumor. An angiogenic tumor as used herein a tumor cell with a proliferation of a network of blood vessels that penetrate into cancerous growths, supplying nutrients and oxygen and removing waste products.

In some embodiments, an anti-nucleolin antibody (e.g., human and/or monoclonal) is used to inhibit or kill in a subject a tumor cell under conditions of tumor hypoxia. In some embodiments, an isolated anti-nucleolin antibody (e.g., human and/or monoclonal) is used to inhibit or kill in a subject a tumor cell under conditions of tumor hypoxia. In some embodiments, an isolated anti-nucleolin antibody (e.g., human and/or monoclonal) expressed by a B cell (e.g., human B cell) is provided that can inhibit or kill in a subject a tumor cell under conditions of tumor hypoxia. Tumor hypoxia occurs in the situation where tumor cells have been deprived of oxygen. Tumor hypoxia can be a result of the high degree of cell proliferation undergone in tumor tissue, causing a higher cell density, and thus taxing the local oxygen supply.

In some embodiments, an anti-nucleolin antibody (e.g., human and/or monoclonal) is used to inhibit or kill in subject a lymphocyte cell expressing nucleolin on its surface. In some embodiments, an isolated anti-nucleolin antibody (e.g., human and/or monoclonal) is used to inhibit or kill in subject a lymphocyte cell expressing nucleolin on its surface. In some embodiments, an isolated anti-nucleolin antibody (e.g., human and/or monoclonal) expressed by a B cell (e.g., human B cell) is provided that is used to inhibit or kill in subject a lymphocyte cell expressing nucleolin on its surface. In some embodiments, the lymphocyte cell comprises a B cell, T cell, or natural killer cell. In some embodiments, the lymphocyte cell comprises a CD4-positive or CD8-positive cells.

In some embodiments, an anti-nucleolin antibody (e.g., human and/or monoclonal) is used to inhibit or kill in a subject an activated lymphocyte or memory cell expressing nucleolin on its surface. In some embodiments, an isolated anti-nucleolin antibody (e.g., human and/or monoclonal) is used to inhibit or kill in a subject an activated lymphocyte or memory cell expressing nucleolin on its surface. In some embodiments, an isolated anti-nucleolin antibody (e.g., human and/or monoclonal) expressed by a B cell (e.g., human B cell) is provided that is used to inhibit or kill in subject an activated lymphocyte cell or memory cell expressing nucleolin on its surface. In a further embodiment, the activated lymphocyte comprises an activated B cell, T cell, or natural killer cell. In some embodiments, an anti-nucleolin antibody (e.g., human and/or monoclonal) is used to inhibit or kill a cell in a subject having an autoimmune disorder. In some embodiments, an isolated anti-nucleolin antibody (e.g., human and/or monoclonal) is used to inhibit or kill a cell in a subject having an autoimmune disorder. In some embodiments, an isolated anti-nucleolin antibody (e.g., human and/or monoclonal) expressed by a B cell (e.g., human B cell) is provided that is used to inhibit or kill a cell in a subject having an autoimmune disorder, including but not limited to alopecia greata, ankylosing spondylitis, antiphospholipid syndrome, autoimmune Addison's disease, asthma, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes, type 1 diabetes mellitus, diabetic retinopathy, eosinophilic fascites, fibromyalgia-fibromyositis, glomerulonephritis, Graves' disease, Guillain-Barre, Hashimoto's thyroiditis, Henoch-Schonlein purpura, idiopathic pulmonary fibrosis, idiopathic/autoimmune thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus-related disorders (e.g., pemphigus vulgaris), pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, Rheumatoid arthritis, sarcoidosis, scleroderma, Sjogren's syndrome, stiff-man syndrome, systemic lupus erythematosus (SLE), Sweet's syndrome, Still's disease, lupus erythematosus, takayasu arteritis, temporal arteritis/giant cell arteritis, ulcerative colitis, uveitis, vasculitis such as dermatitis herpetiformis vasculitis, vitiligo, and Wegener's granulomatosis. Examples of inflammatory disorders include, but are not limited to, asthma, encephalitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, graft versus host disease, urticaria, Vogt-Koyanagi-Hareda syndrome, chronic inflammatory pneumonitis, and chronic inflammation resulting from chronic viral or bacteria infections.

In some embodiments, an anti-nucleolin antibody (e.g., human and/or monoclonal) or fragment is used to inhibit or kill a cell in a subject infected by a virus, including but not limited to cells infected with Retroviridae (e.g., human immunodeficiency viruses, such as HIV-1 (also referred to as HTLV-III, LAV or HTLV-III/LAV, or HIV-III); and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviradae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Rous sarcoma virus (RSV), avian leukemia virus (ALV), and avian myeloblastosis virus (AMV)) and C-type group B (including feline leukemia virus (FeLV), gibbon ape leukemia virus (GALV), spleen necrosis virus (SNV), reticuloendotheliosis virus (RV) and simian sarcoma virus (SSV)), D-type retroviruses include Mason-Pfizer monkey virus (MPMV) and simian retrovirus type 1 (SRV-1), the complex retroviruses including the subgroups of lentiviruses, T-cell leukemia viruses and the foamy viruses, lentiviruses including HIV-1, HIV-2, SIV, Visna virus, feline immunodeficiency virus (Hy), and equine infectious anemia virus (EIAV), simian T-cell leukemia virus (STLV), and bovine leukemia virus (BLV), the foamy viruses including human foamy virus (HFV), simian foamy virus (SFV) and bovine foamy virus (BFV), Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses), *Mycobacterium* (*Mycobacterium tuberculosis*, *M. bovis*, *M. avium-intracellulare*, *M. leprae*), Pneumococcus, *Streptococcus*, Staphylcococcus, Diphtheria, *Listeria*, Erysipelothrix, Anthrax, Tetanus, *Clostridium*, Mixed Anaerobes, *Neisseria*, *Salmonella*, *Shigella*, Hemophilus, *Escherichia coli*, *Klebsiella*, *Enterobacter*, *Serratia*, *Pseudomonas*, Bordatella, *Francisella tularensis*, *Yersinia*, *Vibrio cholerae*, *Bartonella*, *Legionella*, Spirochaetes (*Treponema*, *Leptospira*, *Borrelia*), Fungi, *Actinomyces*, *Rickettsia*, *Mycoplasma*, *Chlamydia*, Protozoa (including *Entamoeba*, *Plasmodium*, *Leishmania*, *Trypanosoma*, *Toxoplasma*, *Pneumocystis*, Babasia, Giardia, *Cryptosporidium*, *Trichomonas*), Helminths (*Trichinella*, *Wucheraria*, *Onchocerca*, *Schistosoma*, Nematodes, Cestodes, Trematodes), and viral pneumonias. Additional examples of antigens which can be targets for compositions of the present disclosure are known, such as those disclosed in U.S. Patent Publication No. 2007/0066554. In a further aspect, a conjugate can comprise an antigen or cellular component as described herein, but in addition to a targeting moiety and an immunostimulatory nucleic acid molecule.

5.2. Antibody Conjugates

In some embodiments, the present disclosure provides for an isolated anti-nucleolin antibody (e.g., human and/or monoclonal) linked to at least one therapeutic agent to form an antibody conjugate. In some embodiments, an isolated anti-nucleolin antibody (e.g., human and/or monoclonal), is linked, or covalently bound, or complexed to at least one therapeutic agent, such as a molecule or moiety. Therapeutic agents comprise molecules having a desired activity, e.g., cytotoxic activity. In some embodiments, a therapeutic agent which can be attached to an antibody includes but is not limited to a toxin (such as a peptide immunotoxin that catalytically inhibit the elongation step of protein synthesis) an anti-tumor agent, a therapeutic enzyme, a radionuclide, an antiviral agent, a chelating agent as described herein, a cytokine, a growth factor, or a oligo- or polynucleotide.

In some embodiments, an isolated anti-nucleolin antibody (e.g., human and/or monoclonal) is conjugated to an enzymatically active toxin or fragment thereof. Examples of enzymatically active toxins and fragments thereof include, but are not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), pokeweed antiviral protein, *Momordica charantia* inhibitor, curcin, crotin, *Sapaonaria officinalis* inhibitor, gelonin, mitogellin, restrictocin, phenomycin, enomycin, calicheamicins or the tricothecenes.

In some embodiments, an isolated anti-nucleolin antibody (e.g., human and/or monoclonal) is conjugated to a radionuclide. Examples of suitable radionuclides include, but are not limited to, $^{124}$antimony, $^{125}$antimony, $^{74}$arsenic, $^{211}$astatine, $^{103}$barium, $^{140}$barium, $^{7}$beryllium, $^{206}$bismuth, $^{207}$bismuth, $^{212}$Bi, $^{109}$cadmium, $^{115}$cadmium, $^{45}$calcium, $^{14}$carbon, $^{139}$cerium, $^{141}$cerium, $^{144}$cerium, $^{137}$cesium, $^{51}$chromium, $^{36}$chlorine, $^{56}$cobalt, $^{57}$cobalt, $^{58}$cobalt, $^{60}$cobalt, $^{67}$copper, $^{169}$erbium, $^{152}$eurpium, $^{67}$gallium, $^{153}$gadolinium, $^{195}$gold, $^{199}$gold, $^{175}$hafnium, $^{175+181}$hafnium, $^{181}$hafnium, $^{3}$hydrogen, $^{123}$iodine, $^{125}$iodine, $^{131}$iodine, $^{111}$indium, $^{131}$In, $^{192}$iridium, $^{55}$iron, $^{59}$iron, $^{85}$krypton, $^{210}$lead, $^{177}$lutecium, $^{54}$manganese, $^{197}$mercury, $^{203}$mercury, $^{99}$molybdenum, $^{147}$neodynium, $^{237}$neptunium, $^{63}$nickel, $^{95}$niobium $^{185+191}$osmium, $^{103}$palladium, $^{32}$phosphorus, $^{184}$platinum, $^{143}$praseodymium, $^{147}$promethium, $^{233}$protactinium, $^{226}$radium, rhenium$^{186}$, $^{188}$rhenium, $^{86}$rubidium, $^{130}$ruthenium, $^{106}$ruthenium, $^{44}$scandium, $^{46}$scandium, $^{45}$selenium, $^{75}$selenium, $^{110m}$silver, $^{111}$silver, $^{22}$sodium, $^{85}$strontium, $^{89}$strontium, $^{90}$strontium, $^{35}$sulphur, $^{182}$tantalum, $^{99m}$technicium, $^{125m}$tellurium, $^{132}$tellurium, $^{160}$terbium, $^{204}$thallium, $^{228}$thorium, $^{232}$thorium, $^{170}$thullium, $^{113}$tin, $^{44}$titanium, $^{185}$tungsten, $^{48}$vanadium, $^{49}$vanadium, $^{88}$yttrium, $^{90}$yttrium, $^{91}$yttrium, $^{169}$ytterbium, $^{65}$zinc, and/or $^{95}$zirconium.

Conjugates of the antibody and cytotoxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

In some embodiments, an isolated anti-nucleolin antibody (e.g., human and/or monoclonal) is conjugated to a cytokine. The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; and other polypeptide factors including LIF and kit ligand (KL). As used herein, the term cytokine includes proteins from natural sources or from recombinant cell culture and biologically active equivalents of the native sequence cytokines.

In some embodiments, an isolated anti-nucleolin antibody (e.g., human and/or monoclonal) is conjugated to a chemotherapeutic agent. A variety of chemical compounds, also described as "chemotherapeutic agents," function to induce DNA damage. Categories of chemotherapeutic agents suitable for conjugation with a an isolated anti-nucleolin antibody (e.g., human and/or monoclonal) include, but are not limited to, alkylating agents, anthracyclines, cytoskeletal disruptors, epothilones, inhibitors of topoisomerase I, inhibitors of topoisomerase II, nucleoside and nucleotide analogs and precursor analogs, peptide antibiotics, platinum-based agents, retinoids, or vinca alkaloids and derivatives. Specific chemotherapeutic agents within these groups include, but are not limited to, actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, thioguanine, valrubicin, vinblastine, vincristine, vindesine, vinorelbine. The present disclosure also encompasses the use of a combination of one or more DNA damaging agents, whether radiation-based or actual compounds, such as the use of X-rays with cisplatin or the use of cisplatin with etoposide.

In some embodiments, an isolated anti-nucleolin antibody (e.g., human and/or monoclonal) is conjugated to an anti-viral agent. Example of anti-viral agents that can be used with an isolated anti-nucleolin antibody (e.g., human and/or monoclonal) include, but are not limited to, substrates and substrate analogs, inhibitors and other agents that severely impair, debilitate or otherwise destroy virus-infected cells. Substrate analogs include amino acid and nucleoside analogs. Substrates can be conjugated with toxins or other virucidal substances. Inhibitors include integrase inhibitors, protease inhibitors, polymerase inhibitors and transcriptase inhibitors such as reverse transcriptase inhibitors.

5.3. Pharmaceutical Compositions and Administration

It is envisioned that, for administration to a subject in need thereof, an antibody will be suspended in a composition suitable for administration to a host. In some embodiments the antibody is a monoclonal antibody. In some embodiments the monoclonal antibody is an anti-nucleolin antibody. In some embodiments the monoclonal anti-nucleolin antibody is a human monoclonal anti-nucleolin antibody. Aqueous compositions of the present disclosure comprise an effective amount of an antibody dispersed in a pharmaceutically acceptable composition and/or aqueous medium. The phrases "pharmaceutically and/or pharmacologically acceptable" refer to compositions that do not produce an adverse, allergic and/or other untoward reaction when administered to an animal, and specifically to humans, as appropriate.

As used herein, "pharmaceutically acceptable carrier" includes any solvents, dispersion media, coatings, antibacterial and/or antifungal agents, isotonic and/or absorption delaying agents and the like. The use of such media or agents for pharmaceutical active substances is well known in the art. Supplementary active ingredients can also be incorporated into the compositions. For administration to humans, preparations should meet sterility, pyrogenicity, general safety and/or purity standards as required by FDA Office of Biologics standards.

In some embodiments, an anti-nucleolin antibody (e.g., human and/or monoclonal) of the present disclosure can be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with suitable excipient(s), adjuvants, and/or pharmaceutically acceptable carriers. In some embodiments of the present disclosure, the pharmaceutically acceptable carrier is pharmaceutically inert.

Administration of pharmaceutical compositions is accomplished orally or parenterally. Methods of parenteral delivery include topical, intra-arterial (e.g., directly to a tumor), intramuscular, subcutaneous, intramedullary, intrathecal, intraventricular, intravenous, intraperitoneal, or intranasal administration. In addition to the active ingredients, these pharmaceutical compositions can contain suitable pharmaceutically acceptable carriers comprising excipients and other compounds that facilitate processing of the active compounds into preparations which can be used pharmaceutically. Further details on techniques for formulation and administration may be found in the latest edition of "Remington's Pharmaceutical Sciences" (Maack Publishing Co, Easton Pa.). Antibody compositions can be lyophilized. Antibody compositions can be aqueous antibody. The compositions to be used for in vivo administration are generally sterile (e.g., by filtration through sterile filtration membranes).

Some compositions can be suitable for targeted delivery to the brain or the spinal fluid of a subject. The composition can be substantially free of preservatives. Some compositions are stable for at least about 12 months, at least about 18 months, at least about 24 months, or at least about 30 months. Some compositions are stable at about −80° C. to about 40° C., at about 0° C. to about 25° C., at about 0° C. to about 10° C., such as at about −80° C. to about −50° C. or at about 2° C. to about 8° C.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, etc., suitable for ingestion by the patient. See PCT publication WO 93/23572.

Pharmaceutical preparations for oral use may be obtained through combination of active compounds with solid excipient, optionally grinding a resulting mixture, and processing the mixture of granules, after adding suitable additional compounds, if desired, to obtain tablets or dragee cores. Suitable excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical compositions for parenteral administration include aqueous solutions of active compounds. For injection, the pharmaceutical compositions of the present disclosure may be formulated in aqueous solutions, such as in physiologically compatible buffers such as Hank's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the composition. Such penetrants are generally known in the art.

The pharmaceutical compositions of the present disclosure may be manufactured in a manner similar to that known in the art (e.g., by means of conventional mixing, dissolving, granulating, dragee-making, levigating, emulsifying, encapsulating, entrapping or lyophilizing processes).

The pharmaceutical composition may be provided as a salt and can be formed with many acids, including but not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc. Salts tend to be more soluble in aqueous or other protonic solvents that are the corresponding free base forms. In some embodiments, the preparation may be a lyophilized powder in 1 mM-50 mM histidine, 0.1%-2% sucrose, 2%-7% mannitol, at a pH range of 4.5 to 5.5, which is combined with buffer prior to use.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it may be suitable to include isotonic agents, for example, sugars or sodium chloride. Prolonged absorption of the injectable compositions can be brought about by the use in the compositions of agents delaying absorption, for example, aluminum monostearate and gelatin.

Pharmaceutical compositions suitable for use in the present disclosure include compositions wherein the active ingredients are contained in an effective amount to achieve the intended purpose. "Therapeutically effective amount" or "pharmacologically effective amount" are well recognized phrases and refer to that amount of an agent effective to produce the intended pharmacological result. Thus, a therapeutically effective amount is an amount sufficient to ameliorate the symptoms of the disease being treated. One useful assay in ascertaining an effective amount for a given application (e.g., a therapeutically effective amount) is measuring the effect on cell survival. The amount actually administered will be dependent upon the individual to which treatment is to be applied, and will probably be an optimized amount such that the desired effect is achieved without significant side-effects.

For any compound, the therapeutically effective dose can be estimated initially either in cell culture assays or in any appropriate animal model. The animal model is also used to achieve a desirable concentration range and route of administration. Such information can then be used to determine useful doses and routes for administration in humans.

In an animal, a "therapeutically effective amount" is the quantity of compound which results in an improved clinical outcome as a result of the treatment compared with a typical clinical outcome in the absence of the treatment. An "improved clinical outcome" refers, for, example, to a longer life expectancy, fewer complications, fewer symptoms, less physical discomfort and/or fewer hospitalizations as a result of the treatment. Improved clinical outcome can be quantified as a certain percent of subjects receiving administration and improving in their disease state over certain period of time. The certain percent of subjects receiving administration and improving in their disease state may be about 1%, 2%, 3%, 4%, 5%, 6%, 7%, 8%, 9%, or 10%. The certain percent of subjects receiving administration and improving in their disease state may be about 10%, 20%, 30%, 40%, 50%, 60%, 70%, 80%, or 85%. The certain percent of subjects receiving administration and improving in their disease state may be about 85%, 86%, 87%, 88%, 89%, 90%, 91%, 92%, 93%, 94%, 95%, 96%, 97%, 98%, 99%, or 100%. The certain period of time to measure improved clinical outcome may be 1, 2, 3, 4, 5, 6, or 7 days. The certain period of time to measure improved clinical outcome may be 1, 2, 3, or 4 weeks. The certain period of time to measure improved clinical outcome may be 1, 2, 3, 4, 5, 6, 7, 8, 9, 10 or more years.

With respect to cancer, an "improved clinical outcome" includes a longer life expectancy. It can also include slowing or arresting the rate of growth of a tumor, causing shrinkage in the size of the tumor, a decreased rate of metastasis or an improved quality of life (e.g., a decrease in physical discomfort or an increase in mobility).

With respect to modulation of the immune system, "an improved clinical outcome" refers to an increase in the magnitude of the immune response in the individual, if the individual has a disease involving immune suppression. "An improved clinical outcome" for individuals with suppressed immune systems can also refer to a lesser susceptibility to infectious diseases. For diseases involving an overactive immune system, "an improved clinical outcome" can refer to a decrease in the magnitude of the immune response. In both cases, an improved clinical outcome can also involve an improvement in the quality of life, as described above.

The exact dosage is chosen by the individual physician in view of the patient to be treated. Dosage and administration are adjusted to provide sufficient levels of the active moiety or to maintain the desired effect. Additional factors which may be taken into account include the severity of the disease state (e.g., tumor size and location; age, weight and gender of the patient; diet, time and frequency of administration, drug combination(s), reaction sensitivities, and tolerance/response to therapy). Administration may be every day, every other day, every week, every other week, every month, every other month, or any variation thereof. Administration of a dosage form comprising an anti-nucleolin antibody (e.g., human and/or monoclonal) may be for at least 1, 2, 3, 4, 5, 6, 7, 8, 9, or 10 days. Administration of a dosage form comprising an anti-nucleolin antibody (e.g., human and/or monoclonal) may be for at least 1, 2, 3, 4, 5, 6, 7, 8, 9, or 10 weeks. Administration of a dosage form comprising an anti-nucleolin antibody (e.g., human and/or monoclonal) may be for at least 1, 2, 3, 4, 5, 6, 7, 8, 9, 10, 11, or 12 months. Administration of a dosage form comprising an anti-nucleolin antibody (e.g., human and/or monoclonal) may be for at least 1, 2, 3, 4, 5, 6, 7, 8, 9, 10, 11, or 12 years. Administration of one or more agents (e.g., an anti-nucleolin antibody (e.g., human and/or monoclonal) and another agent) can be intermittent; for example, administration can be once every two days, every three days, every five days, once a week, once or twice a month, and the like. Long acting pharmaceutical compositions may be administered every 3 to 4 days, every week, or once every two weeks depending on half-life and clearance rate of the particular composition. Guidance as to particular dosages and methods of delivery is provided in the literature (see, U.S. Pat. Nos. 4,657,760; 5,206,344; and 5,225,212, herein incorporated by reference). In some embodiments, the dosage of a composition comprising anti-nucleolin antibody (e.g., human and/or monoclonal) is administered to a patient is about 0.1 mg/kg to 500 mg/kg of the patient's body weight. The amount, forms, and/or amounts of the different forms can be varied at different times of administration.

An antibody or composition disclosed herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route. For example, dosing can be by injections (e.g., intravenous or subcutaneous injections). Various dosing schedules including but not limited to single or multiple administrations over various time-points, bolus administration, and pulse infusion are contemplated herein.

Antibody disclosed herein can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the composition, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody disclosed herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. About 1 µg/kg to 15 mg/kg (e.g., 0.1 mg/kg-10 mg/kg) of antibody can be an initial candidate dosage for administration to the patient (e.g., by one or more separate administrations, or by continuous infusion). A daily dosage might range from about 1 µg/kg to 100 mg/kg or more. For repeated administrations over several days or longer the treatment would generally be sustained until a desired suppression of infection or disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently (e.g., every week or every three weeks). An initial higher loading dose, followed by one or more lower doses may be administered.

Pharmaceutical compositions of an antibody as described herein are prepared by mixing such antibody having the desired degree of purity with one or more optional pharmaceutically acceptable carriers (See, e.g., Remington's Pharmaceutical Sciences 16th edition, Osol, A. Ed. (1980)), in the form of lyophilized compositions or aqueous solutions. Pharmaceutically acceptable carriers are generally nontoxic to recipients at the dosages and concentrations employed. Exemplary pharmaceutical acceptable carriers include buffers (e.g., phosphate, citrate, and other organic acids); antioxidants (e.g., ascorbic acid and methionine); preservatives (e.g., octadecyldimethylbenzyl ammonium chloride); hexamethonium chloride; benzalkonium chloride; benzethonium chloride; phenol, butyl or benzyl alcohol; alkyl parabens (e.g., methyl or propyl paraben); catechol; resorcinol; cyclohexanol; 3-pentanol; and m-cresol; low molecular weight (less than about 10 residues) polypeptides; proteins, (e.g., serum albumin, gelatin, or immunoglobulins); hydrophilic polymers (e.g., polyvinylpyrrolidone); amino acids (e.g., glycine, glutamine, asparagine, histidine, arginine, or lysine); monosaccharides, disaccharides, and other carbohydrates (e.g., glucose, mannose, or dextrins); chelating agents (e.g., EDTA); sugars (e.g., sucrose, mannitol, trehalose or sorbitol); salt-forming counter-ions (e.g., sodium); metal complexes (e.g., Zn-protein complexes); and/or non-ionic surfactants (e.g., polyethylene glycol (PEG)). Exemplary pharmaceutically acceptable carriers herein further include interstitial drug dispersion agents (e.g., soluble neutral-active hyaluronidase glycoproteins (sHASEGP)). In one aspect, a sHASEGP is combined with one or more additional glycosaminoglycanases (e.g., chondroitinases).

Active ingredients may be entrapped in microcapsules (e.g., hydroxymethylcellulose or gelatin-microcapsules and poly-(methylmethacylate) Active ingredients may be entrapped in microcapsules in colloidal drug delivery systems (e.g., liposomes, albumin microspheres, microemulsions, nano-particles and nanocapsules) or in macroemulsions. Sustained-release preparations may be prepared. Suitable examples of sustained-release preparations include semipermeable matrices of solid hydrophobic polymers containing the antibody, which matrices are in the form of shaped articles (e.g., films or microcapsules).

In some liquid compositions, the concentration of the antibody is about 0.1 mg/ml to about 60 mg/ml, about 40 mg/ml to about 60 mg/ml, about 17 mg/ml to about 23 mg/ml, about 50 mg/ml, about 30 mg/ml, about 17 mg/ml to about 23 mg/ml, about 20 mg/ml, about 17 mg/ml, about 10 mg/ml, about 5 mg/ml, about 2 mg/ml, or about 1 mg/ml. In some compositions, at least one tonicity agent (e.g., D-mannitol) and is present at a concentration of about 1% w/v to about 10% w/v, about 2% w/v to about 6% w/v, or about 4% w/v. In some compositions, at least one buffering agent (e.g., histidine, succinate) is present at a concentration of about 0.1 mM to about 25 mM, about 5 mM to about 15 mM, about 5 mM or about 10 mM. In some compositions, an antioxidant (e.g., methionine) is present at a concentration of about 0.1 mM to about 25 mM, about 5 mM to about 15 mM, or about 10 mM. In some compositions, a stabilizer (e.g., polysorbate 80) is present at a concentration of about 0.001% w/v to about 0.01% w/v, about 0.005% w/v to about 0.01% w/v, or about 0.005% w/v. A composition disclosed herein can have a pH of about 4 to about 8, about 4.5 to about 7.5, about 5 to about 7, about 5.5 to about 6.5, about 6.0 to about 6.5, about 6.2, about 6.0, or about 5.5.

In some embodiments, an antibody disclosed herein is present in a composition from about 0.1 mg/ml to about 100 mg/ml, from about 0.1 mg/ml to about 75 mg/ml, from about 0.1 mg/ml to about 50 mg/ml, from about 0.1 mg/ml to about 40 mg/ml, from about 0.1 mg/ml to about 30 mg/ml, from about 10 mg/ml to about 20 mg/ml, about 12 mg/ml to about 17 mg/ml, about 17 mg/ml to about 23 mg/ml, from about 20 mg/ml to 30 mg/ml, or higher, for example, up to about 100 mg/ml, about 200 mg/ml, about 500 mg/ml, or about 1000 mg/ml or more. In various embodiments, the antibody is present at about 1, 2, 5, 10, 15, 16, 17, 18, 19, 20, 21, 22, 23, 24, 25 or 30 mg/ml. Ranges of values using a combination of any of the above recited values as upper and/or lower limits are intended to be included.

In some embodiments, compositions disclosed herein are stable to freezing, lyophilization and/or reconstitution. Moreover, exemplary embodiments are stable over extended periods of time. For example, the compositions are stable for at least about 6, 7, 8, 9, 10, 11, 12, 13, 14, 15, 16, 17, 18, 19, 20, 21, 22, 23, 24, 25, 26, 27, 28, 29, or 30 months. In some embodiments, the compositions are stable for at least about 12 months, for at least about 18 months, for at least about 24 months, or for at least about 30 months. In some embodiments, the composition may be stored at temperatures from about −80° C. to about 40° C., from about 0° C. to about 25° C., from about 0° C. to about 15° C., or from about 0° C. to about 10° C., for example from about 2° C. to about 8° C. In various embodiments, the composition may be stored at about 0° C., 1° C., 2° C., 3° C., 4° C., 5° C., 6° C., 7° C., 8° C., 9° C. or 10° C. In some embodiments, the composition is stored at about 5° C. Generally, the composition is stable and retains biological activity at these ranges. Ranges intermediate to the above recited temperatures, for example, from about 2° C. to about 17° C., are also intended to be part of this invention. For example, ranges of values using a combination of any of the above recited values as upper and/or lower limits are intended to be included.

Dosage

Effective doses of the compositions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages need to be titrated to optimize safety and efficacy.

For passive immunization with an antibody, exemplary dosages are from about 0.0001 mg/kg to about 100 mg/kg, about 0.01 mg/kg to about 5 mg/kg, about 0.15 mg/kg to about 3 mg/kg, 0.5 mg/kg to about 2 mg/kg, for example about 1 mg/kg to about 2 mg/kg of the host body weight. In some exemplary embodiments, dosages can be about 0.5, 0.6, 0.7, 0.75, 0.8, 0.9, 1.0, 1.2, 1.25, 1.3, 1.4, 1.5, 1.6, 1.7, 1.75, 1.8, 1.9, or 2.0 mg/kg. Other exemplary dosages for passive immunization are from about 1 mg/kg to about 20 mg/kg. In some exemplary embodiments, dosages can be about 5, 10, 15 or 20 mg/kg. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Antibody is usually administered on multiple occasions. Intervals between single dosages can be weekly, monthly or yearly. Intervals can also be irregular as indicated by measuring blood levels of antibody in the patient. In some methods, dosage is adjusted to achieve a plasma antibody concentration of 1-1000 μg/ml and in some methods 25-300 μg/ml. In some embodiments, antibody can be administered as a sustained release composition, in which case less frequent administration is required. Dosage and frequency vary depending on the half-life of the antibody in the patient. In general, human antibodies show the longest half-life, followed by humanized antibodies, chimeric antibodies, and nonhuman antibodies.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In some therapeutic applications, a relatively high dosage (for example, from about 0.5 or 1 to about 200 mg/kg of antibody per dose (for example 0.5, 1, 1.5, 2, 5, 10, 20, 25, 50, or 100 mg/kg), with dosages of from 5 to 25 mg/kg being more commonly used) at relatively short intervals is sometimes required until progression of the disease is reduced or terminated, and for example until the patient shows partial or complete amelioration of symptoms of disease. Thereafter, the patent can be administered a prophylactic regime.

It is especially advantageous to provide compositions in unit dosage form for ease of administration and uniformity of dosage. Compositions may be presented in capsules, ampules, lyophilized form, or in multi-dose containers. The term "container" refers to something, for example, a holder, receptacle, or vessel, into which an object or liquid can be placed or contained, for example, for storage. The unit dosage form may comprise any composition described herein including suspensions, solutions or emulsions of the active ingredient together with formulating agents such as suspending, stabilizing and/or dispersing agents. In an exemplary embodiment, the pharmaceutical dosage unit form may be added to an intravenous drip bag (for example a 50 ml, 100 ml, or 250 ml, or 500 ml drip bag) with a suitable diluent, for example, sterile pyrogen-free water or saline solution, before administration to the patient, for example, by intravenous infusion. Some pharmaceutical unit dosage forms may require reconstitution with a suitable diluent prior to addition to an intravenous drip bag, for example lyophilized forms. In exemplary embodiments, the pharmaceutical unit dosage form is a container containing a composition described herein. For example, the container may be a 10 mL glass, type I, tubing vial. Generally, the container should maintain the sterility and stability of the composition. For example, the vial may be closed with a serum stopper. Furthermore, in various embodiments, the container should be designed so as to allow for withdrawal of about 100 mg of composition or active ingredient (for example, for single use). In some embodiments, the container may be suitable for larger amounts, of composition or active ingredient, for example, from about 10 mg to about 5000 mg, from about 100 mg to about 1000 mg, and from about 100 mg to about 500 mg, about 40 mg to about 250 mg, about 60 mg to about 80 mg, about 80 mg to about 120 mg, about 120 mg to about 160 mg, or ranges or intervals thereof, for example, about 100 mg to about 200 mg. Ranges intermediate to the above recited amounts, for example, from about 25 mg to about 195 mg, are also intended to be part of this invention. For example, ranges of values using a combination of any of the above recited values as upper and/or lower limits are intended to be included. In some embodiments, the composition often is supplied as a liquid in unit dosage form.

In some aspects, the present disclosure provides a kit including a pharmaceutical dosage unit form (for example, a container with a composition disclosed herein), and instructions for use. Accordingly, the container and the kit may be designed to provide enough composition for multiple uses. In various embodiments, the kit may further include diluent. The diluent may include excipients, separate or combined. For example, the diluent may include a tonicity modifier such as mannitol, a buffering agent such as histidine, a stabilizer such as polysorbate 80, an anti-oxidant such as methionine, and/or combinations thereof. The diluent may contain other excipients, for example, lyoprotectant, as deemed necessary by one skilled in the art.

Excipients

In various embodiments, the present disclosure provides a composition that may include various excipients, including, but not limited to, buffer, anti-oxidant, a tonicity agent, and a stabilizer. In addition, the compositions may contain an additional agent for pH adjustment (for example, HCl) and a diluent (for example, water). In some embodiments, different forms of histidine can be used for pH adjustment. In part, the excipients serve to maintain the stability and the biological activity of the antibody (for example, by maintaining the proper conformation of the protein), and/or to maintain pH.

Buffering Agent

In various aspects, the composition includes a buffering agent (buffer). The buffer serves to maintain a physiologically suitable pH. In addition, the buffer can serve to enhance isotonicity and chemical stability of the composition. Generally, the composition should have a physiologically suitable pH. In various embodiments, the composition has a pH of about 5 to about 7, about 5.5 to about 6.5, for example about 6.0 to about 6.5. In some embodiments, the composition has a pH of about 6. Ranges intermediate to the above recited pH levels, for example, about pH 5.2 to about pH 6.3, for example pH 6.0 or pH 6.2, are also intended to be part of this invention. For example, ranges of values using a combination of any of the above recited values as upper and/or lower limits are intended to be included. The pH may be adjusted as necessary by techniques known in the art. For example, HCl may be added as necessary to adjust the pH to desired levels or different forms of histidine may be used to adjust the pH to desired levels.

The buffer may include, but is not limited to, succinate (sodium or phosphate), histidine, phosphate (sodium or potassium), Tris (tris (hydroxymethyl) aminomethane), diethanolamine, citrate, other organic acids and mixtures thereof. In some embodiments, the buffer is histidine (for example, L-histidine). In some embodiments, the buffer is succinate. In some embodiments, the composition includes an amino acid such as histidine that is present in an amount sufficient to maintain the composition at a physiologically suitable pH. Histidine is an exemplary amino acid having buffering capabilities in the physiological pH range. Histidine derives its buffering capabilities spanning from its imidazole group. In one exemplary embodiment, the buffer is L-histidine (base) (for example $C_6H_9N_3O_2$, FW: 155.15). In some embodiments, the buffer is L-histidine monochloride monohydrate (for example $C_6H_9N_3O_2 \cdot HCl \cdot H_2O$, FW: 209.63). In some embodiments, the buffer is a mixture of L-histidine (base) and L-histidine monochloride monohydrate.

In some embodiments, the buffer (for example, L-histidine or succinate) concentration is present from about 0.1 mM to about 50 mM, from about 0.1 mM to about 40 mM, from about 0.1 mM to about 30 mM, about 0.1 mM to about 25 mM, from about 0.1 mM to about 20 mM, or from about 5 mM to about 15 mM, for example 5 mM or 10 mM. In various embodiments, the buffer may be present at about 6 mM, 7 mM, 8 mM, 9 mM, 11 mM, 12 mM, 13 mM, 14 mM, or 15 mM. In some embodiments, the buffer is present at about 10 mM. Ranges intermediate to the above recited concentrations, for example, about 12 mM to about 17 mM, are also intended to be part of this invention. For example, ranges of values using a combination of any of the above recited values as upper and/or lower limits are intended to be included. In certain embodiments, the buffer is present in an amount sufficient to maintain a physiologically suitable pH.

Tonicity Agent

In various aspects, the composition includes a tonicity agent. In part, the tonicity agent contributes to maintaining the isotonicity of the composition, and to maintaining protein levels. In part, the tonicity agent contributes to preserving the level, ratio, or proportion of the therapeutically active polypeptide present in the composition. As used herein, the term "tonicity" refers to the behavior of biologic components in a fluid environment or solution. Isotonic solutions possess the same osmotic pressure as blood plasma, and so can be intravenously infused into a subject without changing the osmotic pressure of the subject's blood plasma. In some embodiments, tonicity agent is present in an amount sufficient to render the composition suitable for intravenous infusion. Often, the tonicity agent serves as a bulking agent as well. As such, the agent may allow the protein to overcome various stresses such as freezing and shear.

The tonicity agent may include, but is not limited to, $CaCl_2$, NaCl, $MgCl_2$, lactose, sorbitol, sucrose, mannitol, trehalose, raffinose, polyethylene glycol, hydroxyethyl starch, glycine and mixtures thereof. In some embodiments, the tonicity agent is mannitol (for example, D-mannitol, for example, $C_6H_{14}O_6$, FW: 182.17).

In some embodiments, the tonicity agent is present at about 2% to about 6% w/v, or about 3% to about 5% w/v. In some embodiments, the tonicity agent is present at about 3.5% to about 4.5% w/v. In some embodiments, the tonicity agent is percent at about 20 mg/ml to about 60 mg/ml, at about 30 mg/ml to about 50 mg/ml, or at about 35 mg/ml to about 45 mg/ml. For example, the tonicity agent is present at about 4% w/v or at about 40 mg/ml. In some embodiments, the tonicity agent is present at about 6% w/v. In some embodiments, the tonicity agent is present at about 10% w/v.

Ranges intermediate to the above recited concentrations, for example, about 3.2% to about 4.3% w/v or about 32 to about 43 mg/ml, are also intended to be part of this invention. For example, ranges of values using a combination of any of the above recited values as upper and/or lower limits are intended to be included. The tonicity agent should be present in a sufficient amount so as to maintain tonicity of the composition.

Anti-Oxidant

In various aspects, the composition includes an anti-oxidant so as to, in part, preserve the composition (for example, by preventing oxidation). The anti-oxidant may include, but is not limited to, GLA (gamma-linolenic acid)-lipoic acid, DHA (docosahexaenoic acid)-lipoic acid, GLA-tocopherol, di-GLA-3,3'-thiodipropionic acid and in general any of, for example, GLA, DGLA (dihomo-gamma-linolenic acid), AA (arachidonic acid), SA (salicylic acid), EPA (eicosapentaenoic acid) or DHA (docosahexaenoic acid) with any natural or synthetic anti-oxidant with which they can be chemically linked. These include phenolic anti-oxidants (for example, eugenol, carnosic acid, caffeic acid, BHT (butylated hydroxyanisol), gallic acid, tocopherols, tocotrienols and flavenoid anti-oxidants (such as myricetin and fisetin)), polyenes (for example, retinoic acid), unsaturated sterols (for example, $\Delta^5$-avenasterol), organosulfur compounds (for example, allicin), terpenes (for example, geraniol, abietic acid) and amino acid antioxidants (for example, methionine, cysteine, carnosine). In some embodiments, the anti-oxidant is ascorbic acid. The anti-oxidant is methionine, or an analog thereof, for example, selenomethionine, hydroxy methyl butanoic acid, ethionine, or trifluoromethionine.

In some embodiments, the anti-oxidant (for example, a methionine such as L-methionine, for example $CH_3SCH_2CH_2CH(NH_2)CO_2H$, FW=149.21) is present from about 0.1 mM to about 50 mM, from about 0.1-mM to about 40 mM, from about 0.1 mM to about 30 mM, from about 0.1 mM to about 20 mM, or from about 5 mM to about 15 mM. In various embodiments, the anti-oxidant may be present at about 5 mM, 6 mM, 7 mM, 8 mM, 9 mM, 10 mM, 11 mM, 12 mM, 13 mM, 14 mM, or 15 mM. For example, the anti-oxidant is present at about 10 mM. In some embodiments, the anti-oxidant is present at about 15 mM. Ranges intermediate to the above recited concentrations, for example, about 12 mM to about 17 mM, are also intended to be part of this invention. For example, ranges of values using a combination of any of the above recited values as upper and/or lower limits are intended to be included. In certain embodiments, the anti-oxidant should be present in a sufficient amount so as to preserve the composition, in part, by preventing oxidation.

Stabilizer

In various aspects, the composition includes a stabilizer, also known as a surfactant. Stabilizers are specific chemical compounds that interact and stabilize biological molecules and/or general pharmaceutical excipients in a composition. In certain embodiments, stabilizers may be used in conjunction with lower temperature storage. Stabilizers generally protect the protein from air/solution interface induced stresses and solution/surface induced stresses, which may otherwise result in protein aggregation. The stabilizer may include, but is not limited to, glycerin, polysorbates such as polysorbate 80, dicarboxylic acids, oxalic acid, succinic acid, adipic acid, fumaric acid, phthalic acids, and combinations thereof. In some embodiments, the stabilizer is polysorbate 80.

In some embodiments, the stabilizer (for example, polysorbate 80) concentration is about 0.001% w/v to about 0.01% w/v, about 0.001% w/v to about 0.009% w/v, or about 0.003% w/v to about 0.007% w/v. For example, the stabilizer concentration is about 0.005% w/v. In some embodiments, the stabilizer is present at about 0.01% w/v. Ranges intermediate to the above recited concentrations, for example, about 0.002% w/v to about 0.006% w/v, are also intended to be part of this invention. For example, ranges of values using a combination of any of the above recited values as upper and/or lower limits are intended to be included.

In some embodiments, the composition is substantially free of preservatives. In some embodiments, preservatives may be added as necessary. For example, cryoprotectants or lyoprotectants may be included, for example, should the composition be lyophilized.

5.4. Nucleolin-Expressing Cancers and Non-Malignant Cells

In some embodiments, an isolated anti-nucleolin antibody (e.g., human and/or monoclonal) produced in accordance with the present disclosure is used in treating a variety of cells, including both cancerous and non-cancerous cells. In some embodiments the isolated anti-nucleolin antibody (e.g., human and/or monoclonal) is a monoclonal antibody. In some embodiments, the isolated anti-nucleolin antibody (e.g., human and/or monoclonal) is a polyclonal antibody. The term "cancer" is described previously herein. Examples of types cancer that can be inhibited or treated with an isolated anti-nucleolin antibody (e.g., human and/or monoclonal) include, but are not limited to: Acute Lymphoblastic Leukemia; Myeloid Leukemia; Acute Myeloid Leukemia; Chronic Myeloid Leukemia; Adrenocortical Carcinoma Adrenocortical Carcinoma; AIDS-Related Cancers; AIDS-Related Lymphoma; Anal Cancer; Astrocytoma, Childhood Cerebellar; Astrocytoma, Childhood Cerebral; Basal Cell Carcinoma; Bile Duct Cancer, Extrahepatic; Bladder Cancer; Bladder Cancer; Bone Cancer, osteosarcoma/Malignant Fibrous Histiocytoma; Brain Stem Glioma; Brain Tumor; Brain Tumor, Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer, Female; Breast Cancer, Male; Bronchial Adenomas/Carcinoids; Burkitt's Lymphoma; Carcinoid Tumor; Central Nervous System Lymphoma; Cerebellar Astrocytoma; Cerebral Astrocytoma/Malignant Glioma; Cervical Cancer; Chronic Lymphocytic Leukemia; Chronic Myelogenous Leukemia; Chronic Myeloproliferative Disorders; Colon Cancer; Colorectal Cancer; Cutaneous T-Cell Lymphoma; B-Cell Lymphoma Endometrial Cancer; Ependymoma; Esophageal Cancer; Esophageal Cancer; Ewing's Family of Tumors; Extracranial Germ Cell Tumor; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma; Hodgkin's Lymphoma During Pregnancy; Hypopharyngeal Cancer; Hypothalamic and Visual Pathway Glioma; Intraocular Melanoma; Islet Cell Carcinoma (Endocrine Pancreas); Kaposi's Sarcoma; Kidney (Renal Cell) Cancer; Kidney Cancer; Laryngeal Cancer; Leukemia, Acute Lymphoblastic; Leukemia, Acute Lymphoblastic; Leukemia, Acute Myeloid; Leukemia, Acute Myeloid; Leukemia, Chronic Lymphocytic; Leukemia; Chronic Myelogenous; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt's; Lymphoma, Cutaneous T-Cell, see Mycosis Fungoides and Sezary Syndrome; Lymphoma, Hodgkin's; Lymphoma, Hodgkin's During Pregnancy; Lymphoma, Non-Hodgkin's; Lymphoma, Non-Hodgkin's During Pregnancy; Lymphoma, Primary Central Nervous System; Macroglobulinemia, Waldenstrom's; Malignant Fibrous Histiocytoma of Bone/Osteosarcoma; Medulloblastoma; Melanoma; Melanoma, Intraocular (Eye); Merkel Cell Carcinoma; Mesothelioma, Adult Malignant; Mesothelioma; Metastatic Squamous Neck Cancer with Occult Primary; Multiple Endocrine Neoplasia Syndrome; Multiple Myeloma/Plasma Cell Neoplasm' Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Hodgkin's Lymphoma During Pregnancy; Oral Cancer; Oral Cavity Cancer, Lip and; Oropharyngeal Cancer; Osteosarcoma/Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer; Pancreatic Cancer, Islet Cell; Parathyroid Cancer; Penile Cancer; Pheochromocytoma; Pineoblastoma and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Prostate Cancer; Rectal Cancer; Renal Cell (Kidney) Cancer; Renal Cell (Kidney) Cancer; Renal Pelvis and Ureter, Transitional Cell Cancer; Retinoblastoma; Rhabdomyosarcoma; Salivary Gland Cancer; Salivary Gland Cancer; Sarcoma, Ewing's Family of Tumors; Sarcoma, Kaposi's; Sarcoma, Soft Tissue; Sarcoma, Soft Tissue; Sarcoma, Uterine; Sezary Syndrome; Skin Cancer (non-Melanoma); Skin Cancer; Skin Cancer (Melanoma); Skin Carcinoma, Merkel Cell; Small Cell Lung Cancer; Small Intestine Cancer; Soft Tissue Sarcoma; Soft Tissue Sarcoma; Squamous Cell Carcinoma, see Skin Cancer (non-Melanoma); Squamous Neck Cancer with Occult Primary, Metastatic; Stomach (Gastric) Cancer; Stomach (Gastric) Cancer; Supratentorial Primitive Neuroectodermal Tumors; T-Cell Lymphoma, Cutaneous, see Mycosis Fungoides and Sezary Syndrome; Testicular Cancer; Thymoma; Thymoma and Thymic Carcinoma; Thyroid Cancer; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Cancer, Endometrial; Uterine Sarcoma; Vaginal Cancer; Visual Pathway and Hypothalamic Glioma; Vulvar Cancer; Waldenstrom's Macroglobulinemia; and Wilms' Tumor.

Cancer cells known to express nucleolin include lung cancers (e.g., non-small cell lung cancers), breast cancers, prostate cancers, colon cancers, pancreatic cancers, renal cell carcinomas, ovarian cancers, leukemias (e.g., AML, CLL), melanomas, glioblastomas, neuroblastomas, sarcomas and gastric cancers. In addition, non-cancer cells that express nucleolin include immune cells such as dendritic cells, peripheral blood monocytes, macrophages, and glial cells, as well as vascular smooth muscle cells and endothelial cells. In some embodiments, an antibody of the present disclosure is used in a treatment for subjects with hyperimmune and hyper-angiogenic diseases, the latter being described in U.S. Patent Publication No. 2009/0191244, incorporated herein by reference.

6. CERTAIN ANTIBODY PROPERTIES

6.1. Mutation Frequency

An antibody disclosed herein can comprise a heavy chain sequence with a mutation frequency of at least about 5%, 6%, 7%, 8%, 9%, 10%, 11%, 12%, 13%, 14%, 15%, 16%, 17%, 18%, 19%, or 20%, or higher from a germline sequence. The antibodies can comprise a CDR3 region that is a light chain sequence with a mutation frequency of at least about 5%, 6%, 7%, 8%, 9%, 10%, 11%, 12%, 13%, 14%, 15%, 16%, 17%, 18%, 19%, or 20%, or higher from a germline sequence. The antibodies can comprise a heavy chain and a light chain sequence with a mutation frequency of at least about 5%, 6%, 7%, 8%, 9%, 10%, 11%, 12%, 13%, 14%, 15%, 16%, 17%, 18%, 19%, or 20%, or higher from a germline sequence. The antibodies can comprise a $V_H$ region from a $V_H$ family selected from the group consisting of any one of $V_H$ family 4-59.

6.2. Heavy and Light Chain Lengths

An antibody disclosed herein can comprise a CDR3 region that is a length of at least about 10, 11, 12, 13, 14, 15, 16, 17, 18, 19, 20, 21, 22, 23, 24, 25, 26, 27, 28, 29, or 30 amino acids in length. The antibodies can comprise a CDR3 region that is at least about 18 amino acids in length.

An antibody disclosed herein can comprise a deletion at an end of a light chain. The antibodies can comprise a deletion of 3 or more amino acids at an end of the light chain. The antibodies can comprise a deletion of 7 or less amino acids at an end of the light chain. The antibodies can comprise a deletion of 3, 4, 5, 6, or 7 amino acids at an end of the light chain.

An antibody disclosed herein can comprise an insertion in a light chain. The antibodies of can comprise an insertion of 1, 2, 3, 4, 5, 6, 7, 8, 9, or 10, or more amino acids in the light chain. The antibodies can comprise an insertion of 3 amino acids in the light chain.

6.3. Affinity

Affinity is the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, including those described herein. Specific illustrative and exemplary embodiments for measuring binding affinity are described in the following.

In some embodiments, an antibody disclosed herein has a dissociation constant ($K_D$) of about 1 µM, 100 nM, 10 nM, 5 nM, 2 nM, 1 nM, 0.5 nM, 0.1 nM, 0.05 nM, 0.01 nM, or 0.001 nM or less (e.g., 10'M or less, e.g., from $10^{-8}$M to $10^{-13}$M, e.g., from $10^{-9}$M to $10^{-13}$ M) for human nucleolin. An affinity matured antibody is an antibody with one or more alterations in one or more hypervariable regions (HVRs), compared to a parent antibody which does not possess such alterations, such alterations resulting in an improvement in the affinity of the antibody for antigen. These antibodies can bind to human nucleolin with a $K_D$ of about $5 \times 10^{-9}$M, $2 \times 10^{-9}$M, $1 \times 10^{-9}$M, $5 \times 10^{-10}$ M, $2 \times 10^{-9}$M, $1 \times 10^{-10}$ M, $5 \times 10^{-11}$M, $1 \times 10^{-11}$M, $5 \times 10^{-12}$ M, $1 \times 10^{-12}$ M, or less.

$K_D$ can be measured by any suitable assay. For example, $K_D$ can be measured by a radiolabeled antigen binding assay (RIA) (See, e.g., Chen et al., J. Mol. Biol. 293:865-881 (1999); Presta et al., Cancer Res. 57:4593-4599 (1997)). For example, $K_D$ can be measured using surface plasmon resonance assays (e.g., using a BIACORE®-2000 or a BIACORE®-3000).

6.4. Cysteine Engineered Antibody Variants

In some embodiments, it may be desirable to create cysteine engineered antibodies, e.g., "thioMAbs," in which one or more residues of an antibody are substituted with cysteine residues. In some embodiments, the substituted residues occur at accessible sites of the antibody. Reactive thiol groups can be positioned at sites for conjugation to other moieties, such as drug moieties or linker-drug moieties, to create an immunoconjugate. In some embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described (See, e.g., U.S. Pat. No. 7,521,541).

6.5. Antibody Derivatives

In some embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. The number of polymers attached to the antibody may vary, and if two or more polymers are attached, they can be the same or different molecules.

In some embodiments, conjugates of an antibody and nonproteinaceous moiety that may be selectively heated by exposure to radiation are provided. In some embodiments, the nonproteinaceous moiety is a carbon nanotube (See, e.g., Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

7. RECOMBINANT METHODS AND COMPOSITIONS

Antibodies may be produced using recombinant methods and compositions (See, e.g., U.S. Pat. No. 4,816,567). In some embodiments, an isolated nucleic acid encoding a nucleolin antibody described herein is provided. Such nucleic acid may encode an amino acid sequence comprising the VL and/or an amino acid sequence comprising the VH of the antibody. In a further embodiment, one or more vectors comprising such nucleic acid are provided. A vector is a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked.

In some embodiments, a host cell comprising such nucleic acid is provided. Host cells are cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In one such embodiment, a host cell comprises (e.g., has been transformed with) a vector comprising a nucleic acid that encodes an amino acid sequence comprising the VL of the antibody and an amino acid sequence comprising the VH of the antibody or a first vector comprising a nucleic acid that encodes an amino acid sequence comprising the VL of the antibody and a second vector comprising a nucleic acid that encodes an amino acid sequence comprising the VH of the antibody. In some embodiments, the host cell is eukaryotic, e.g., a Chinese Hamster Ovary (CHO) cell or lymphoid cell (e.g., Y0, NS0, Sp20 cell). In some embodiments, a method of making a nucleolin antibody is provided, wherein the method comprises culturing a host cell comprising a nucleic acid encoding the antibody, as provided above, under conditions suitable for expression of the antibody, and optionally recovering the antibody from the host cell or host cell culture medium.

For recombinant production of a nucleolin antibody, an isolated nucleic acid encoding an antibody, e.g., as described above, is inserted into one or more vectors for further cloning and/or expression in a host cell. Such nucleic acid may be readily isolated and sequenced using conventional procedures.

Suitable host cells for cloning or expression of antibody-encoding vectors include prokaryotic or eukaryotic cells described herein. For example, antibodies may be produced in bacteria, e.g., when glycosylation and Fc effector function are not needed (See, e.g., U.S. Pat. Nos. 5,648,237, 5,789,199, and 5,840,523; Charlton, Methods in Molecular Biology, Vol. 248, pp. 245-254 (2003)). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors (See, e.g., Gerngross, Nat. Biotech. 22:1409-1414 (2004), and Li et al., Nat. Biotech. 24:210-215 (2006)). Suitable host cells for the expression of glycosylated antibody are also derived from multicellular organisms, including invertebrates and vertebrates. Examples of invertebrates include plant and insect cells (See, e.g., U.S. Pat. Nos. 5,959,177, 6,040,498, 6,420,548, 7,125,978, and 6,417,429). Examples of vertebrate cells include mammalian cell lines, monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TR1 cells; MRC 5 cells; FS4 cells; Chinese hamster ovary (CHO) cells, including DHFR$^-$ CHO cells; and myeloma cell lines such as Y0, NS0 and Sp2/0. (See, e.g., Yazaki and Wu, Methods in Molecular Biology, Vol. 248, pp. 255-268 (2003).

8. EXAMPLES

Example 1. Subcloning and Purification of Antibody CP1 from Human B Cells (CP1)

Cells from each parental B-cell lines were thawed and expanded. The cells were cultured in regular growth media (RPMI) supplemented with 10% FBS. The culture was subcloned by seeding 96-well plates at three different densities (2 cells, 1 cell, and 0.5 cells/well). The clonal outgrowth was monitored over at least a 2 week timeframe. An antigen-specific ELISA ("nucleolin ELISA") was used to detect anti-nucleolin antibodies and screen single-cell clones. Positive wells were counter-screened using an anti-human IgG ELISA to estimate the antibody titers in the positive wells. Up to ten positive subclones per parental B cell line were expanded and cryopreserved in banks of at least twenty vials each. Cells were frozen in RPMI media containing 5% DMSO. A TRIZOL reagent extract was prepared from $1 \times 10^7$ cells from each subclone frozen above at the time of banking. RNA and oligo-dT primed cDNA were prepared from each sample. The cDNA from each TRIZOL extract was polyadenylated and used as template in a PCR reaction using 3' specific heavy chain and light chain constant region primers and oligo-dT as the 5' primer so as to amplify the variable regions of the expressed antibodies. The 500 bp inserts were gel-isolated and ligated into pBluescript. For each of the insert sets, six VH inserts and six VL inserts were sequenced and aligned.

Frozen culture was thawed and expanded. B cell supernatant preparation: Cells were seeded at ~[0.8×10$^6$ cells/ml] into 28×T225 flasks (A) (75 ml each, 2100 ml total) and 10×T75 flasks (B) (40 ml each, 400 ml total) in 75:25 AIM media: RPMI media (1% antibiotics), total 2500 ml. When the cells reached a total volume of ~4,400 ml (36×T225 flasks), supernatant CP1 was harvested with CENTRICON centrifugation. Cell #: mean cell number=8.8×10$^5$ cells/ml Mean cell viability=70.5% Centrifuge Filtration: CENTRICON Plus-70 Centrifugal filter device, 100K. Melon Gel Purification of IgG: MELON Gel IgG Purification 200 ml resin (or 1 L total volume), Thermo Scientific (cat #PI-45214). Total 1 L gel solution (containing 20% beads slurry, 200 ml). Combined 400 ml used gel solution+600 ml unused gel solution ~1 L total.

Example 2. Production of Antibody CP1 from Recombinant Cells (CP1(RC))

CHO3E7 (Chinese hamster ovary) cells with an initial density of 2.1×10$^6$ cells/mL, in a culture medium of F17 supplemented with 0.1% Pluronic F-68, 4 mM GlutaMAX, was transfected with either CP1 gamma heavy chain/kappa light chain or CP1 gamma heavy chain/lambda light chain.

cDNA encoding was synthetically produced with codon optimization for mammalian cell expression and cloned into expression vector pTT5 at the indicated restriction sites by standard methods. Two, 30 mL cultures of CHO3E7 cells in 125 mL shake flasks were transfected with 1 mg of plasmid DNA/L culture using PolyPlus linear Q-PEI at a 1:4 (w/v) DNA:PEI ratio. Cultures were supplemented with 4.5 mL CD Efficient Feed B (Life Technologies) 24 hours post transfection. Culture parameters were monitored using a VICELL XR device for density and viability.

Culture supernatants were harvested 10 days post transfection (6 days for the second transfection) via centrifugation for 5 minutes at 1000×g. The conditioned culture supernatants (CCS) were clarified by centrifugation for 30 minutes at 9100×g, filter sterilized with a 0.2 μm PES filter system, and stored at 4° C.

Figure 11:
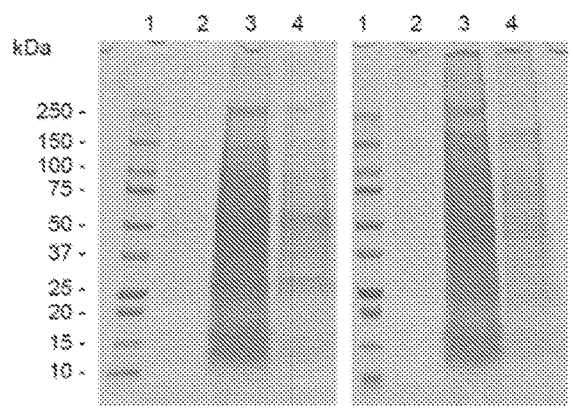
FIG. 11 is a set of SDS-PAGE images verifying protein/antibody expression in Example 2.
Figure 11:
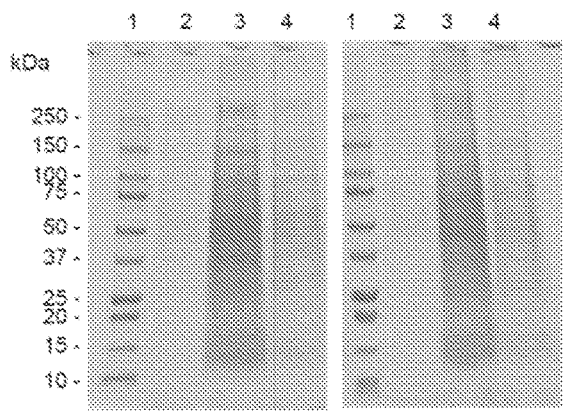
Figure 12:
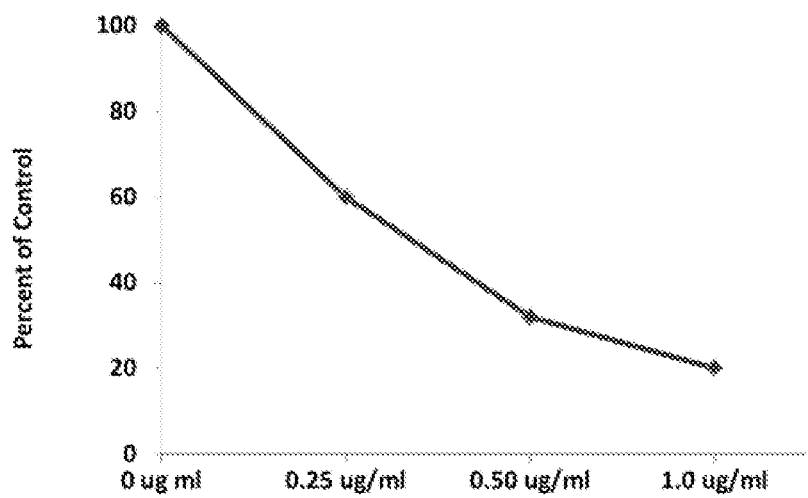
FIG. 12 is a line graph showing effect of CP1 recombinant kappa light chain on the viability of MV4-11 cells.

Protein expression was analyzed via reducing and non-reducing SDS-PAGE. See FIG. 11. Expression verification SDS-PAGE. Forty microliter samples of conditioned culture supernatant (CCS) were evaluated via reducing (left panels) and non-reducing (right panels) SDS-PAGE on 4-20% Tris-glycine TGX gels (Bio-Rad) and stained with Instant Blue gel stain.

CP1(RC) bound tightly to human recombinant nucleolin (Kd=2.6±0.7 nM, SEM.) and to plasma membrane nucleolin of human tumor cells. Confocal microscopy of Panc-1 and DU-145 tumor cells incubated at 37° C. with CP1(RC) revealed punctate localization of the antibody in the plasma membranes of these cells and internalization of the antibody into the cytoplasm. The localization of the antibody within foci in the plasma membrane suggested that the antibody was bound to nucleolin that was incorporated into lipid rafts within the plasma membrane.

Plasmid isolation and transient expression in CHO3E7 cells at the 6 L culture scale. The goal was to isolate endotoxin-free expression plasmid DNA encoding CP1 gamma heavy chain. 6 L of CHO3E7 cells was transiently transfect with gamma heavy chain and kappa light chain plasmid DNA using linear PEI. The culture parameters were monitored, and the conditioned culture supernatant (CCS) was harvested when the viability has dropped to ~85-90% (targeting 90%). It was expected to hit viability target 3-4 days post transfection. Protein expression in the CCS was analyzed by reducing and non-reducing SDS-PAGE. Clarified CCS was sterile filtered and stored at 4° C.

Example 3. Binding to Recombinant Nucleolin by ELISA Assay

Reagents: Goat anti-human IgG Ab-HRP Antibody produced by Santa Cruz as nonspecific IgG Control, recombinant nucleolin quantitation by nanodrop (Yoko Otake), and femto-ELISA-HRP kit.

Preparation: 100 μl binding buffer (control) or recombinant nucleolin (containing 200, 400 or 800 ng) was added to designated wells in an Immuno 96 well plate. The plate was incubated for 1 h on orbital shaker @ 100 rpm at room temp. After 1 h incubation, the plate was carefully inverted to empty and gently tap out residual liquid. 200 μl diluted 1×NAP-blocker was added to each well and incubate the plate for 15 min on orbital shaker @ 100 rpm. After incubation, carefully invert the plate to empty and gently tap out residual liquid.

Primary Antibody incubation: 100 μl of serial diluted supernatant solution in blocking buffer was incubated for 1h at room temp on an orbital shaker @ 100 rpm. After incubation, the plate was carefully inverted to empty and gently tap out residual liquid. To wash out the antibody, each well was filled with 1× femto-TBST (200 μl) and waited for 30 sec then the plate was inverted and tapped to empty the residual liquid from each well.

Secondary Antibody Incubation: 100 μl of *1→500 diluted 2° anti-human IgG Ab-HRP stock was incubated at RT for 1 h on an orbital shaker @ 100 rpm. To wash out the antibody, each well was filled with 1× femto-TBST (200 μl) and waited for 30 sec then the plate was inverted and tapped to empty the residual liquid from each well.

Preparation for Reading: 100 μl of femto-ELISA-HRP substrate was added into each well. A soluble blue color developed, which is read at 620 nm using substrate as a blank. Monitoring was done every 10 min for 1 h.

Figure 4:
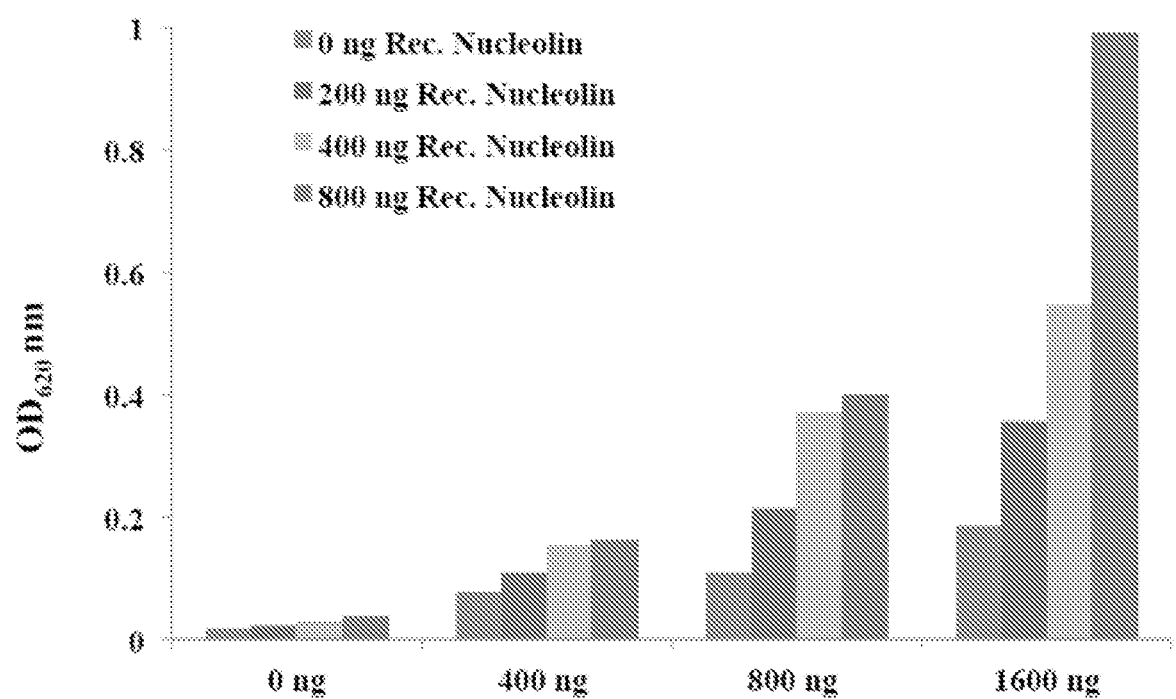
FIG. 4 is a bar graph showing binding of CP1 to human recombinant nucleolin. Various amounts of human recombinant nucleolin were bound to a 96 well plate. The plate was washed with blocking buffer and then various amounts of antibody CP1 or human IgG control antibody were added to the wells. The wells were washed with blocking buffer to remove the unbound antibody, and then incubated with a HRP conjugated secondary antibody specific for human IgG1.

Results: ELISA Analysis of the binding of antibody CP1 to truncated human recombinant nucleolin with an N-terminal deletion (Δ1-283) and 6x-His (SEQ ID NO:94) yields an equilibrium dissociation constant of 2.6±0.7 nM S.E.M, N=4, see FIG. 4.

Example 4. Activity/Potency Tests

Melon Gel Purified Antibodies on MCF-7 and MCF-10A cells by Cell Counting/TBE at 96 h. Antibody was spin column purified by Melon gel (CP expt 407); IgG conc. [533.26 μg/ml] (CP expt 409); ~2.0 ml; 1×PBS buffer with 100 mM arginine. MCF7 cells and MCF10A cells were seeded at [$1\times10^4$ cells/ml] (or $2\times10^3$ cells/200 μl per well). MCF-7 and MCF-10A cells were set up at [$1\times10^4$ cells/ml]$_{1\times}$ (or $2\times10^3$ cells/200 μl per well) in a 96 well plate (MCF7 cells A-D, MCF10A cells E-H). For 25 ml at [$1\times10^4$ cells/ml]$_{1\times}$, collect $2.5\times10^5$ cells. 200 μl of cell solution were seeded per well of a 96 well each cell line as indicated below. Incubated overnight. Next day, confluency checked: ~30% confluency for MCF7 cells, ~10% confluency for MCF10A cells.

A 96 h drug treatment was conducted using the following protocol. For ½ plate of MCF7 cells, make up 5 ml media with 20% human serum (type AB) using appropriate media (RPMI with 1% antibiotics) or 1 ml of human serum and 4 ml RPMI media for MCF7 cells, or HuMEC complete medium for MCF10A cells. Test various concentrations of CP1M4.2 at 0, 0.1, 0.25, 0.5, 1, 2, and 4 μg/ml IgG in triplicate. First make up the stock solution of CP1 at [4 μg/ml]$_{1\times}$ (or [8 μg/ml]$_{2\times}$) (0.7 ml) in RPMI media-1% antibiotics for MCF7 cells or HuMEC complete media for MCF10A cells. For IgG control, first make up a stock solution of the same conc. as that of CP1M4 sample [53.26 μg/ml] in the same solution, 1×PBS buffer with 100 mM arginine. Then, prepare the serial dilution exactly the same as for CP1M4.2 for each cell line (see step 4). Start the drug treatment. Discard all solution (200 μl) by pipetting out. Add 100 μl of media with 20% human serum each well (×3). Add 100 μl of regular media without human serum (e.g., RPMI/ 1% antibiotics), IgG control or supernatant as indicated below in the sample set up. Put back in the incubator. Count cell numbers and perform TBE assay at 96 h (Tuesday) to determine the effects of antibodies CP1 and the control IgG antibody.

Cytotoxicity: at Time=96 h. The following protocol was used to assay cytotoxicity. At 96 h, check cell morphology under microscope briefly. Working with a group of sample at a time (e.g., IgG controls), remove the supernatant. Add *30 μl trypsin to each well, and incubate for 15 min. Add 170 μl PBS (total volume 200 μl. Transfer cell solution to 0.5 ml tube and pipet well to break up the cells. Into another 0.5 ml, add 10 μl 0.2% Trypan blue in PBS (filtered). Working with 2 samples, add in 20 µl of cell solution to 10 µl 0.2% Trypan blue. Mix well, load onto a chamber, then incubate for 1 min before counting viability and live cell numbers with Cellometer (e.g., 20 µl per sample).

Figure 7:
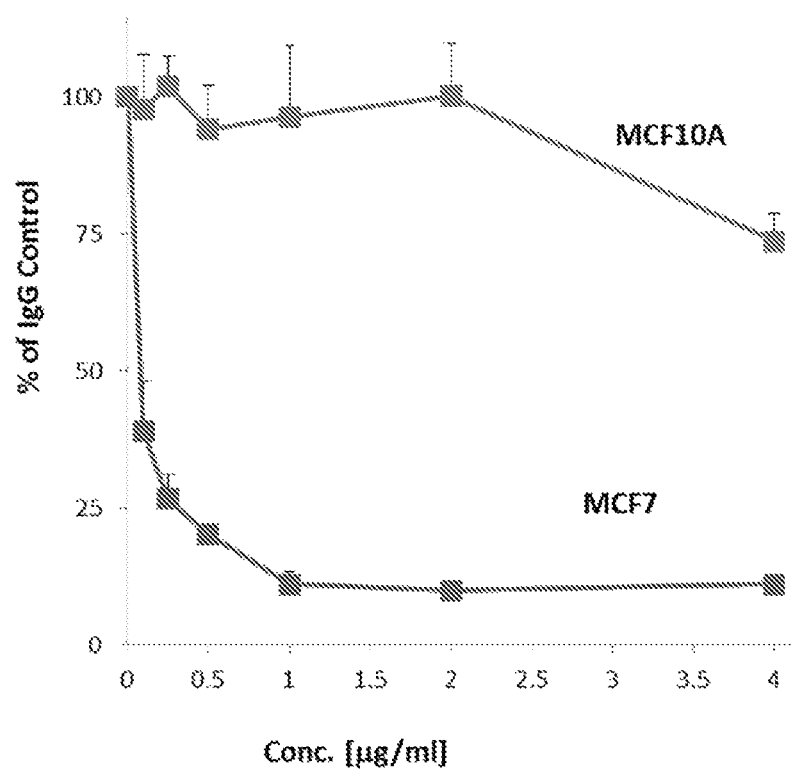
FIG. 7 is a line graph showing effects of CP1 on the viability MCF7 breast cancer cells and MCF10A normal breast epithelium cells.

Results are shown in FIG. 7. Compared to IgG control, CP1 has potent killing activity to MCF7 breast cancer cells, but negligible toxicity to normal breast cells.

Comparison with Aptamer AS1411

MCF-7 cells were incubated for 96 hours with either the aptamer AS1411 (A) or with an anti-nucleolin antibody consistent with current claims (B) at a concentration recited below. Cell viability was measured using a chromogenic assay involves the biological reduction by viable cells of the tetrazolium compound [3-(4,5-dimethylthiazol-2-yl)-5-(3-carboxymethoxyphenyl)-2-(4-sulfophenyl)-2H-tetrazolium (or MTS assay) (A) or by the trypan blue exclusion assay (B). Results are the means±S.E.M. (Standard Error of Mean) of six experiments (A) or 3 experiments (B).

Figure 13:
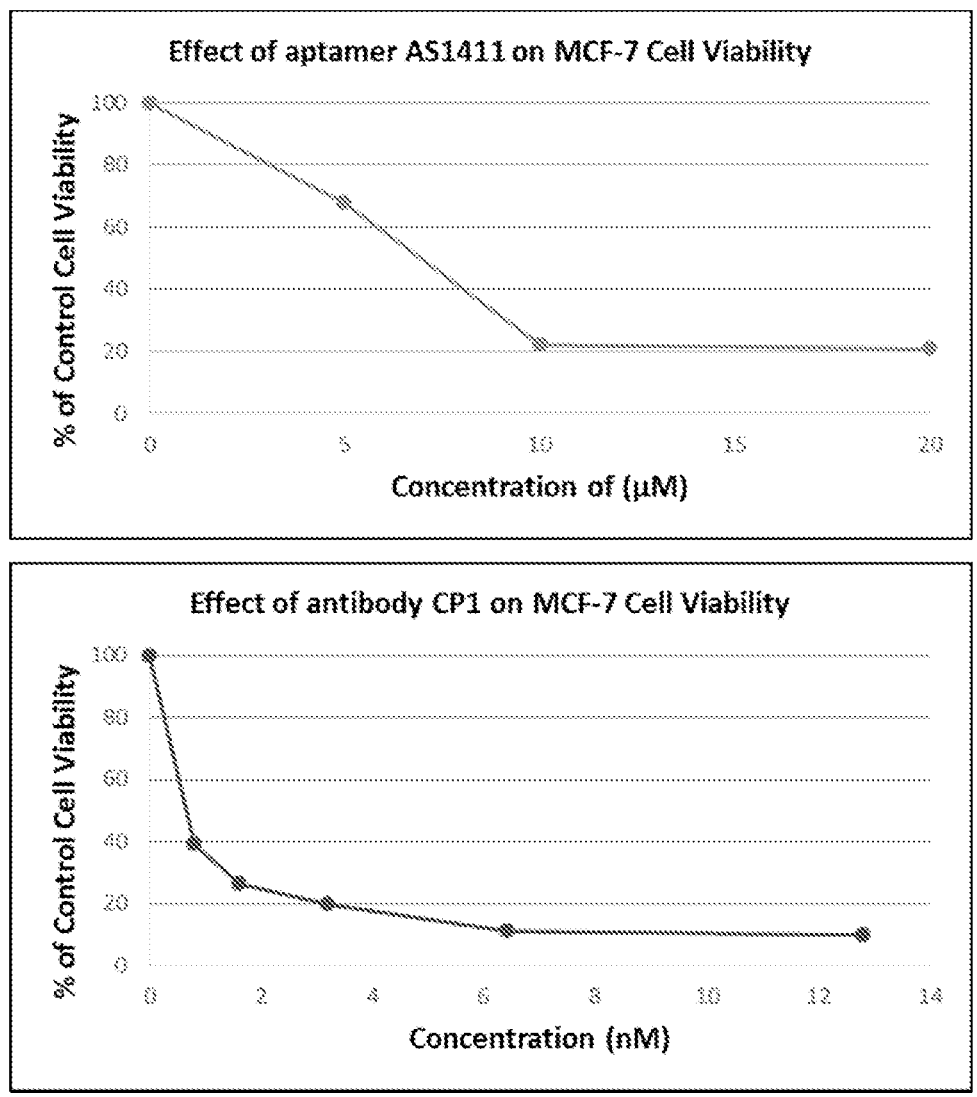
FIG. 13 is a line graft showing comparing effects of aptamer AS1411 and CP1 on the viability of human MCF-7 breast cancer cells.

As a result, the concentration of AS1411 required to reduce MCF-7 cell viability to 50% ($IC_{50}$) was about 7 while the $IC_{50}$ value of the claimed antibody to MCF-7 cells was as low as about 0.8 nM or 0.0008 shown in FIG. 13. Thus, the claimed antibody was about 9000 times more potent than AS1411 in killing MCF-7 cells.

Example 5. Effects of Antibodies on MV411 Human Leukemia Xenograft Model in Nude Mice Female NCr nu/nu mice (8-12 week of age; n=40) were injected with $1\times10^7$ MV411 tumor cells in 50% (v/v) Matrigel subcutaneously in their flanks. When tumors reach an average size of 100-150 $mm^3$, a pair match was performed to sort mice into two groups of ten each. Mice were then treated with IgG isotype control antibody (Group 1) or an antibody as claimed such as CP1 (Group 2). Each group had 10 female CRL nnu/nu mice and was administered intravenously with a dosage of 10 mg/kg in a 0.1 ml injection volume on days 1, 4, 7, 10, 13, 16. Animals were monitored individually. Body Weight measurements were taken daily for the first week and then biweekly. Caliper measurements of tumor sizes were taken biweekly. The endpoint of the study was a tumor volume of 2000 $mm^3$ or 76 days, whichever came first. When the endpoint was reached, the animals were euthanized.

CP1 was well tolerated with the only adverse event being a 16% transient loss in mean body weight. CBC was normal. Necropsy results of all major organs were normal.

Figure 14:
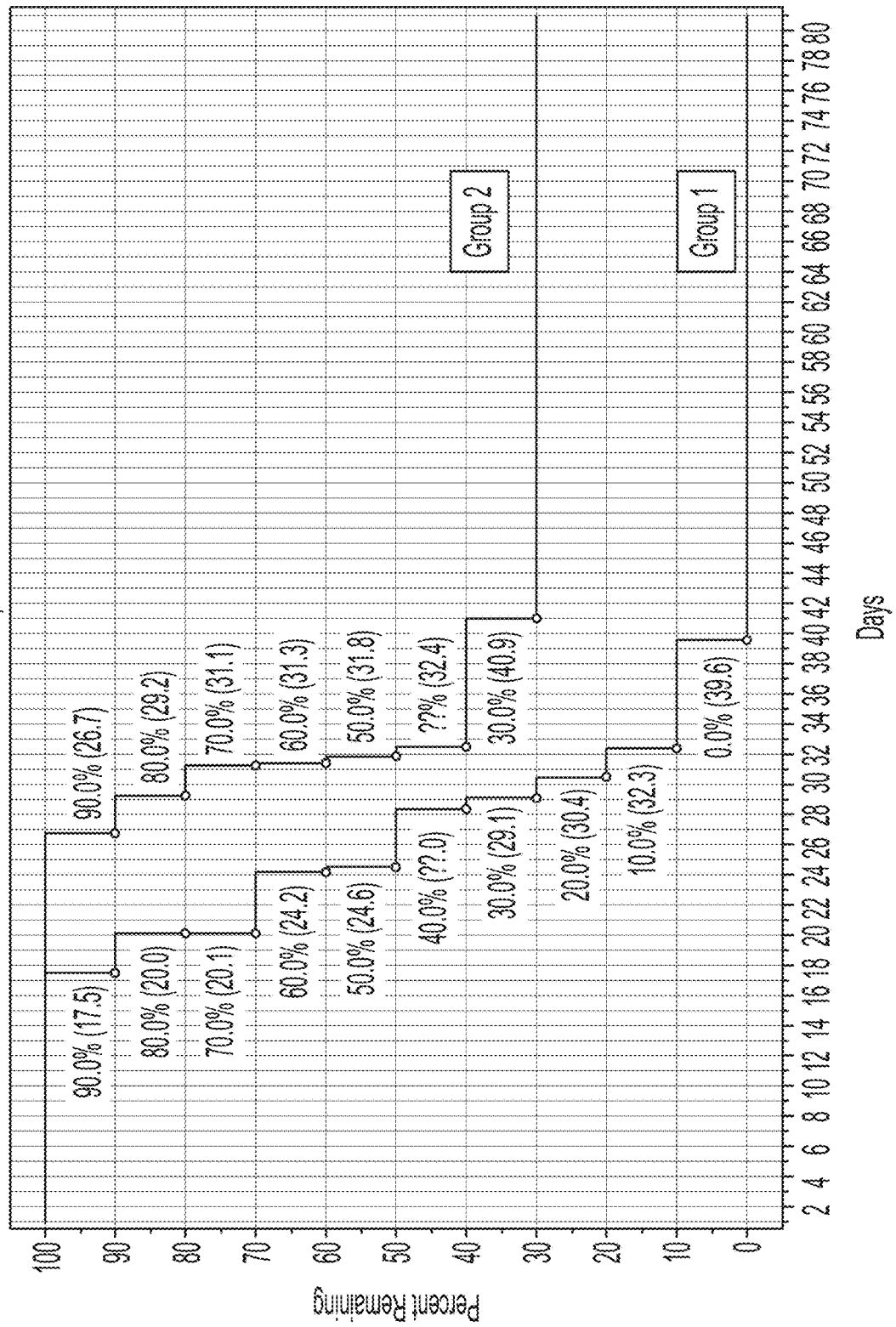
FIG. 14 is a Kaplan-Meier plot showing effects of CP1—30% long term survivors in an MV411 human leukemia xenograft model with nude mice.

In this MV4-11 human xenograft mouse model, CP1 treatment resulted in 30% long-term survivors (Hazard ratios of 0.22-0.29) without inducing any serious toxicity to the mice. This was a statistically significant increase in survival of nude mice treated with CP1 compared to isotype control antibody with no significant organ or hematologic toxicity. No other biologic is known to show survival benefit in this model as a single agent. FIG. 14 shows that in Group 2, 30% of the mice survived for 80 days. Even more surprisingly, 20% of the mice showed complete tumor regression by about Day 40 (data not shown). In marked contrast, all of the mice in the control group (Group 1) showed rapid tumor growth to an endpoint volume 2000 $mm^3$ and had to be euthanized on about Day 40.

Figure 15A:
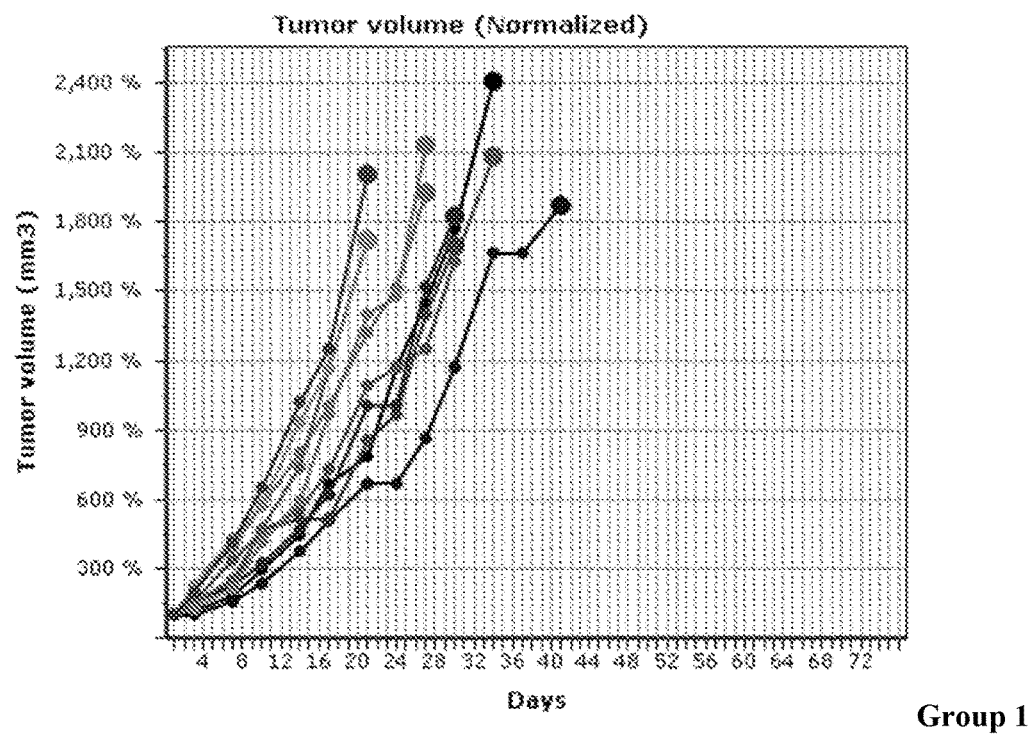
FIG. 15A is a line chart showing tumor volume changes in mice of Group 1 (10 mice): Control (10 mg/kg, iv, days 1, 4, 7, 10, 13, 16).
Figure 15B:
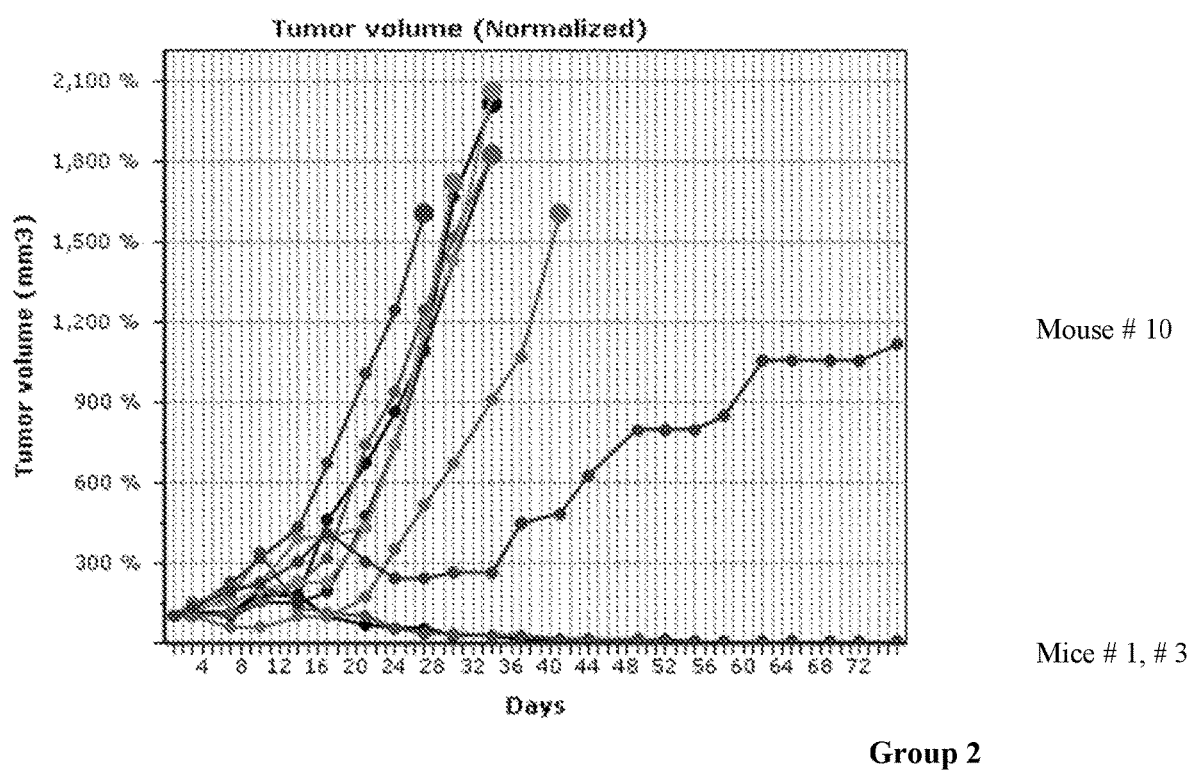
FIG. 15B is a line chart showing tumor volume changes in mice of Group 2 (10 mice): CP1 (10 mg/kg, iv, days 1, 4, 7, 10, 13, 16).

FIG. 15A and FIG. 15B are another way of comparison of Group 1 and Group 2 in view of tumor volume changes. Surprisingly 3 out of the 10 treated mice (Group 2) survived for at least 76 days and more surprisingly, two of the survived mice showed complete tumor regression by about Day 40. In marked contrast, all of the 10 mice in the control group (Group 1) showed rapid tumor growth and had to be euthanized on about Day 40. FIG. 15A shows that all the mice in Group 1 showed rapid tumor growth after treatment with an IgG control antibody. In contrast, FIG. 15B shows that the tumor volume of mice #1 and #3 in Group 2 dropped to non-detectable levels by about Day 40 after treatment with a claimed antibody. Mice #10 also survived and its tumor volume became generally static from about Day 60.

Example 6. Methods of Predicting CDRs

Amino acid numbering based on framework and complementary determining regions (CDR) are defined by one of the following:

Rosie Rosetta. Reference: Lyskov S, et al., "Serverification of Molecular Modeling Applications: The Rosetta Online Server That Includes Everyone (ROSIE)". PLoS One. 2013 May 22; 8(5):e63906. doi: 10.1371/journal.pone.0063906. Print 2013. The ROSIE app interface to the RosettaAntibody3 program was used to model the 3-D structure of the hypervariable region of antibody CP1 and identify the six CDRs. The first stage utilizes canonical template selection and assembly based on the Chothia definition described below and the lowest energy structures. They are assembled using a Rosetta protocol, resulting in a crude structure. In the second stage, CDR-H3 is remodeled de novo. Paratope side chains and loop backbones were refined simultaneously based on the Paratome method described below. CDR-H3 contained less than 10 amino acids, which indicates that the root mean square deviation is approximately 1.5 Angstroms and the model is highly accurate.

Paratome. Reference: Kunik V, et al. (2012). Paratome: An online tool for systematic identification of antigen binding regions in antibodies based on sequence or structure. Nucleic Acids Res. 2012 July; 40(Web Server issue):W521-4. doi: 10.1093/nar/gks480. Epub 2012 Jun. 6. The Paratome web server (www.ofranlab.org/paratome/) was used to identify the six Antibody Binding Regions (ABRs) within the hypervariable region of antibody CP1. The ABRs are similar to CDRs but also contain amino acid side-chains near the CDRs that also contribute to binding of the antibody to the antigen. From the primary structure of antibody CP1, the Paratome web server was able to identify the ABRs of the antibody by comparison to the structural consensus regions within a multiple structure alignment of a non-redundant set of all antibody-antigen complexes.

P.I.G.S. (Prediction of Immunoglobulin Structure) numbering system. Reference: Marcatili P. et al. PIGS: automatic prediction of antibody structures. Bioinformatics 2008 24: 1953.

Chothia Definition. Reference: Chothia C et al. Conformations of immunoglobulin hypervariable regions. Nature 1989 342: 887). The Chothia definition is a scheme for numbering the amino acid residues of the hypervariable regions of antibodies and the beginning and ending of each of the six complementary regions (CDRs) within the hypervariable regions. The scheme is based on the analysis of the canonical structures of numerous antibodies. Using the Chothia definition, we were able to identify the positions of the amino acids at the beginning and ending of the six CDRs and the remaining amino acids within the CDRs by comparison to the primary structure of antibody CP1.

Kabat. Reference: Kabat et al., Sequences of Proteins of Immunological Interest, 5th Ed. Public Health Service, National Institutes of Health, Bethesda, Md., 1991).

A set of rules were followed to identify the CDRs, as published Dr. Andrew C. R. Martin's Bioinformatics Group at University College London in UK, or below.

CDR-L1 (L24-L34)

| | |
|---|---|
| Start | Approx residue 24 |
| Residue before | always a Cys |
| Residue after | always a Trp. Typically Trp-Tyr-Gln, but also, Trp-Leu-Gln, Trp-Phe-Gln, Trp-Tyr-Leu |
| Length | 10 to 17 residues |

CDR-L2 (L50-L56)

| | |
|---|---|
| Start | always 16 residues after the end of L1 |
| Residues before | generally Ile-Tyr, but also, Val-Tyr, Ile-Lys, Ile-Phe |
| Length | always 7 residues (except NEW (7FAB) which has a deletion in this region) |

CDR-L3 (L89-L97)

| | |
|---|---|
| Start | always 33 residues after end of L2 (except NEW (7FAB) which has the deletion at the end of CDR-L2) |
| Residue before | always Cys |
| Residues after | always Phe-Gly-XXX-Gly |
| Length | 7 to 11 residues |

CDR-H1 (H31-H35B)

| | |
|---|---|
| Start | Approx residue 31 |
| Residues before | always Cys-XXX-XXX-XXX |
| Residues after | always a Trp. Typically Trp-Val, but also, Trp-Ile, Trp-Ala |
| Length | 10 to 12 residues [AbM definition]; Chothia definition excludes the last 4 residues |

CDR-H2 (H50-H65)

| | |
|---|---|
| Start | always 15 residues after the end of CDR-H1 |
| Residues before | typically Leu-Glu-Trp-Ile-Gly (SEQ ID NO: 95), but a number of variations |
| Residues after | Lys/Arg-Leu/Ile/Val/Phe/Thr/Ala-Thr/Ser/Ile/Ala |
| Length | Kabat definition 16 to 19 residues; AbM (and recent Chothia) definition ends 7 residues earlier |

CDR-H3 (H95-H102)

| | |
|---|---|
| Start | always 33 residues after end of CDR-H2 (always 2 after a Cys) |
| Residues before | always Cys-XXX-XXX (typically Cys-Ala-Arg) |
| Residues after | always Trp-Gly-XXX-Gly |
| Length | 3 to 25 residues |

IMGT (ImMunoGeneTics). The following rules of IMGT are followed to identify the CDRs. Reference: Lefranc, M.-P., The Immunologist, 7, 132-136 (1999)).

TABLE 3

Definition of the FR and CDR according to IMGT

| | FR1-IMGT | CDR1-IMGT | FR2-IMGT | CDR2-IMGT | FR3-IMGT | Specific to V-REGION of Germline V-GENEs Germline CDR3-IMGT (1) | Specific to V-DOMAIN; for rearranged V-J-GENES and V-D-J-GENES Rearranged CDR3-IMGT (2) | FR4-IMGT (2) |
|---|---|---|---|---|---|---|---|---|
| Amino acid numbering | 1->26 (C 23) | 27->38 | 39->55 (W 41) | 56->65 | 66->104 (C 104) | 105->116 | 105->117 | 118->129 |
| Number of amino acids | 25-26 | 5-12 | 16-17 | 0-10 | 36-39 | 2-12 | 2-13 | 10-12 |

(C 23) 1st-CYS, (W 41) CONSERVED-TRP, (C 104) 2nd-CYS, position 118 corresponds to J-PHE or J-TRP as described in the text. IMGT notes: (1) The germline CDR3-IMGT is specific of the V-REGION of germline V-GENEs. It comprises 0, 1 or 2 nucleotide(s) before the V-HEPTAMER. (2) The rearranged CDR3-IMGT and the FR4-IMGT are specific of the V-DOMAIN (V-J-REGION or V-D-J-REGION). They are characteristic of rearranged V-J-GENEs and V-D-J-GENEs, and corresponding cDNAs and proteins.

Example 7. Methods of Computer Modeling the Binding of Anti-Nucleolin Antibody to Nucleolin ClusPro 2.0 protein-protein docking software (available at cluspro.bu.edu) was utilized to predict the interaction between the Rosetta ROSIE-predicted structure of antibody CP1(RC) and the solution structure of RNA-binding domains (RBD) 1 and 2 of human nucleolin. The solution structure of human nucleolin RBDs 1 and 2, also known as "2KRR", is publically available through the Research Collaboratory for Structural Bioinformatics Protein Data Bank (RCSB PDB).

To begin docking in ClusPro 2.0, the .pdb file containing the Rosetta ROSIE-predicted structure of the antibody was assigned as the "Receptor" and the .pdb file containing the 2KRR structure was assigned as the "Ligand". Under "Advanced Options", "Use Antibody Mode" was selected. In Antibody Mode, ClusPro 2.0 uses an asymmetric potential for docking antibody and antigen pairs. This asymmetric potential was arrived at following the discovery that antibody-antigen interactions do not exhibit high degrees of surface complementarity, as in enzyme-substrate interactions. Rather, antibody-antigen interactions exhibit mostly flat, less hydrophobic interfaces. Finally, since antibodies interact with their antigens via their complementarity-determining regions (CDRs), the option to "Automatically Mask non-CDR Regions" was selected.

To execute docking, ClusPro 2.0 utilizes the protein-protein docking program PIPER, an FFT (fast Fourier transform)-based docking program that uses a structure-based pairwise potential as one component of its energy function; in Antibody Mode, the asymmetric potential is used. While the antibody is held in place on a three-dimensional grid, the ligand is rotated in increments of 1.0 Å every 5°, resulting in 70,000 rotations total. For each rotation, the ligand is translated in x,y,z relative to the receptor on a grid. The lowest scoring 1000 structures/translation combinations from PIPER are then exported to ClusPro 2.0, where they are clustered within a 9 Angstrom C-alpha rmsd radius. This means that ClusPro 2.0 finds the ligand position with the most "neighbors" within 9 Angstroms, and it becomes a cluster center, and its neighbors the members of the cluster. These are then removed from the set and ClusPro 2.0 then looks for a second cluster center, and so on. The docking predictions can be ranked by cluster size. Those with the highest number of cluster members scored better than those with fewer. The model having the highest number of cluster members was chosen as the working model.

CP1 and CP1(RC) bind to cell surface nucleolin and the complex appears to utilize lipid raft mediated endocytosis for cellular entry. In the cytoplasm CP1 and CP1(RC) bind to RNA binding domains 1 and 2 of human nucleolin.

Figure 16:
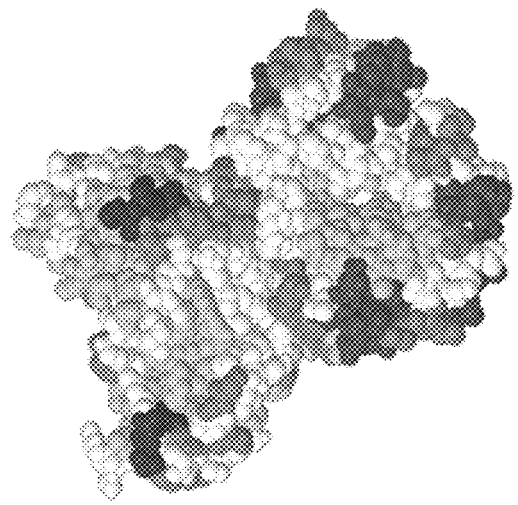
FIG. 16 is an image of molecular model of the binding of antibody CP1 to human nucleolin.
Figure 16:
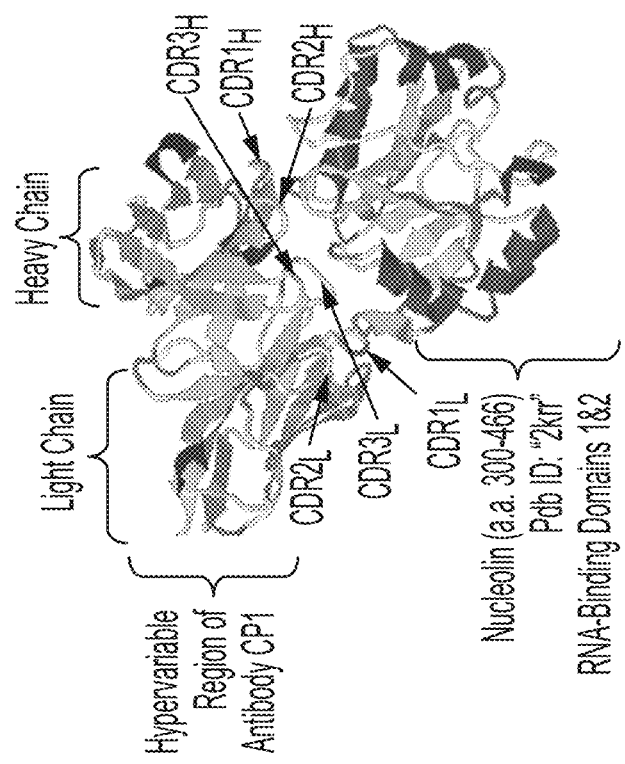

FIG. 16 is an image of molecular model of the binding of antibody CP1(RC) to human nucleolin, where the CDRs in contact with nucleolin are labeled. ClusPro 2.0 protein-docking software was utilized in antibody mode to predict the interaction between the hypervariable region of CP1(RC) and the structures of various nucleolin fragments in the Protein Data Bank (PDB). The model as shown was obtained with the binding of CP1(RC) (its CDR predictions are done with Rosie Rosetta) and the RNA-binding domains 1 and 2 (RBD 1 & 2) of human nucleolin (PDB 2krr, amino acid sequence of residues 300-466 of SEQ ID NO: 20). Some of the closest distances between residues in antibody CDRs and residues of nucleolin (NCL) are listed in Table 4.

TABLE 4

Distances of select amino acids in the nucleolin-antibody CP1(RC) binding model.

| | Distance | Antibody Residue | Side Chain Property | 2KRR Residue | Side Chain Property | NCL Residue # |
|---|---|---|---|---|---|---|
| Light Chain CDR1 | 0.266 nm | [ARG]31:L.HH12 #284 | Basic, electrically charged | [GLU]154:A.OE2 #1485 | Polar | E453 |
| | 0.351 nm | [TRP]32:L.HE1 #300 | Nonpolar | [ARG]158:A.HH12 #1522 | Basic, electrically charged | R457 |
| | 0.333 nm | [TRP]32:L.NE1 #299 | Nonpolar | [ARG]158:A.HH12 #1522 | Basic, electrically charged | R457 |
| | 0.198 nm | [ARG]31:L.HH22 #287 | Basic, electrically charged | [GLU]154:A.OE1 #1484 | Polar | E453 |
| Light Chain CDR2 | 0.172 nm | [LYS]50:L.HZ3 #490 | Basic, electrically charged | [ASP]156:A.O #1505 | Acidic, electrically charged | D455 |
| | 0.188 nm | [LYS]50:L.HZ2 #489 | Basic, electrically charged | [ASP]156:A.OD1 #1502 | Acidic, electrically charged | D455 |
| | 0.185 nm | [LYS]50:L.HZ2 #489 | Basic, electrically charged | [ASP]156:A.OD2 #1503 | Acidic, electrically charged | D455 |
| Light Chain CDR3 | 0.164 nm | [TYR]94:L.OH #897 | Polar | [LYS]49:A.HZ3 #456 | Basic, electrically charged | K348 |
| | 0.245 nm | [TYR]94:L.HH #898 | Polar | [LYS]49:A.HZ3 #456 | Basic, electrically charged | K348 |
| Heavy Chain CDR1 | 0.172 nm | [TYR]33:H.OH #1353 | Polar | [LYS]128:A.HZ3 #1233 | Basic, electrically charged | K427 |
| Heavy Chain CDR2 | 0.164 nm | [TYR]53:H.OH #1567 | Polar | [LYS]128:A.HZ1 #1231 | Basic, electrically charged | K427 |
| | 0.338 nm | [TYR]53:H.HH #1568 | Polar | [GLY]127:A.O #1222 | Nonpolar | G426 |
| | 0.31 nm | [TYR]53:H.HH #1568 | Polar | [LYS]128:A.HZ2 #1232 | Basic, electrically charged | K427 |
| Heavy Chain CDR3 | 0.175 nm | [ASP]98:H.OD2 #2033 | Acidic, electrically charged | [LYS]104:A.HZ1 #999 | Basic, electrically charged | K403 |
| | 0.304 nm | [ASP]98:H.OD2 #2033 | Acidic, electrically charged | [LYS]104:A.HZ2 #1000 | Basic, electrically charged | K403 |
| | 0.321 nm | [ASN]97:H.OD1 #2021 | Polar | [TYR]103:A.SD2 #984 | Polar | Y402 |

Example 8. Effects of CP1 on the Viability of Tumor and Normal Cells

Figure 5:
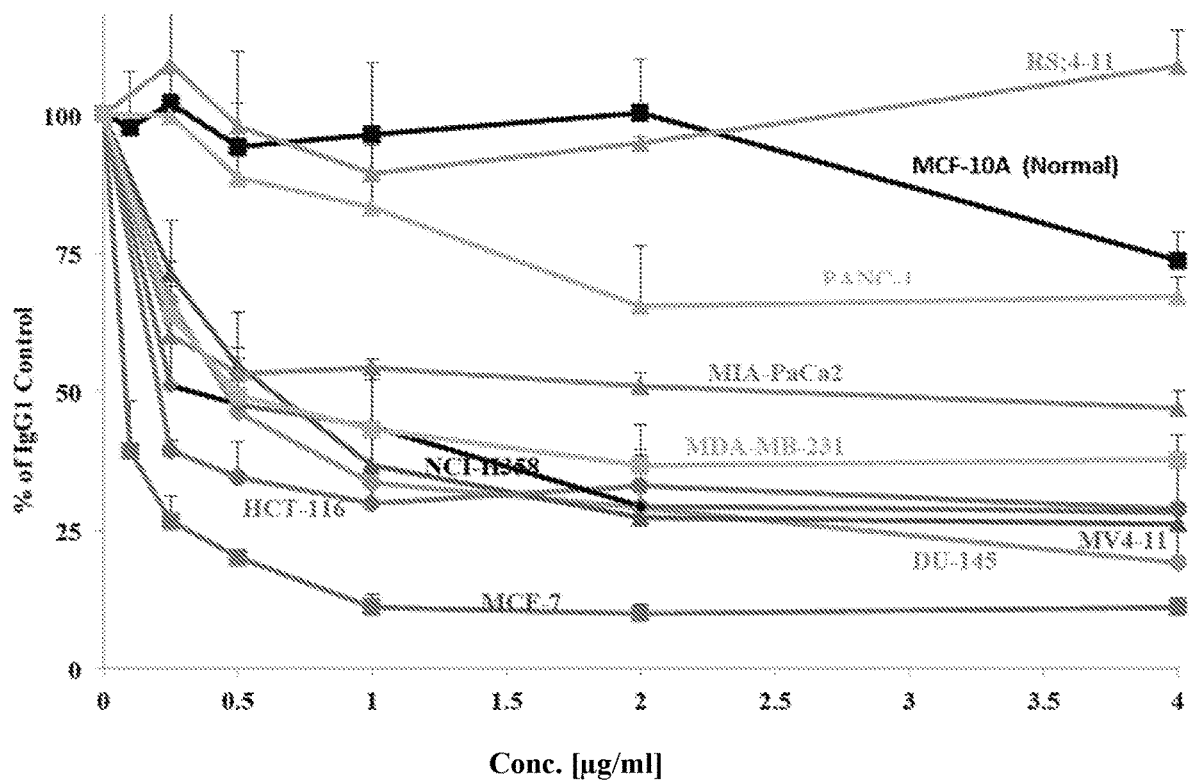
FIG. 5 is a line graph showing cytotoxic effects of CP1 on the viability on tumor and normal cells. Various solid tumor types and AML (MV4-11) and normal breast epithelial cells were incubated in 96 well plates for 24 h in RPMI1640 medium containing 10% human serum. After 24 h the cells were incubated with either human IgG1 antibody (control) or various concentrations of antibody CP1 for 96 h. Cells were then stained with trypan blue and counted in a NEXCELOM CELLOMETER Auto T4 Plus counter. IC50 results are the means of triplicate determinations plus S.D.
Figure 6:
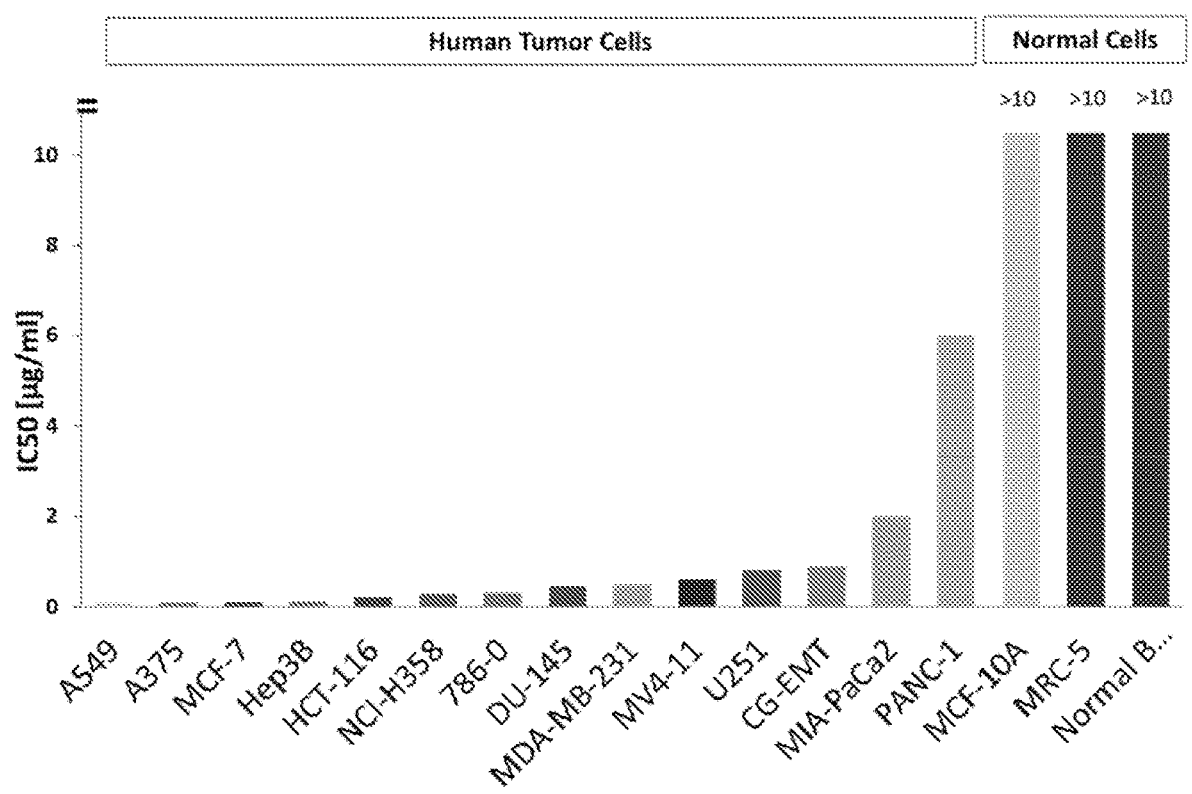
FIG. 6 is a bar graph showing the effects of CP1 (from B cells or recombinant cells) on various human cell lines. CP1 has potent widespread anticancer activity to both hematological and solid tumor cells in vitro, but negligible toxicity to normal cells.

CP1 is a potent inhibitor of tumor cell viability in vitro. FIG. 5 and FIG. 6 show that $IC_{50}$ values of less than 1 µg/ml were obtained for CP1 versus a broad range of tumor cells. For example, $IC_{50}$ of CP1 against human MV4-11 AML cells is 0.4 µg/ml. In contrast, the $IC_{50}$ concentrations of CP1 versus normal human B and myeloid cells, breast epithelial cells and lung fibroblasts were greater than 10 µg/ml. Unlike the tumor cells, these normal cells did not express detectable levels of nucleolin in either the plasma membrane or cytoplasm. The widespread and aberrant expression of the multifunctional protein nucleolin in human tumor cells, in contrast to the corresponding normal cells, explains both the broad-spectrum anticancer activity and tumor selectivity of antibody CP1.

Figure 8:
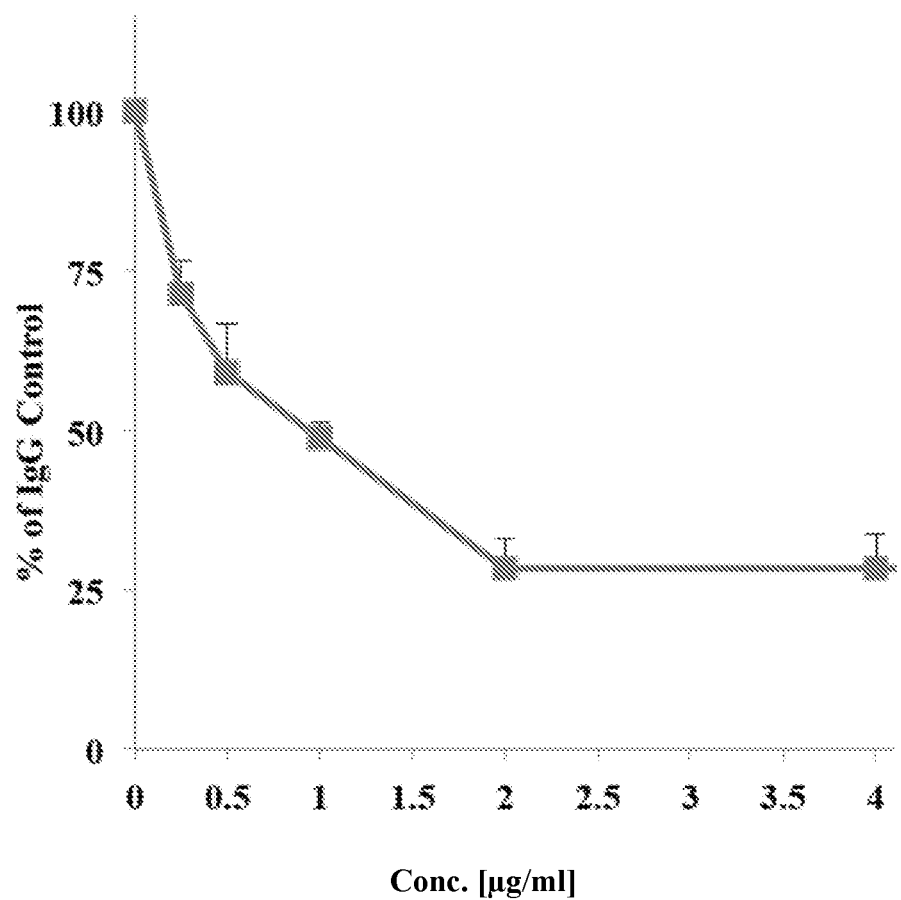
FIG. 8 is a line graph showing ex vivo effects of CP1 on the viability of patient prostate cancer CG-EMT cells. CG-EMT cells are primary cancer cells that were isolated from a patient with hormone-refractory prostate cancer.
Figures 9A, 9B, 9C:
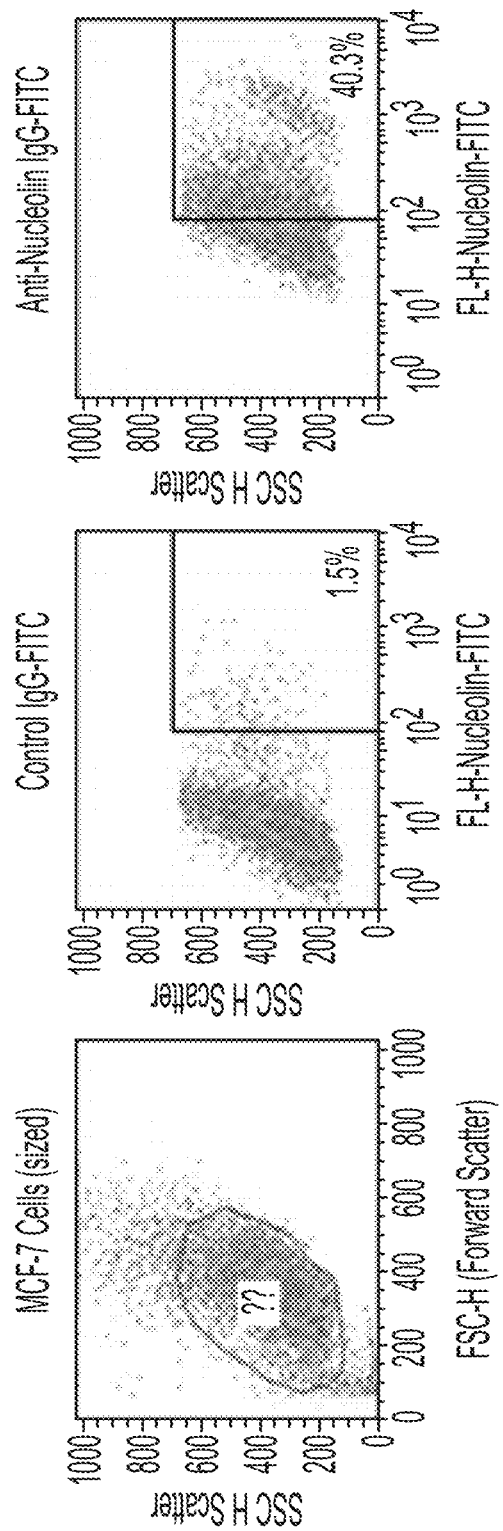
FIG. 9 is a set of images showing cell surface and plasma membrane binding of CP1 to cancer cells. Non-permeabilized MCF-7 cells were incubated for 1 h at room temperature with either a FITC-labeled isotype control antibody or CP1. The incorporation of CP1 into the plasma membrane was determined by indirect immunofluorescence using CP1 and a FITC-conjugated secondary Ab. Nuclei were counterstained with propidium iodide. The punctate appearance of nucleolin suggests that it was incorporated within lipid rafts in the plasma membrane.
Figure 10:
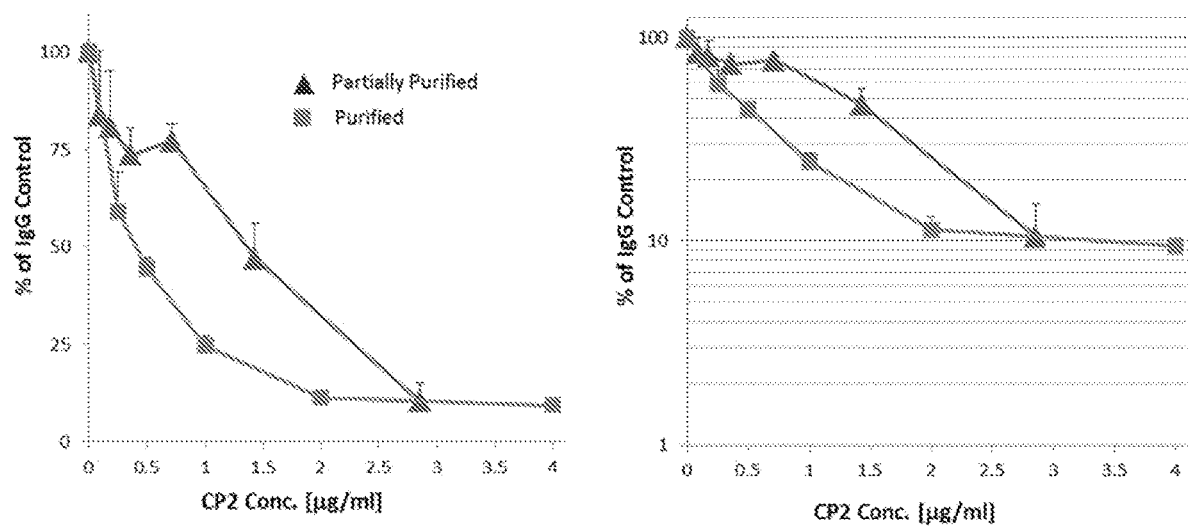
FIG. 10 is a set of line graphs showing purified (top lines) and partially purified (bottom lines) CP2 on cell numbers of MCF7 at 96 h.

Patient-derived CG-EMT prostate cancer cells were obtained from Michael B. Lilly, M.D. of the Hollings Cancer Center at the Medical University of South Carolina. The cells were cultured in RPMI media with 10% heat-inactivated fetal bovine serum and 1% antibiotics for 32 passages until cell growth became consistent. To test the potency of purified CP1 in killing CG-EMT cells, the cells were seeded onto 96 well plate at a density of 6000 cells per well. On the following day, the cells were incubated in triplicate with either 0 to 8 µg/ml of CP1 or with 0 to 8 µg/ml of isotype control human IgG$_1$ in the presence of 10% human AB serum. After 96 hours, cell viability was assayed using trypan blue exclusion and cell counting with a NEXCELOM Cellometer. Results are shown in FIG. 8.

Example 9. Effects of CP1(RC) on the Viability of Tumor Cells

Illustrative IC$_{50}$ Value Determination

The antiproliferative activity of CP1(RC) against the human tumor cell lines was investigated with Promega's Cell Titer-Glo® Luminescent Cell Viability assay.

TABLE 5

Cells and antibodies used in the IC$_{50}$ study.

| Tumor Type | Cell Line | Dilution | Test Agent; Top Conc. |
|---|---|---|---|
| Human Kidney Renal | 786-0 | 1:2 | CP1(RC): 8 µg/mL |
| Human Colon | HCT-116 | | IgG Control 1: 8 µg/mL |
| Human Glioma | U251 | | |
| Human Lung | A549 | | |
| Human Liver | Hep3B | | |
| Human Melanoma | A375 | | |

The human tumor cells were seeded in a clear polystyrene 96-well microculture plate (Corning® Costar® 96-well flat bottom plate, Cat. #3997) in a total volume of 90 µL/well. After 24 hours of incubation in a humidified incubator at 37° C. with 5% CO2 and 95% air, 10 µL of 10×, serially diluted test agents in growth medium were added to each well in duplicate (10 pt dose response, highest concentration 8 µg/mL). After 72 hours of culture in a humidified incubator at 37° C., in an atmosphere of 5% CO2 and 95% air, the plated cells and Cell Titer-Glo® (Promega G7571) reagents were brought to room temperature to equilibrate for 30 minutes. A picture was taken of the control wells to depict confluency at endpoint. 100 µL of Cell Titer-Glo® reagent was added to each well. The plate was shaken for two minutes and then left to equilibrate for ten minutes. The medium/Cell Titer-Glo® reagent was transferred to a white polystyrene 96-well microculture plate (Corning® Costar® 96-well flat bottom plate, Cat. #3917) before reading luminescence on the BioTek Synergy II microplate reader. The/Go value for the test agents were estimated using Graph Pad Prism 7.0 by plotting compound concentration (Log µM) versus % C and fitting the four parameter logistic equation to the normalized data by nonlinear regression.

TABLE 6

Results of IC$_{50}$ measurements.

| Cell Line | Agent | IC$_{50}$ (µg/mL) |
|---|---|---|
| 786-0 | CP1(RC) | 0.31 |
| 786-0 | IgG | >8 |
| HCT-116 | CP1(RC) | 0.69 |
| HCT-116 | IgG | 3.87 |
| U251 | CP1(RC) | 0.81 |
| U251 | IgG | 6.77 |
| A549 | CP1(RC) | 0.08 |
| A549 | IgG | >8 |
| Hep3B | CP1(RC) | 0.11 |
| Hep3B | IgG | >8 |
| A375 | CP1(RC) | 0.08 |
| A375 | IgG | 7.37 |

9. SEQUENCES OF CP1(RC), CP1, CP2, NUCLEOLIN 9.1. CP1(RC)

```
CP1(RC) Gamma heavy chain, nucleotide sequence
                                                      SEQ ID NO: 1
                    ATGAAACAC CTGTGGTTCT TTCTCCTGCT GGTGGCTGCT

CCCAGGTGGG TGCTGAGCCA GGTGCAGCTG CAGGAAAGCG GACCTGGCCT GGTCAAACCC

TCCCAGACAC TGAGCCTGAC CTGCACCGTC AGCGGCGGAT CCATCAACTC CGGCGGCTTC

TACTGGAGCT GGATCAGACA GCATCCTGGC AAGGGCCTCG AGTGGATCGG CTACATTAGC

TATACCGGCA GCACCTACTA CAATCCCTCC CTGAAGAGCA GGGTGAACAT TAGCGCCGAC

ACCTCCAAGA ACAGGTTCAG CCTGAAGCTC AGCAGCGTCA CCGCCGCCGA TACCGCCGTG

TACTACTGCG CCAGGGACAT GAACGACGGC CTGCAGATCT GGGGACAGGG CACACTGGTC

ACCGTGTCCG CTGCCAGCAC CAAGGGACCC AGCGTGTTCC CCCTGGCTCC CTCCTCCAAG

AGCACCTCCG GAGGCACCGC CGCCCTGGGC TGCCTGGTGA AGGATTACTT CCCCGAGCCC

GTGACCGTGA GCTGGAACAG CGGAGCCCTG ACAAGCGGAG TGCACACATT CCCTGCCGTG

CTGCAGAGCA GCGGCCTGTA CTCCCTGAGC TCCGTGGTCA CAGTGCCTAG CTCCTCCCTC

GGCACCCAGA CCTACATCTG CAACGTGAAC CATAAGCCCT CCAATACCAA GGTGGACAAG
```

```
AGGGTCGAGC CCAAATCCTG CGACAAGACA CACACCTGTC CTCCTTGCCC CGCCCCCGAA

CTGCTGGGCG GACCCTCCGT CTTCCTCTTC CCTCCTAAGC CCAAGGATAC CCTGATGATC

AGCAGGACAC CTGAGGTGAC CTGCGTGGTG GTGGACGTCT CCCACGAGGA CCCCGAGGTG

AAGTTCAACT GGTACGTGGA TGGCGTGGAG GTCCACAACG CCAAGACCAA GCCCAGAGAG

GAGCAGTACA ACAGCACATA CAGGGTGGTC TCCGTCCTGA CAGTGCTCCA CCAGGACTGG

CTGAATGGCA AGGAGTACAA GTGCAAGGTC AGCAACAAAG CCCTGCCCGC CCCTATCGAG

AAGACCATCA GCAAGGCTAA GGGCCAGCCC AGGGAGCCCC AGGTCTATAC CTGCCCCCC

AGCAGGGAAG AGATGACCAA GAATCAGGTC TCCCTGACCT GTCTGGTGAA GGGCTTCTAC

CCTAGCGACA TCGCCGTGGA GTGGGAGAGC AACGGCCAGC CTGAAAACAA CTACAAGACC

ACCCCTCCTG TGCTGGACTC CGACGGATCC TTCTTCCTGT ACTCCAAGCT GACCGTGGAT

AAAAGCAGGT GGCAACAGGG CAACGTGTTC TCCTGCTCCG TCATGCACGA AGCTCTGCAC

AACCACTACA CCCAGAAGAG CCTGTCCCTG AGCCCTGGCA AG

CP1(RC) Gamma heavy chain, amino acid sequence
                                                        SEQ ID NO: 2

1  MKHLWFFLLL VAAPRWVLSQ VQLQESGPGL VKPSQTLSLT CTVSGGSINS GGFYWSWIRQ

61  HPGKGLEWIG YISYTGSTYY NPSLKSRVNI SADTSKNRFS LKLSSVTAAD TAVYYCARDM

121  NDGLQIWGQG TLVTVSAAST KGPSVFPLAP SSKSTSGGTA ALGCLVKDYF PEPVTVSWNS

181  GALTSGVHTF PAVLQSSGLY SLSSVVTVPS SSLGTQTYIC NVNHKPSNTK VDKRVEPKSC

241  DKTHTCPPCP APELLGGPSV FLFPPKPKDT LMISRTPEVT CVVVDVSHED PEVKFNWYVD

301  GVEVHNAKTK PREEQYNSTY RVVSVLTVLH QDWLNGKEYK CKVSNKALPA PIEKTISKAK

361  GQPREPQVYT LPPSREEMTK NQVSLTCLVK GFYPSDIAVE WESNGQPENN YKTTPPVLDS

421  DGSFFLYSKL TVDKSRWQQG NVFSCSVMHE ALHNHYTQKS LSLSPGK

R234, E376, M378 are allotype residues identified by comparing the sequencing of the CP1 antibody to known allotype sequences in other human antibodies.

Residues Q20 to A137 of CP1(RC) Gamma heavy chain: variable region, amino acid
sequence
                                                        SEQ ID NO: 3
QVQLQESGPGLVKPSQTLSLTCTVSGGSINSGGFYWSWIRQHPGKGLEWIGYISYTGSTYYNPSLKSRVN
ISADTSKNRFSLKLSSVTAADTAVYYCARDMNDGLQIWGQGTLVTVSA Residues A138 to K467 of CP1(RC) Gamma heavy chain: constant region, amino acid
sequence
                                                        SEQ ID NO: 4
ASTKGPSVFPLAPSSKSTSGGTAALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPELLGGPSVFLFPPKPKDTLMISRTP

EVTCVVVDVSHEDPEVKFNWYVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

Residues M1 to S19 of CP1(RC) Gamma heavy chain: native signal peptide (leader),
amino acid sequence
                                                        SEQ ID NO: 5
MKHLWFFLLLVAAPRWVLS Residues A138 to V235 of CP1(RC) Gamma heavy chain: human CH1, amino acid
sequence
                                                        SEQ ID NO: 6
ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKRV
```

-continued

Residues E236 to P250 of CP1(RC) Gamma heavy chain: human G1 Hinge, amino acid sequence

SEQ ID NO: 7

EPKSCDKTHTCPPCP

Residues A251 to G361 of CP1(RC) Gamma heavy chain: human CH2, amino acid sequence

SEQ ID NO: 8

APELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKG

Residues Q362 to K467 of CP1(RC) Gamma heavy chain: human CH3, amino acid sequence

SEQ ID NO: 9

QPREPQVYTLPPSREEMTKNQVSLTCLVKGFYPSDIAVEWESNGQPENNYKTTPPVLDSDGSFFLYSKLT
VDKSRWQQGNVFSCSVMHEALHNHYTQKSLSLSPGK

CP1(RC) Kappa light chain, nucleotide sequence

SEQ ID NO: 10

```
                 ATGGACATG AGGGTGCCTG CCCAGCTGCT CGGACTGCTG
CTGCTGTGGC TGCCCGGAGC TAAGTGCGAC ATCCAGATGA CCCAGAGCCC TTCCACACTC
TCCGCCAGCG TGGGCGATAG GGTGACCATC ACCTGCAGGG CCAGCCAGTC CATCAGCAGG
TGGCTGGCCT GGTACCAGCA GAAGCCCGGC AAGGCCCCCA AGCTGCTGAT CTACAAGGCC
AGCACACTCG AGTCCGGCGT GCCCAGCAGA TTCAGCGGAA GCGGCAGCGG CACCGAGTTT
ACCCTGACCA TCAGCAGCCT GCAGCCCGAC GACTTCGCCA CCTACTACTG CCAGCAGTAC
AACTCCTATA GCAGGGCCTT CGGCCAGGGC ACCAAAGTGG AGATCAAGAG GACCGTGGCC
GCCCCTAGCG TCTTCATCTT CCCCCCCTCC GACGAGCAGC TGAAGAGCGG CACAGCCTCC
GTGGTGTGCC TGCTGAACAA CTTCTACCCC AGGGAGGCCA AGGTGCAGTG GAAGGTGGAC
AACGCCCTGC AGAGCGGCAA CTCCCAGGAG AGCGTGACCG AGCAGGACTC CAAGGACAGC
ACCTACAGCC TGAGCAGCAC CCTCACCCTG AGCAAGGCCG ACTACGAGAA GCACAAGGTG
TACGCCTGCG AGGTGACACA CCAGGGCCTG AGCAGCCCTG TGACCAAGTC TTTTAACAGG
GGCGAATGC
```

CP1(RC) Kappa light chain, amino acid sequence

SEQ ID NO: 11

```
  1  MDMRVPAQLL GLLLLWLPGA KCDIQMTQSP STLSASVGDR VTITCRASQS ISRWLAWYQQ
 61  KPGKAPKLLI YKASTLESGV PSRFSGSGSG TEFTLTISSL QPDDFATYYC QQYNSYSRAF
121  GQGTKVEIKR TVAAPSVFIF PPSDEQLKSG TASVVCLLNN FYPREAKVQW KVDNALQSGN
181  SQESVTEQDS KDSTYSLSST LTLSKADYEK HKVYACEVTH QGLSSPVTKS FNRGEC
```

A175 and V213 are allotype residues identified by comparing the sequencing of the CP1 antibody to known allotype sequences in other human antibodies.
Residues M1 to C22 are a native signal peptide (leader).

Residues D23 to K129 of CP1(RC) Kappa light chain: variable region, amino acid sequence

SEQ ID NO: 12

DIQMTQSPSTLSASVGDRVTITCRASQSISRWLAWYQQKPGKAPKLLIYK
ASTLESGVPSRFSGSGSGTEFTLTISSLQPDDFATYYCQQYNSYSRAFGQ
GTKVEIK

-continued

Residues R130 to C236 of CP1(RC) Kappa light chain: constant region, amino acid sequence

SEQ ID NO: 13

RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC 9.2. CP1

CP1 heavy chain, amino acid sequence

SEQ ID NO: 14

```
  1  MKHLWFFLLL VAAPRWVLSQ VQLQESGPGL VKPSQTLSLT CTVSGGSINS GGFYWSWIRQ
 61  HPGKGLEWIG YISYTGSTYY NPSLKSRVNI SADTSKNRFS LKLSSVTAAD TAVYYCARDM
121  NDGLQIWGQG TLVTVSAAST KGPSVFPLAP SSKSTSGGTA ALGCLVKDYF PEPVTVSWNS
```

```
181  GALTSGVHTF PAVLQSSGLY SLSSVVTVPS SSLGTQTYIC NVNHKPSNTK VDKKVEPKSC

241  DKTHTCPPCP APELLGGPSV FLFPPKPKDT LMISRTPEVT CVVVDVSHED PEVKFNWYVD

301  GVEVHNAKTK PREEQYNSTY RVVSVLTVLH QDWLNGKEYK CKVSNKALPA PIEKTISKAK

361  GQPREPQVYT LPPSRDELTK NQVSLTCLVK GFYPSDIAVE WESNGQPENN YKTTPPVLDS

421  DGSFFLYSKL TVDKSRWQQG NVFSCSVMHE ALHNHYTQKS LSLSPGK
```

Residues 20-137 of CP1 heavy chain: variable region, amino acid sequence
SEQ ID NO: 3
QVQLQESGPGLVKPSQTLSLTCTVSGGSINSGGFYWSWIRQHPGKGLEWIGYISYTGSTYYNPSLKSRVN
ISADTSKNRFSLKLSSVTAADTAVYYCARDMNDGLQIWGQGTLVTVSA Residues 138-467 of CP1 heavy chain: constant region, amino acid sequence
SEQ ID NO: 15
ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

```
CP1 light chain, amino acid sequence
                                                         SEQ ID NO: 11
  1  MDMRVPAQLL GLLLLWLPGA KCDIQMTQSP STLSASVGDR VTITCRASQS ISRWLAWYQQ

61  KPGKAPKLLI YKASTLESGV PSRFSGSGSG TEFTLTISSL QPDDFATYYC QQYNSYSRAF

121  GQGTKVEIKR TVAAPSVFIF PPSDEQLKSG TASVVCLLNN FYPREAKVQW KVDNALQSGN

181  SQESVTEQDS KDSTYSLSST LTLSKADYEK HKVYACEVTH QGLSSPVTKS FNRGEC
```

Residues D23 to K129 of CP1 light chain: variable region, amino acid sequence
SEQ ID NO: 12
DIQMTQSPSTLSASVGDRVTITCRASQSISRWLAWYQQKPGKAPKLLIYKASTLESGVPSRFSGSGSGTE
FTLTISSLQPDDFATYYCQQYNSYSRAFGQGTKVEIK Residues R130 to C236 of CP1 light chain: constant region, amino acid sequence
SEQ ID NO: 13
RTVAAPSVFIFPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC

9.3. Antibody CP2

CP2 Heavy chain variable region, nucleotide sequence
SEQ ID NO: 16
GGAAGGTGTGCACGCCGCTGGTCAGGGCGCCTGAGTTCCACGACACCGTCACCGGTTCGGGGAAGTAGTC
CTTGACCAGGCAGCCCAGGGCCGCTGTGCCCCCAGAGGTGCTCTTGGAGGAGGGTGCCAGGGGGAAGACC
GATGGGCCCTTGGTGGAGGCTGAGGAGACGGTGACCAGGGTTCCCAGGCCCCAGTAAACTCCTATAATAA
TCACTTCAGAAATCCTTCCGGAAGTGGTGCAATAATACACGGCTGTGTCCTCGGTTTGCAGGCTGTTCAT
TTGCAGATACATCGTATTTTTTGAATCATCTCTTGAGATGGTGAACCTGTCATTCACGGCTGCGGCGTAG
TCTGTTGTCCCACCATCAGATCTGCCCTTAATACGGCCAACCCACTCCAGCCCCTTCCCTGGAACCCGGC
GGACCCAATTCATCCAACTGTTCGCGAGACTGAGTCCAGAGACTGTACAGGAGAGTCTAAGGGACCCCCC
CGGCTGTACCAAGTCTCCCCCCGACTCCTCCAACTGCACCTCACACTGGACACCTT

```
CP2 Heavy chain variable region, amino acid sequence
                                                         SEQ ID NO: 17
  1  EVKLQESGPE LVKPGASVKI SCKASGYTFT DYFMIWVKQS HGKSLEWIGD INPSNGGSSY

61  NLKFKDKATL TVDKSSNTAY MDLRSLTSED SAVYYCARGQ FRLPAWFAYW GQGALVTVSA
```

CP2 Light chain variable region, nucleotide sequence
SEQ ID NO: 18
ATGAGGCTCCCTGCTCAGCTGCTGGGGCTGCTAATGCTCAGCGTCCCAGGGTCCAGTGGGGATGTTGTGC
TGACTCAGTCTCCACTCTCCCTGCCCGTAACCCCTGGACAGCCGGCCTCCATATCCTGCACGTCTACTCA

```
AAGCCTCGCACACAGCAATGGAGACACCTACTTGAATTGGTTTCTGCAGAGGCCAGGCCAAGCTCCAAGG

CGCCTATTTTATAACGTTTCTGACCGCGACTTTGGGGTCCCGGACAGATTCAGCGGCAGTGGGTCAGGCA

CTGATTTCACACTGAAAATCAGCAGGGTGGAGGCTGAGGATGTTGGCATTTATTACTGCATGCAGGGTAC

ACTCTGGCCTCCGACGTTCGGCCAAGGGACCAAGGTGGAAATCAAACGAACTGTGGCTGCACCATCTGTC

TTCATCTTCCCGCCATCTGATGAGCAGTTGAAATCTGGAACTGCCTCTGTTGTGTGCCTGCTGAATAACT

TCTATCCCAGAGAGGCCAAAGTACAGTGGAAGGTGGATAACGCCCTCCAATCGGGTAACTCCCAGGAGAG

TGTCACAGAGCAGGACAGCAAGGACAGCACCTACAGCC
```

CP2 Light chain variable region, amino acid sequence
SEQ ID NO: 19
```
  1   DVVLTQSPLS LPVTPGQPAS ISCTSTQSLA HSNGDTYLNW FLQRPGQAPR RLFYNVSDRD
 61   FGVPDRFSGS GSGTDFTLKI SRVEAEDVGI YYCMQGTLWP PTFGQGTKVE IK
```

9.4. Nucleolin

Nucleolin, amino acid sequence
SEQ ID NO: 20
```
  1     MVKLAKAGKN QGDPKKMAPP PKEVEEDSED EEMSEDEEDD SSGEEVVIPQ KKGKKAAATS
 61     AKKVVVSPTK KVAVATPAKK AAVTPGKKAA ATPAKKTVTP AKAVTTPGKK GATPGKALVA
121     TPGKKGAAIP AKGAKNGKNA KKEDSDEEED DDSEEDEEDD EDEDEDEDEI EPAAMKAAAA
181     APASEDEDDE DDEDDEDDDD DEEDDSEEEA METTPAKGKK AAKVVPVKAK NVAEDEDEEE
241     DDEDEDDDDD EDDEDDDDED DEEEEEEEEE EPVKEAPGKR KKEMAKQKAA PEAKKQKVEG
301     TEPTTAFNLF VGNLNFNKSA PELKTGISDV FAKNDLAVVD VRIGMTRKFG YVDFESAEDL
361     EKALELTGLK VFGNEIKLEK PKGKDSKKER DARTLLAKNL PYKVTQDELK EVFEDAAEIR
421     LVSKDGKSKG IAYIEFKTEA DAEKTFEEKQ GTEIDGRSIS LYYTGEKGQN QDYRGGKNST
481     WSGESKTLVL SNLSYSATEE TLQEVFEKAT FIKVPQNQNG KSKGYAFIEF ASFEDAKEAL
541     NSCNKREIEG RAIRLELQGP RGSPNARSQP SKTLFVKGLS EDTTEETLKE SFDGSVRARI
601     VTDRETGSSK GFGFVDFNSE EDAKAAKEAM EDGEIDGNKV TLDWAKPKGE GGFGGRGGGR
661     GGFGGRGGGR GGRGGFGGRG RGGFGGRGGF RGGRGGGGDH KPQGKKTKFE
```

Residues G300 to E466 of nucleolin, amino acid sequence
SEQ ID NO: 21
```
GTEPTTAFNLFVGNLNFNKSAPELKTGISDVFAKNDLAVVDVRIGMTRKFGYVDFESAEDLEKALELTGL
KVFGNEIKLEKPKGKDSKKERDARTLLAKNLPYKVTQDELKEVFEDAAEIRLVSKDGKSKGIAYIEFKTE
ADAEKTFEEKQGTEIDGRSISLYYTGE
```

TABLE 7

Part 1. Complementarity Determining Region (CDR) of Heavy Chain Variable Region (VH) of Antibody CP1/Antibody CP1(RC), SEQ ID NOS. 22 to 42

| VH | Framework H1 | CDR H1 | Framework H2 | CDR H2 | Framework H3 | CDR H3 | Framework H4 |
|---|---|---|---|---|---|---|---|
| Rosie Rosetta | QVQLQESGPGLV KPSQTLSLTCTVS (SEQ ID NO: 22) | GGSINSGGFY WS (SEQ ID NO: 24) | WIRQHPGKGLE WIG (SEQ ID NO: 27) | YISYTGSTYYN PSLKS (SEQ ID NO: 30) | RVNISADTSKNR FSLKLSSVTAAD TAVYYCAR (SEQ ID NO: 33) | DMNDGLQI (SEQ ID NO: 37) | WGQGTLVTVS A (SEQ ID NO: 40) |
| Paratome | QVQLQESGPGLV KPSQTLSLTCTVS G (SEQ ID NO: 23) | GSINSGGFYWS (SEQ ID NO: 25) | WIRQHPGKGLE WIG (SEQ ID NO: 28) | WIGYISYTGST YY (SEQ ID NO: 31) | NPSLKSRVNISA DTSKNRFSLKLS SVTAADTAVYY CA (SEQ ID NO: 34) | RDMNDGLQI (SEQ ID NO: 38) | WGQGTLVTVS A (SEQ ID NO: 40) |
| P.I.G.S. | QVQLQESGPGLV KPSQTLSLTCTVS (SEQ ID NO: 22) | GGSINSGG (SEQ ID NO: 26) | FYWSWIRQHP GKGLEWIG (SEQ ID NO: 29) | YIS | YTGSTYYNPSLK SRVNISADTSKNI RFSLKLSSVTAA DTAVY (SEQ ID NO: 35) | YCARDM (SEQ ID NO: 39) | NDGLQIWGQG TLVTVSA (SEQ ID NO: 41) |
| Chothia Definition | QVQLQESGPGLV KPSQTLSLTCTVS (SEQ ID NO: 22) | GGSINSGGFY WS (SEQ ID NO: 24) | WIRQHPGKGLE WIG (SEQ ID NO: 27) | YISYTGSTYYN PSL (SEQ ID NO: 32) | KSRVNISADTSK NRFSLKLSSVTA ADTAVYYCAR (SEQ ID NO: 36) | DMNDGLQI (SEQ ID NO: 37) | WGQGTLVTVS A (SEQ ID NO: 40) |

GSINSGG (SEQ ID NO: 42)

Part 2. CDR of Light Chain Variable Region (VL) of Antibody CP1/Antibody CP1(RC), SEQ ID NOS. 43 to 66

| VL | Framework L1 | CDR L1 | Framework L2 | CDR L2 | Framework L3 | CDR L3 | Framework L4 |
|---|---|---|---|---|---|---|---|
| Rosie Rosetta | DIQMTQSPSTL SASVGDRVTIT C (SEQ ID NO: 43) | RASQSISRWLA (SEQ ID NO: 46) | WYQQKPGKAP KLLIY (SEQ ID NO: 49) | KASTLES (SEQ ID NO: 52) | GVPSRFSGSG SGTEFTLTISSL QPDDFATYYC (SEQ ID NO: 55) | QQYNSY (SEQ ID NO: 58) | SRAFGQGTKV EIK (SEQ ID NO: 62) |
| Paratome | DIQMTQSPSTL SASVGDRVTIT CRAS (SEQ ID NO: 44) | QSISRWLA (SEQ ID NO: 47) | WYQQKPGKAP K (SEQ ID NO: 50) | LLIYKASTLES (SEQ ID NO: 53) | GVPSRFSGSG SGTEFTLTISSL QPDDFATYYC (SEQ ID NO: 55) | QQYNSYSRA (SEQ ID NO: 59) | FGQGTKVEIK (SEQ ID NO: 63) |
| P.I.G.S. | DIQMTQSPSTL SASVGDRVTIT CRA (SEQ ID NO: 45) | SQSISRWL (SEQ ID NO: 48) | AWYQQKPGKA PKLLIY (SEQ ID NO: 51) | KAST (SEQ ID NO: 54) | LESGVPSRFSG SGSGTEFTLTIS SLQPDDFATYY CQQ (SEQ ID NO: 56) | YNSYSR (SEQ ID NO: 60) | AFGQGTKVEIK (SEQ ID NO: 64) |

TABLE 7-continued

| Chothia Definition | DIQMTQSPSTL SASVGDRVTIT C (SEQ ID NO: 43) | RASQSISRWLA (SEQ ID NO: 46) | WYQQKPGKAP KLLIY (SEQ ID NO: 49) | KASTLES (SEQ ID NO: 52) | GVPSRFSGSG SGTEFTLTISSL QPDDFATYYC QQ (SEQ ID NO: 57) | YNSYSRA (SEQ ID NO: 61) | FGQGTKVEIK (SEQ ID NO: 63) |
|---|---|---|---|---|---|---|---|

QSISRWL (SEQ ID NO: 65)
YNSY (SEQ ID NO: 66)

GSINSGG (SEQ ID NO:42)

TABLE 8

Part 1. CDR of VH of antibody CP2 (SEQ ID NOS. 67 to 80)

| VH | Framework H1 | CDR H1 | Framework H2 | CDR H2 | Framework H3 | CDR H3 | Framework H4 |
|---|---|---|---|---|---|---|---|
| KABAT | EVKLQESGPEL VKPGASVKISC KASGYTFT (SEQ ID NO: 67) | DYFMI (SEQ ID NO: 69) | WVKQSHGKSL EWIG (SEQ ID NO: 71) | DINPSNGGSSY NLKFKD (SEQ ID NO: 73) | KATLTVDKSS NTAYMDLRSL TSEDSAVYYC AR (SEQ ID NO: 75) | GQFRLPAWFA Y (SEQ ID NO: 77) | WGQGALVTVS A (SEQ ID NO: 79) |
| IMGT | EVKLQESGPEL VKPGASVKISC KAS (SEQ ID NO: 68) | GYTFTDYF (SEQ ID NO: 70) | MIWVKQSHGK SLEWIGD (SEQ ID NO: 72) | INPSNGGS (SEQ ID NO: 74) | SYNLKFKDKA TLTVDKSSNT AYMDLRSLTS EDSAVYYC (SEQ ID NO: 76) | ARGQFRLPAW FAY (SEQ ID NO: 78) | WGQGALVTVS A (SEQ ID NO: 79) |
| Molecular Cloning Laboratories (MCLAB) | EVKLQESGPEL VKPGASVKISC KAS (SEQ ID NO: 68) | GYTFTDYF (SEQ ID NO: 70) | MIWVKQSHGK SLEWIGD (SEQ ID NO: 72) | INPSNGGS (SEQ ID NO: 74) | SYNLKFKDKA TLTVDKSSNT AYMDLRSLTS EDSAVYYC (SEQ ID NO: 76) | AR | GQFRLPAWFA YWGQGALVTV SA (SEQ ID NO: 80) |

Part 2. CDR of VL of antibody CP2 (SEQ ID NOS. 81 to 93)

| VL | Framework L1 | CDR L1 | Framework L2 | CDR L2 | Framework L3 | CDR L3 | Framework L4 |
|---|---|---|---|---|---|---|---|
| KABAT | DVVLTQSPLSLP VTPGQPASISC (SEQ ID NO: 81) | TSTQSLAHSNG DTYLN (SEQ ID NO: 83) | WFLQRPGQAP RRLFY (SEQ ID NO: 85) | NVSDRDF (SEQ ID NO: 87) | GVPDRFSGSGS GTDFTLKISRVE AEDVGIYYC (SEQ ID NO: 88) | MQGTLWPPT (SEQ ID NO: 90) | FGQGTKVEIK (SEQ ID NO: 92) |
| IMGT | DVVLTQSPLSLP VTPGQPASISCT ST (SEQ ID NO: 82) | QSLAHSNGDTY (SEQ ID NO: 84) | LNWFLQRPGQA PRRLFY (SEQ ID NO: 86) | NVS | DRDFGVPDRFS GSGSGTDFTLKI SRVEAEDVGIYY C (SEQ ID NO: 89) | MQGTLWPPT (SEQ ID NO: 90) | FGQGTKVEIK (SEQ ID NO: 92) |
| Molecular Cloning Laboratories (MCLAB) | DVVLTQSPLSLP VTPGQPASISCT ST (SEQ ID NO: 82) | QSLAHSNGDTY (SEQ ID NO: 84) | LNWFLQRPGQA PRRLFY (SEQ ID NO: 86) | NVS | DRDFGVPDRFS GSGSGTDFTLKI SRVEAEDVGIYY C (SEQ ID NO: 89) | MQGTLWPP (SEQ ID NO: 91) | TFGQGTKVEIK (SEQ ID NO: 93) |

All of the compositions and/or methods disclosed and claimed herein can be made and executed without undue experimentation in light of the present disclosure. It will be apparent to those of skill in the art that variations can be applied to the compositions and/or methods and in the steps or in the sequence of steps of the method described herein without departing from the concept, spirit and scope of the invention. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated antibody or fragment thereof, wherein the isolated antibody or fragment thereof binds to human nucleolin and comprises:
   a heavy chain CDR1 having an amino acid sequence that comprises SEQ ID NO:42;
   a heavy chain CDR2 having an amino acid sequence that comprises YIS;
   a heavy chain CDR3 having an amino acid sequence that comprises DM;
   a light chain CDR1 having an amino acid sequence that comprises SEQ ID NO:65;
   a light chain CDR2 having an amino acid sequence that comprises SEQ ID NO:54; and
   a light chain CDR3 having an amino acid sequence that comprises SEQ ID NO: 66,
   and wherein the sequence identity is determined with a sequence comparison computer program BLAST at the default parameters.

2. A pharmaceutical composition that comprises the isolated antibody or fragment thereof of claim 1, and a pharmaceutically acceptable carrier.

3. The isolated antibody or fragment thereof of claim 1, wherein the heavy chain variable region (VH) has at least 90% sequence identity to amino acid sequence SEQ ID NO:3, and wherein the light chain variable region (VL) has at least 90% sequence identity to amino acid sequence SEQ ID NO:12.

4. The isolated antibody or fragment thereof of claim 1, wherein the heavy chain variable region (VH) has at least 95% sequence identity to amino acid sequence SEQ ID NO:3, and wherein the light chain variable region (VL) has at least 95% sequence identity to amino acid sequence SEQ ID NO:12.

5. The isolated antibody or fragment thereof of claim 1, wherein the heavy chain variable region (VH) has at least 98% sequence identity to amino acid sequence SEQ ID NO:3, and wherein the light chain variable region (VL) has at least 98% sequence identity to amino acid sequence SEQ ID NO:12.

6. The isolated antibody or fragment thereof of claim 1, wherein the heavy chain has at least 85% sequence identity to amino acid sequence SEQ ID NO:2 or SEQ ID NO: 14, and wherein the light chain has at least 85% sequence identity to amino acid sequence SEQ ID NO: 11, and wherein the sequence identity is determined with a sequence comparison computer program BLAST at the default parameters.

7. The isolated antibody or fragment thereof of claim 6, wherein the heavy chain has at least 90% sequence identity to amino acid sequence SEQ ID NO:2 or SEQ ID NO: 14, and wherein the light chain has at least 90% sequence identity to amino acid sequence SEQ ID NO: 11.

8. The isolated antibody or fragment thereof of claim 6, wherein the heavy chain has an amino acid sequence that comprises SEQ ID NO:2 or SEQ ID NO: 14, and wherein the light chain has an amino acid sequence that comprises SEQ ID NO: 11.

9. A method of treating a cancer, comprising administering to a subject in need thereof an antibody or fragment thereof, wherein a cell of the cancer expresses human nucleolin, and wherein the antibody or fragment thereof binds to the human nucleolin and comprises:
- a heavy chain CDR1 having an amino acid sequence that comprises SEQ ID NO:42;
- a heavy chain CDR2 having an amino acid sequence that comprises YIS;
- a heavy chain CDR3 having an amino acid sequence that comprises DM;
- a light chain CDR1 having an amino acid sequence that comprises SEQ ID NO:65;
- a light chain CDR2 having an amino acid sequence that comprises SEQ ID NO:54; and
- a light chain CDR3 having an amino acid sequence that comprises SEQ ID NO: 66,
and wherein the sequence identity is determined with a sequence comparison computer program BLAST at the default parameters.

10. The method of claim 9, wherein the cancer is human lung cancer, skin cancer, breast cancer, liver cancer, colon cancer, lung cancer, kidney cancer, prostate cancer, leukemia, brain cancer, pancreas cancer, or any combination thereof.

11. The method of claim 9, wherein the subject is a human.

12. The method of claim 9, wherein: the heavy chain CDR1 has an amino acid sequence that consists of SEQ ID NO:42; the heavy chain CDR2 has an amino acid sequence that consists of YTS; the heavy chain CDR3 has an amino acid sequence that consists of DM; the light chain CDR1 has an amino acid sequence that consists of SEQ ID NO:65, the light chain CDR2 has an amino acid sequence that consists of SEQ ID NO:54; and the light chain CDR3 has an amino acid sequence that consists of SEQ ID NO:66.

* * * * *

SEQUENCE LISTING

```
<160> NUMBER OF SEQ ID NOS: 95

<210> SEQ ID NO 1
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgaaacacc tgtggttctt tctcctgctg gtggctgctc ccaggtgggt gctgagccag      60
gtgcagctgc aggaaagcgg acctggcctg gtcaaaccct cccagacact gagcctgacc     120
tgcaccgtca gcggcggatc catcaactcc ggcggcttct actggagctg gatcagacag     180
catcctggca agggcctcga gtggatcggc tacattagct ataccggcag cacctactac     240
aatccctccc tgaagagcag ggtgaacatt agcgccgaca cctccaagaa caggttcagc     300
ctgaagctca gcagcgtcac cgccgccgat accgccgtgt actactgcgc cagggacatg     360
aacgacggcc tgcagatctg gggacagggc acactggtca ccgtgtccgc tgccagcacc     420
aagggaccca gcgtgttccc cctggctccc tcctccaaga gcacctccgg aggcaccgcc     480
gccctgggct gcctggtgaa ggattacttc cccgagcccg tgaccgtgag ctggaacagc     540
ggagccctga caagcggagt gcacacattc cctgccgtgc tgcagagcag cggcctgtac     600
tccctgagct ccgtggtcac agtgcctagc tcctccctcg gcacccagac ctacatctgc     660
aacgtgaacc ataagccctc caataccaag gtggacaaga gggtcgagcc caaatcctgc     720
gacaagacac acacctgtcc tccttgcccc gcccccgaac tgctgggcgg accctccgtc     780
ttcctcttcc ctcctaagcc caaggatacc ctgatgatca gcaggacacc tgaggtgacc     840
tgcgtggtgg tggacgtctc ccacgaggac cccgaggtga agttcaactg gtacgtggat     900
ggcgtggagg tccacaacgc caagaccaag cccagagagg agcagtacaa cagcacatac     960
agggtggtct ccgtcctgac agtgctccac caggactggc tgaatggcaa ggagtacaag    1020
tgcaaggtca gcaacaaagc cctgcccgcc ctatcgaga agaccatcag caaggctaag    1080
ggccagccca gggagcccca ggtctatacc ctgccccca gcaggaaga gatgaccaag    1140 aatcaggtct ccctgacctg tctggtgaag ggcttctacc ctagcgacat cgccgtggag    1200
tgggagagca cggccagcc tgaaaacaac tacaagacca cccctcctgt gctggactcc    1260
gacggatcct tcttcctgta ctccaagctg accgtggata aaagcaggtg caacagggc    1320 aacgtgttct cctgctccgt catgcacgaa gctctgcaca accactacac ccagaagagc    1380
ctgtccctga gccctggcaa g                                              1401

<210> SEQ ID NO 2
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 2

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Asn Ser Gly Gly Phe Tyr Trp Ser Trp Ile Arg Gln His Pro Gly Lys
    50                  55                  60

Gly Leu Glu Trp Ile Gly Tyr Ile Ser Tyr Thr Gly Ser Thr Tyr Tyr
65                  70                  75                  80

Asn Pro Ser Leu Lys Ser Arg Val Asn Ile Ser Ala Asp Thr Ser Lys
                85                  90                  95

Asn Arg Phe Ser Leu Lys Leu Ser Ser Val Thr Ala Ala Asp Thr Ala
            100                 105                 110

Val Tyr Tyr Cys Ala Arg Asp Met Asn Asp Gly Leu Gln Ile Trp Gly
        115                 120                 125

Gln Gly Thr Leu Val Thr Val Ser Ala Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro

```
                    405                 410                 415
Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Gly Phe Tyr Trp Ser Trp Ile Arg Gln His Pro Gly Lys Gly Leu Glu
        35                  40                  45

Trp Ile Gly Tyr Ile Ser Tyr Thr Gly Ser Thr Tyr Tyr Asn Pro Ser
    50                  55                  60

Leu Lys Ser Arg Val Asn Ile Ser Ala Asp Thr Ser Lys Asn Arg Phe
65                  70                  75                  80

Ser Leu Lys Leu Ser Ser Val Thr Ala Ala Asp Thr Ala Val Tyr Tyr
                85                  90                  95

Cys Ala Arg Asp Met Asn Asp Gly Leu Gln Ile Trp Gly Gln Gly Thr
            100                 105                 110

Leu Val Thr Val Ser Ala
        115

<210> SEQ ID NO 4
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
```

```
                100             105                 110
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Lys His Leu Trp Phe Phe Leu Leu Leu Val Ala Ala Pro Arg Trp
1               5                   10                  15

Val Leu Ser

<210> SEQ ID NO 6
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Pro Lys Ser Cys Asp Lys Thr His Thr Cys Pro Pro Cys Pro
 1               5                  10                  15

<210> SEQ ID NO 8
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                 20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
         50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly
            100                 105                 110

<210> SEQ ID NO 9
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Pro Arg Glu Pro Gln Val Tyr Thr Leu Pro Pro Ser Arg Glu Glu
 1               5                  10                  15

Met Thr Lys Asn Gln Val Ser Leu Thr Cys Leu Val Lys Gly Phe Tyr
                 20                  25                  30

Pro Ser Asp Ile Ala Val Glu Trp Glu Ser Asn Gly Gln Pro Glu Asn
             35                  40                  45

Asn Tyr Lys Thr Thr Pro Pro Val Leu Asp Ser Asp Gly Ser Phe Phe
```

```
                50                  55                  60
Leu Tyr Ser Lys Leu Thr Val Asp Lys Ser Arg Trp Gln Gln Gly Asn
 65                  70                  75                  80

Val Phe Ser Cys Ser Val Met His Glu Ala Leu His Asn His Tyr Thr
                 85                  90                  95

Gln Lys Ser Leu Ser Leu Ser Pro Gly Lys
            100                 105
```

<210> SEQ ID NO 10
<211> LENGTH: 708
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atggacatga gggtgcctgc ccagctgctc ggactgctgc tgctgtggct gcccggagct      60
aagtgcgaca tccagatgac ccagagccct tccacactct ccgccagcgt gggcgatagg     120
gtgaccatca cctgcagggc cagccagtcc atcagcaggt ggctggcctg gtaccagcag     180
aagcccggca aggccccaa gctgctgatc tacaaggcca gcacactcga gtccggcgtg      240
cccagcagat tcagcggaag cggcagcggc accgagttta ccctgaccat cagcagcctg     300
cagcccgacg acttcgccac ctactactgc cagcagtaca actcctatag cagggccttc     360
ggccagggca ccaaagtgga gatcaagagg accgtggccg ccctagcgt cttcatcttc      420 cccccctccg acgagcagct gaagagcggc acagcctccg tggtgtgcct gctgaacaac     480
ttctacccca gggaggccaa ggtgcagtgg aaggtggaca cgccctgca gagcggcaac     540 tcccaggaga gcgtgaccga gcaggactcc aaggacagca cctacagcct gagcagcacc    600
ctcaccctga gcaaggccga ctacgagaag cacaaggtgt acgcctgcga ggtgacacac    660
cagggcctga gcagccctgt gaccaagtct tttaacaggg gcgaatgc                   708
```

<210> SEQ ID NO 11
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Met Asp Met Arg Val Pro Ala Gln Leu Leu Gly Leu Leu Leu Leu Trp
 1               5                  10                  15

Leu Pro Gly Ala Lys Cys Asp Ile Gln Met Thr Gln Ser Pro Ser Thr
                20                  25                  30

Leu Ser Ala Ser Val Gly Asp Arg Val Thr Ile Thr Cys Arg Ala Ser
            35                  40                  45

Gln Ser Ile Ser Arg Trp Leu Ala Trp Tyr Gln Lys Pro Gly Lys
        50                  55                  60

Ala Pro Lys Leu Leu Ile Tyr Lys Ala Ser Thr Leu Glu Ser Gly Val
 65                  70                  75                  80

Pro Ser Arg Phe Ser Gly Ser Gly Ser Gly Thr Glu Phe Thr Leu Thr
                 85                  90                  95

Ile Ser Ser Leu Gln Pro Asp Asp Phe Ala Thr Tyr Tyr Cys Gln Gln
            100                 105                 110

Tyr Asn Ser Tyr Ser Arg Ala Phe Gly Gln Gly Thr Lys Val Glu Ile
```

```
                115                 120                 125
Lys Arg Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Ala Phe Gly Gln Gly Thr Lys Val Glu Ile Lys
            100                 105

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
```

```
                65                  70                  75                  80
Lys His Lys Val Tyr Ala Cys Glu Val Thr His Gln Gly Leu Ser Ser
                    85                  90                  95

Pro Val Thr Lys Ser Phe Asn Arg Gly Glu Cys
                100                 105

<210> SEQ ID NO 14
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
                20                  25                  30

Pro Ser Gln Thr Leu Ser Leu Thr Cys Thr Val Ser Gly Gly Ser Ile
            35                  40                  45

Asn Ser Gly Gly Phe Tyr Trp Ser Trp Ile Arg Gln His Pro Gly Lys
    50                  55                  60

Gly Leu Glu Trp Ile Gly Tyr Ile Ser Tyr Thr Gly Ser Thr Tyr Tyr
65                  70                  75                  80

Asn Pro Ser Leu Lys Ser Arg Val Asn Ile Ser Ala Asp Thr Ser Lys
                85                  90                  95

Asn Arg Phe Ser Leu Lys Leu Ser Ser Val Thr Ala Ala Asp Thr Ala
            100                 105                 110

Val Tyr Tyr Cys Ala Arg Asp Met Asn Asp Gly Leu Gln Ile Trp Gly
        115                 120                 125

Gln Gly Thr Leu Val Thr Val Ser Ala Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320
```

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 15
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ggaaggtgtg cacgccgctg gtcagggcgc ctgagttcca cgacaccgtc accggttcgg      60
ggaagtagtc cttgaccagg cagcccaggg ccgctgtgcc cccagaggtg ctcttggagg     120
agggtgccag ggggaagacc gatgggccct tggtggaggc tgaggagacg gtgaccaggg     180
ttcccaggcc ccagtaaact cctataataa tcacttcaga aatccttccg gaagtggtgc     240
aataatacac ggctgtgtcc tcggtttgca ggctgttcat ttgcagatac atcgtatttt     300
ttgaatcatc tcttgagatg gtgaacctgt cattcacggc tgcggcgtag tctgttgtcc     360
caccatcaga tctgccctta atacggccaa cccactccag cccttccct ggaacccggc      420 ggacccaatt catccaactg ttcgcgagac tgagtccaga gactgtacag gagagtctaa     480 gggaccccc cggctgtacc aagtctcccc ccgactcctc caactgcacc tcacactgga     540
cacctt                                                                546

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Lys Leu Gln Glu Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Phe Met Ile Trp Val Lys Gln Ser His Gly Lys Ser Leu Glu Trp Ile
        35                  40                  45

Gly Asp Ile Asn Pro Ser Asn Gly Gly Ser Ser Tyr Asn Leu Lys Phe
    50                  55                  60

-continued

```
Lys Asp Lys Ala Thr Leu Thr Val Asp Lys Ser Asn Thr Ala Tyr
 65                  70                  75                  80

Met Asp Leu Arg Ser Leu Thr Ser Glu Asp Ser Ala Val Tyr Tyr Cys
                 85                  90                  95

Ala Arg Gly Gln Phe Arg Leu Pro Ala Trp Phe Ala Tyr Trp Gly Gln
            100                 105                 110

Gly Ala Leu Val Thr Val Ser Ala
        115                 120
```

<210> SEQ ID NO 18
<211> LENGTH: 598
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 18

```
atgaggctcc ctgctcagct gctggggctg ctaatgctca gcgtcccagg gtccagtggg      60
gatgttgtgc tgactcagtc tccactctcc ctgcccgtaa cccctggaca gccggcctcc     120
atatcctgca cgtctactca aagcctcgca cacagcaatg agacaccta cttgaattgg      180 tttctgcaga ggccaggcca agctccaagg cgcctatttt ataacgtttc tgaccgcgac     240
tttggggtcc cggacagatt cagcggcagt gggtcaggca ctgatttcac actgaaaatc     300
agcagggtgg aggctgagga tgttggcatt tattactgca tgcagggtac actctggcct     360
ccgacgttcg gccaagggac caaggtggaa atcaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcc      598
```

<210> SEQ ID NO 19
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 19

```
Asp Val Val Leu Thr Gln Ser Pro Leu Ser Leu Pro Val Thr Pro Gly
  1               5                  10                  15

Gln Pro Ala Ser Ile Ser Cys Thr Ser Thr Gln Ser Leu Ala His Ser
             20                  25                  30

Asn Gly Asp Thr Tyr Leu Asn Trp Phe Leu Gln Arg Pro Gly Gln Ala
         35                  40                  45

Pro Arg Arg Leu Phe Tyr Asn Val Ser Asp Arg Asp Phe Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Gly
                 85                  90                  95

Thr Leu Trp Pro Pro Thr Phe Gly Gln Gly Thr Lys Val Glu Ile Lys
            100                 105                 110
```

<210> SEQ ID NO 20
<211> LENGTH: 710
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 20

Met Val Lys Leu Ala Lys Ala Gly Lys Asn Gln Gly Asp Pro Lys Lys
1               5                   10                  15

Met Ala Pro Pro Lys Glu Val Glu Glu Asp Ser Glu Asp Glu Glu
            20                  25                  30

Met Ser Glu Asp Glu Glu Asp Ser Ser Gly Glu Glu Val Val Ile
        35                  40                  45

Pro Gln Lys Lys Gly Lys Lys Ala Ala Ala Thr Ser Ala Lys Lys Val
    50                  55                  60

Val Val Ser Pro Thr Lys Lys Val Ala Val Ala Thr Pro Ala Lys Lys
65                  70                  75                  80

Ala Ala Val Thr Pro Gly Lys Lys Ala Ala Thr Pro Ala Lys Lys
                85                  90                  95

Thr Val Thr Pro Ala Lys Ala Val Thr Thr Pro Gly Lys Lys Gly Ala
                100                 105                 110

Thr Pro Gly Lys Ala Leu Val Ala Thr Pro Gly Lys Lys Gly Ala Ala
            115                 120                 125

Ile Pro Ala Lys Gly Ala Lys Asn Gly Lys Asn Ala Lys Lys Glu Asp
130                 135                 140

Ser Asp Glu Glu Glu Asp Asp Ser Glu Glu Asp Glu Glu Asp Asp
145                 150                 155                 160

Glu Asp Glu Asp Glu Asp Glu Ile Glu Pro Ala Ala Met Lys
                165                 170                 175

Ala Ala Ala Ala Ala Pro Ala Ser Glu Asp Glu Asp Asp Glu Asp Asp
                180                 185                 190

Glu Asp Glu Asp Asp Asp Asp Glu Glu Asp Asp Ser Glu Glu
            195                 200                 205

Glu Ala Met Glu Thr Thr Pro Ala Lys Gly Lys Lys Ala Ala Lys Val
            210                 215                 220

Val Pro Val Lys Ala Lys Asn Val Ala Glu Asp Glu Asp Glu Glu
225                 230                 235                 240

Asp Asp Glu Asp Glu Asp Asp Asp Asp Glu Asp Asp Glu Asp Asp
                245                 250                 255

Asp Asp Glu Asp Asp Glu Glu Glu Glu Glu Glu Glu Glu Glu Pro
                260                 265                 270

Val Lys Glu Ala Pro Gly Lys Arg Lys Lys Glu Met Ala Lys Gln Lys
            275                 280                 285

Ala Ala Pro Glu Ala Lys Lys Gln Lys Val Gly Thr Glu Pro Thr
            290                 295                 300

Thr Ala Phe Asn Leu Phe Val Gly Asn Leu Asn Phe Asn Lys Ser Ala
305                 310                 315                 320

Pro Glu Leu Lys Thr Gly Ile Ser Asp Val Phe Ala Lys Asn Asp Leu
                325                 330                 335

Ala Val Val Asp Val Arg Ile Gly Met Thr Arg Lys Phe Gly Tyr Val
                340                 345                 350

Asp Phe Glu Ser Ala Glu Asp Leu Glu Lys Ala Leu Glu Leu Thr Gly
            355                 360                 365

Leu Lys Val Phe Gly Asn Glu Ile Lys Leu Glu Lys Pro Lys Gly Lys
370                 375                 380

-continued

```
Asp Ser Lys Lys Glu Arg Asp Ala Arg Thr Leu Leu Ala Lys Asn Leu
385                 390                 395                 400

Pro Tyr Lys Val Thr Gln Asp Glu Leu Lys Glu Val Phe Glu Asp Ala
            405                 410                 415

Ala Glu Ile Arg Leu Val Ser Lys Asp Gly Lys Ser Lys Gly Ile Ala
        420                 425                 430

Tyr Ile Glu Phe Lys Thr Glu Ala Asp Ala Glu Lys Thr Phe Glu Glu
    435                 440                 445

Lys Gln Gly Thr Glu Ile Asp Gly Arg Ser Ile Ser Leu Tyr Tyr Thr
450                 455                 460

Gly Glu Lys Gly Gln Asn Gln Asp Tyr Arg Gly Gly Lys Asn Ser Thr
465                 470                 475                 480

Trp Ser Gly Glu Ser Lys Thr Leu Val Leu Ser Asn Leu Ser Tyr Ser
            485                 490                 495

Ala Thr Glu Glu Thr Leu Gln Glu Val Phe Glu Lys Ala Thr Phe Ile
        500                 505                 510

Lys Val Pro Gln Asn Gln Asn Gly Lys Ser Lys Gly Tyr Ala Phe Ile
    515                 520                 525

Glu Phe Ala Ser Phe Glu Asp Ala Lys Glu Ala Leu Asn Ser Cys Asn
530                 535                 540

Lys Arg Glu Ile Glu Gly Arg Ala Ile Arg Leu Glu Leu Gln Gly Pro
545                 550                 555                 560

Arg Gly Ser Pro Asn Ala Arg Ser Gln Pro Ser Lys Thr Leu Phe Val
            565                 570                 575

Lys Gly Leu Ser Glu Asp Thr Thr Glu Glu Thr Leu Lys Glu Ser Phe
        580                 585                 590

Asp Gly Ser Val Arg Ala Arg Ile Val Thr Asp Arg Glu Thr Gly Ser
    595                 600                 605

Ser Lys Gly Phe Gly Phe Val Asp Phe Asn Ser Glu Glu Asp Ala Lys
610                 615                 620

Ala Ala Lys Glu Ala Met Glu Asp Gly Glu Ile Asp Gly Asn Lys Val
625                 630                 635                 640

Thr Leu Asp Trp Ala Lys Pro Lys Gly Glu Gly Gly Phe Gly Gly Arg
            645                 650                 655

Gly Gly Gly Arg Gly Gly Phe Gly Gly Arg Gly Gly Arg Gly Gly Gly
        660                 665                 670

Arg Gly Gly Phe Gly Gly Arg Gly Arg Gly Gly Phe Gly Gly Arg Gly
    675                 680                 685

Gly Phe Arg Gly Gly Arg Gly Gly Gly Gly Asp His Lys Pro Gln Gly
690                 695                 700

Lys Lys Thr Lys Phe Glu
705                 710
```

<210> SEQ ID NO 21
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gly Thr Glu Pro Thr Thr Ala Phe Asn Leu Phe Val Gly Asn Leu Asn
1               5                   10                  15

Phe Asn Lys Ser Ala Pro Glu Leu Lys Thr Gly Ile Ser Asp Val Phe
            20                  25                  30
```

Ala Lys Asn Asp Leu Ala Val Val Asp Val Arg Ile Gly Met Thr Arg
         35                  40                  45

Lys Phe Gly Tyr Val Asp Phe Glu Ser Ala Glu Asp Leu Glu Lys Ala
     50                  55                  60

Leu Glu Leu Thr Gly Leu Lys Val Phe Gly Asn Glu Ile Lys Leu Glu
 65                  70                  75                  80

Lys Pro Lys Gly Lys Asp Ser Lys Lys Glu Arg Asp Ala Arg Thr Leu
                 85                  90                  95

Leu Ala Lys Asn Leu Pro Tyr Lys Val Thr Gln Asp Glu Leu Lys Glu
             100                 105                 110

Val Phe Glu Asp Ala Ala Glu Ile Arg Leu Val Ser Lys Asp Gly Lys
            115                 120                 125

Ser Lys Gly Ile Ala Tyr Ile Glu Phe Lys Thr Glu Ala Asp Ala Glu
        130                 135                 140

Lys Thr Phe Glu Glu Lys Gln Gly Thr Glu Ile Asp Gly Arg Ser Ile
145                 150                 155                 160

Ser Leu Tyr Tyr Thr Gly Glu
                165

<210> SEQ ID NO 22
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 23
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Val Gln Leu Gln Glu Ser Gly Pro Gly Leu Val Lys Pro Ser Gln
1               5                   10                  15

Thr Leu Ser Leu Thr Cys Thr Val Ser Gly
            20                  25

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Ser Ile Asn Ser Gly Gly Phe Tyr Trp Ser
1               5                   10

<210> SEQ ID NO 25
<211> LENGTH: 11

-continued

<210> SEQ ID NO 25
<211> LENGTH: (implied)
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ser Ile Asn Ser Gly Gly Phe Tyr Trp Ser
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Ser Ile Asn Ser Gly Gly
1               5

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp Ile Arg Gln His Pro Gly Lys Gly Leu Glu Trp Ile Gly
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Ile Arg Gln His Pro Gly Lys Gly Leu Glu
1               5                   10

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Phe Tyr Trp Ser Trp Ile Arg Gln His Pro Gly Lys Gly Leu Glu Trp
1               5                   10                  15

Ile Gly

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Ile Ser Tyr Thr Gly Ser Thr Tyr Asn Pro Ser Leu Lys Ser
1               5                   10                  15

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Trp Ile Gly Tyr Ile Ser Tyr Thr Gly Ser Thr Tyr Tyr
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Ile Ser Tyr Thr Gly Ser Thr Tyr Tyr Asn Pro Ser Leu
1               5                   10

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Arg Val Asn Ile Ser Ala Asp Thr Ser Lys Asn Arg Phe Ser Leu Lys
1               5                   10                  15

Leu Ser Ser Val Thr Ala Ala Asp Thr Ala Val Tyr Tyr Cys Ala Arg
                20                  25                  30

<210> SEQ ID NO 34
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asn Pro Ser Leu Lys Ser Arg Val Asn Ile Ser Ala Asp Thr Ser Lys
1               5                   10                  15

Asn Arg Phe Ser Leu Lys Leu Ser Ser Val Thr Ala Ala Asp Thr Ala
                20                  25                  30

Val Tyr Tyr Cys Ala
            35

<210> SEQ ID NO 35
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Tyr Thr Gly Ser Thr Tyr Tyr Asn Pro Ser Leu Lys Ser Arg Val Asn
1               5                   10                  15

Ile Ser Ala Asp Thr Ser Lys Asn Arg Phe Ser Leu Lys Leu Ser Ser
            20                  25                  30

Val Thr Ala Ala Asp Thr Ala Val Tyr
        35                  40
```

<210> SEQ ID NO 36
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Lys Ser Arg Val Asn Ile Ser Ala Asp Thr Ser Lys Asn Arg Phe Ser
1               5                   10                  15

Leu Lys Leu Ser Ser Val Thr Ala Ala Asp Thr Ala Val Tyr Tyr Cys
            20                  25                  30

Ala Arg
```

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Asp Met Asn Asp Gly Leu Gln Ile
1               5
```

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Arg Asp Met Asn Asp Gly Leu Gln Ile
1               5
```

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Tyr Cys Ala Arg Asp Met
1               5
```

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 40

Trp Gly Gln Gly Thr Leu Val Thr Val Ser Ala
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asn Asp Gly Leu Gln Ile Trp Gly Gln Gly Thr Leu Val Thr Val Ser
1               5                   10                  15

Ala

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Ser Ile Asn Ser Gly Gly
1               5

<210> SEQ ID NO 43
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 44
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Ile Gln Met Thr Gln Ser Pro Ser Thr Leu Ser Ala Ser Val Gly
1               5                   10                  15

Asp Arg Val Thr Ile Thr Cys Arg Ala Ser
            20                  25

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 45

Asp Ile Gln Met Thr Gln Ser Pro Ser Thr Leu Ser Ala Ser Val Gly
1               5                   10                  15

Asp Arg Val Thr Ile Thr Cys Arg Ala
            20                  25

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ala Ser Gln Ser Ile Ser Arg Trp Leu Ala
1               5                   10

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ser Ile Ser Arg Trp Leu Ala
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Gln Ser Ile Ser Arg Trp Leu
1               5

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Trp Tyr Gln Gln Lys Pro Gly Lys Ala Pro Lys Leu Leu Ile Tyr
1               5                   10                  15

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Tyr Gln Gln Lys Pro Gly Lys Ala Pro Lys
1               5                   10
```

```
<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Trp Tyr Gln Gln Lys Pro Gly Lys Ala Pro Lys Leu Leu Ile Tyr
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Ala Ser Thr Leu Glu Ser
1               5

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Leu Ile Tyr Lys Ala Ser Thr Leu Glu Ser
1               5                   10

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Ala Ser Thr
1

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 56
<211> LENGTH: 37
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 56

Leu Glu Ser Gly Val Pro Ser Arg Phe Ser Gly Ser Gly Ser Gly Thr
1               5                   10                  15

Glu Phe Thr Leu Thr Ile Ser Ser Leu Gln Pro Asp Asp Phe Ala Thr
            20                  25                  30

Tyr Tyr Cys Gln Gln
        35

<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

Gln Gln

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Gln Tyr Asn Ser Tyr
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Gln Tyr Asn Ser Tyr Ser Arg Ala
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Tyr Asn Ser Tyr Ser Arg
1               5

<210> SEQ ID NO 61
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 61

Tyr Asn Ser Tyr Ser Arg Ala
1               5

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Arg Ala Phe Gly Gln Gly Thr Lys Val Glu Ile Lys
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Phe Gly Gln Gly Thr Lys Val Glu Ile Lys
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Phe Gly Gln Gly Thr Lys Val Glu Ile Lys
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Ser Ile Ser Arg Trp Leu
1               5

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Asn Ser Tyr
1
```

<210> SEQ ID NO 67
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Lys Leu Gln Glu Ser Gly Pro Glu Leu Val Lys Pro Gly Ala
1               5                   10                  15

Ser Val Lys Ile Ser Cys Lys Ala Ser Gly Tyr Thr Phe Thr
            20                  25                  30

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Val Lys Leu Gln Glu Ser Gly Pro Glu Leu Val Lys Pro Gly Ala
1               5                   10                  15

Ser Val Lys Ile Ser Cys Lys Ala Ser
            20                  25

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Tyr Phe Met Ile
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Tyr Thr Phe Thr Asp Tyr Phe
1               5

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Trp Val Lys Gln Ser His Gly Lys Ser Leu Glu Trp Ile Gly
1               5                   10

<210> SEQ ID NO 72
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Met Ile Trp Val Lys Gln Ser His Gly Lys Ser Leu Glu Trp Ile Gly
1               5                   10                  15

Asp

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Ile Asn Pro Ser Asn Gly Gly Ser Ser Tyr Asn Leu Lys Phe Lys
1               5                   10                  15

Asp

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Asn Pro Ser Asn Gly Gly Ser
1               5

<210> SEQ ID NO 75
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Lys Ala Thr Leu Thr Val Asp Lys Ser Ser Asn Thr Ala Tyr Met Asp
1               5                   10                  15

Leu Arg Ser Leu Thr Ser Glu Asp Ser Ala Val Tyr Tyr Cys Ala Arg
                20                  25                  30

<210> SEQ ID NO 76
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ser Tyr Asn Leu Lys Phe Lys Asp Lys Ala Thr Leu Thr Val Asp Lys
1               5                   10                  15

Ser Ser Asn Thr Ala Tyr Met Asp Leu Arg Ser Leu Thr Ser Glu Asp
                20                  25                  30

Ser Ala Val Tyr Tyr Cys
                35
```

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Gln Phe Arg Leu Pro Ala Trp Phe Ala Tyr
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Arg Gly Gln Phe Arg Leu Pro Ala Trp Phe Ala Tyr
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Gly Gln Gly Ala Leu Val Thr Val Ser Ala
1               5                   10

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Gln Phe Arg Leu Pro Ala Trp Phe Ala Tyr Trp Gly Gln Gly Ala
1               5                   10                  15

Leu Val Thr Val Ser Ala
            20

<210> SEQ ID NO 81
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Val Val Leu Thr Gln Ser Pro Leu Ser Leu Pro Val Thr Pro Gly
1               5                   10                  15

Gln Pro Ala Ser Ile Ser Cys
            20

<210> SEQ ID NO 82

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Val Val Leu Thr Gln Ser Pro Leu Ser Leu Pro Val Thr Pro Gly
1               5                   10                  15

Gln Pro Ala Ser Ile Ser Cys Thr Ser Thr
            20                  25

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Ser Thr Gln Ser Leu Ala His Ser Asn Gly Asp Thr Tyr Leu Asn
1               5                   10                  15

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Ser Leu Ala His Ser Asn Gly Asp Thr Tyr
1               5                   10

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Trp Phe Leu Gln Arg Pro Gly Gln Ala Pro Arg Arg Leu Phe Tyr
1               5                   10                  15

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Asn Trp Phe Leu Gln Arg Pro Gly Gln Ala Pro Arg Arg Leu Phe
1               5                   10                  15

Tyr

<210> SEQ ID NO 87
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 87

Asn Val Ser Asp Arg Asp Phe
1               5

<210> SEQ ID NO 88
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Ile Tyr Tyr Cys
            20                  25                  30

<210> SEQ ID NO 89
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Arg Asp Phe Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Ile Tyr Tyr Cys
            35

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Met Gln Gly Thr Leu Trp Pro Pro Thr
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Met Gln Gly Thr Leu Trp Pro Pro
1               5

<210> SEQ ID NO 92
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 92

Phe Gly Gln Gly Thr Lys Val Glu Ile Lys
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Phe Gly Gln Gly Thr Lys Val Glu Ile Lys
1               5                   10

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 94

His His His His His His
1               5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Glu Trp Ile Gly
1               5
```